US007238368B2

(12) United States Patent
Zalipsky et al.

(10) Patent No.: US 7,238,368 B2
(45) Date of Patent: Jul. 3, 2007

(54) RELEASABLE LINKAGE AND COMPOSITIONS CONTAINING SAME

(75) Inventors: Samuel Zalipsky, Redwood City, CA (US); Radwan Kiwan, Albany, CA (US)

(73) Assignee: ALZA Corporation, Mountain View, CA (US)

( * ) Notice: Subject to any disclaimer, the term of this patent is extended or adjusted under 35 U.S.C. 154(b) by 501 days.

(21) Appl. No.: 10/723,473

(22) Filed: Nov. 26, 2003

(65) Prior Publication Data

US 2004/0213759 A1   Oct. 28, 2004

Related U.S. Application Data

(63) Continuation-in-part of application No. 10/371,169, filed on Feb. 21, 2003, now Pat. No. 6,849,270, which is a continuation of application No. 09/982,336, filed on Oct. 15, 2001, now Pat. No. 6,605,299, which is a continuation of application No. 09/556,056, filed on Apr. 21, 2000, now Pat. No. 6,342,244.

(60) Provisional application No. 60/130,897, filed on Apr. 23, 1999.

(51) Int. Cl.
*A61K 9/127* (2006.01)
*C25D 3/60* (2006.01)
*A61K 45/00* (2006.01)
*A61K 38/00* (2006.01)
*A01N 61/00* (2006.01)
*C08B 11/00* (2006.01)

(52) U.S. Cl. ............... 424/450; 424/85.1; 205/254; 514/1; 530/336; 536/84

(58) Field of Classification Search .............. 424/450, 424/85.1; 205/254; 514/1; 530/336; 536/84
See application file for complete search history.

(56) References Cited

U.S. PATENT DOCUMENTS

| 4,021,449 A | 5/1977 | Fujimoto et al. |
| 4,179,337 A | 12/1979 | Davis et al. |
| 4,766,106 A | 8/1988 | Katre et al. |
| 4,902,502 A | 2/1990 | Nitecki et al. |
| 4,917,888 A | 4/1990 | Katre et al. |

(Continued)

FOREIGN PATENT DOCUMENTS

EP    0 317 956 A2    5/1989

(Continued)

OTHER PUBLICATIONS

Brois, S.J., et al., *J. Amer. Chem. Soc.* 92(26):7629-7631 (1970).

(Continued)

*Primary Examiner*—Jezia Riley
(74) *Attorney, Agent, or Firm*—Perkins Coie LLP; Judy M. Mohr

(57) ABSTRACT

A conjugate comprised of a hydrophilic polymer covalently yet reversibly linked to a amine-, hydroxy- or carboxyl-containing ligand is described. The resulting conjugate is capable of releasing the parent amine, hydroxy, or carboxyl-containing compound via thiol-mediated cleavage. The system allows for delivery of various amino-, hydroxy-, or carboxy-containing drugs in the form of their thiolytically cleavable macromolecular conjugates.

20 Claims, 31 Drawing Sheets

U.S. PATENT DOCUMENTS

| | | | |
|---|---|---|---|
| 4,935,465 | A | 6/1990 | Garman |
| 5,103,556 | A | 4/1992 | Filip et al. |
| 5,395,619 | A | 3/1995 | Zalipsky et al. |
| 5,631,018 | A | 5/1997 | Zalipsky et al. |
| 5,891,468 | A | 4/1999 | Martin et al. |
| 6,180,095 | B1 | 1/2001 | Greenwald et al. |
| 6,342,244 | B1* | 1/2002 | Zalipsky ............... 424/450 |
| 6,365,179 | B1* | 4/2002 | Zalipsky et al. ........ 424/450 |
| 6,605,299 | B2* | 8/2003 | Zalipsky ............... 424/450 |
| 6,638,500 | B1 | 10/2003 | El-Tayar et al. |
| 6,849,270 | B2* | 2/2005 | Zalipsky ............... 424/450 |
| 2004/0213579 | A1 | 10/2004 | Zalipsky et al. |

FOREIGN PATENT DOCUMENTS

| | | |
|---|---|---|
| EP | 0 317 956 A3 | 5/1989 |
| EP | 0 317 957 B1 | 5/1989 |
| EP | 0 510 197 A1 | 10/1992 |
| EP | 0 898 968 B1 | 3/1999 |
| FR | 2 254 336 | 7/1975 |
| JP | 1113391 | 5/1989 |
| WO | WO 97/36904 | 10/1997 |
| WO | WO 98/16201 | 4/1998 |
| WO | WO 99/29302 | 6/1999 |
| WO | WO00/64483 A2 | 11/2000 |
| WO | WO00/64483 A3 | 11/2000 |
| WO | WO 00/64484 A2 | 11/2000 |
| WO | WO 00/64484 A3 | 11/2000 |
| WO | WO01/26629 A2 | 4/2001 |
| WO | WO01/26629 A3 | 4/2001 |
| WO | WO02/26265 A2 | 4/2002 |
| WO | WO02/26265 A3 | 4/2002 |
| WO | WO03/053409 | 7/2003 |
| WO | WO2004/110497 A2 | 12/2004 |
| WO | WO2004/110497 A3 | 12/2004 |

OTHER PUBLICATIONS

Dittmer, J.C., et al., *J. Lipid Res.* 126-127 (1964).
Gaber, M., et al., *Pharmaceutical Res* 12(10):1407-1416, (1995).
Grice, R., et al., *J. Chem. Soc.* p. 1947-1954 (1963).
Hirota, S., *International J of Pharmaceutics* 162(1-2):185-194, (1998).
Johnsson, M., et al., *J of Liposome Res* 9(1):53-79, (1999).
Kaneko, T., et al., *Bioconjugate Chem.* 2(3):133-141 (1991).
Kirpotin, D., et al., *FEBS Letters* 388:115-118, (1996).
Lash, L.H., et al., *Arch. Biochem. Biophys.* 240(2):583-592 (1985).
Mueller, C.E., et al., 322(6):343-350, (1989).
Senter, P.D., et al., *J Org Chem* 55(9):2975-2978, (1990).
Vaage, J., et al., *Cancer* 72(12):3671-3675, (1993).
Vaage, J., et al., *Cancer* 73(5):1478-1484, (1994).
Vaage, J., et al., *International J of Cancer* 51(6)942-948, ( ).
Veronese, et al., *Applied Biochem. And Biotech.* p. 141-152 (1985).
Zalipsky, et al., *Biotechnol. Appl. Biochem.* p. 100-114 (1992).
Zalipsky, et al., *Eur. Polymer. J.* 19(12):1177-1183 (1983).
Zalipsky, et al., *Bioconj. Chem.* 4:296-299 (1993).
Zalipsky, *Bioconj Chem* 10(5):703-707, (1999).
Kratz, F., et al., *J. Med. Chem.* 45:5523-5533 (2002).
Thorpe, P., et al., *Cancer Research* 47:5924-5931 (1987).
Vaage, J., et al., *Int. J. Cancer* 80:134-137 (1999).
Worrell, N.R., et al., *Anti-Cancer Drug Design* 1:179-188 (1986).
Asai et al., *Biol. Pharm. Bull.*, 21(7):766-771 (1998).
Briddell et al., *Blood*, 102(11):163b-164b, Abstract #4364 (1999).
Database Dissertation Abstracts [Online] Proquest Info & Learning; Woghiren, Clement O. et al.: "Synthesis, Characterization and Conjugation of a Novel Protected Thiol-Polyethylene Glycol: A New Activated Polymer for Reversible Protein Modification (IL-2)" Dialog Accession No. 01367093; Dissertation Abstracts 55(03-B), 1994, p. 866.
Diaz et al., Bioconjugate Chemistry, 9:250-254 (1998).
Ellman, G.I., *Arch. Biochem. Biophys.*, 82:70-77 (1959).
Engman et al., Bioorganic & Medical Chemistry, 11:5091-5100 (2003).
Grassetti and Murray, *Arch. Biochem. Biophys.*, 119(1):41-49 (1967).
Johnson et al., Chemistry and Biology, 4(12):939-950 (1997).
Malik et al., Experimental Hematology, 28(7, Suppl. 1):p. 106, Abstract No. 237 (2000).
Zalipsky et al., Bioconjugate Chem., 10(5):703-707 (1999).
Zalipsky, S., et al., 28th International Symposium on Controlled Release of Bioactive Materials and 4th Consumer & Diversified Products Conference, San Diego, CA, Publisher: Controlled Release Society 1:437-438, (2001).

* cited by examiner

Mitomycin C (MMC)

RELEASABLE LINKAGE AND COMPOSITIONS CONTAINING SAME

This application is a continuation-in-part of U.S. application Ser. No. 10/371,169, filed Feb. 21, 2003, now U.S. Pat. No. 6,849,270, which is a continuation of U.S. application Ser. No. 09/982,336, filed Oct. 15, 2001, now U.S. Pat. No. 6,605,299, which is a continuation of U.S. application Ser. No. 09/556,056, filed Apr. 21, 2000, now U.S. Pat. No. 6,342,244, which claims priority to U.S. Provisional Application No. 60/130,897, filed Apr. 23, 1999, all of which are incorporated herein by reference in their entirety.

FIELD OF THE INVENTION

The present invention relates to a conjugate comprising a hydrophilic polymer, such as polyethyleneglycol, cleavably linked to a ligand derived from an amine-, hydroxyl- or carboxyl-containing compound, which in preferred embodiments can be an amine- or hydroxyl-containing lipid, drug or protein. The conjugates are cleavable under mild, physiologically attainable, thiolytic conditions to regenerate the amine-, hydroxyl- or carboxyl-containing compound in its original form.

BACKGROUND OF THE INVENTION

Hydrophilic polymers, such as polyethylene glycol (PEG), have been used for modification of various substrates, such as polypeptides, drugs and liposomes, in order to reduce immunogenicity of the substrate and/or to improve its blood circulation lifetime (Zalipsky, S. *Adv. Drug Del. Rev.*, 16:157 (1995)).

For example, parenterally administered proteins can be immunogenic and may have a short pharmacological half-life. Proteins can also be relatively water insoluble. Consequently, it can be difficult to achieve therapeutically useful blood levels of the proteins in patients. Conjugation of PEG to proteins has been described as an approach to overcoming these difficulties. Davis et al. in U.S. Pat. No. 4,179,337 disclose conjugating PEG to proteins such as enzymes and insulin to form PEG-protein conjugates having less immunogenicity yet which retain a substantial proportion of physiological activity. Veronese et al. (*Applied Biochem. and Biotech*, 11:141–152 (1985)) disclose activating polyethylene glycols with phenyl chloroformates to modify a ribonuclease and a superoxide dimutase. Katre et al., in U.S. Pat. Nos. 4,766,106 and 4,917,888, disclose solubilizing proteins by polymer conjugation. PEG and other polymers are conjugated to recombinant proteins to reduce immunogenicity and increase half-life. (Nitecki et al., U.S. Pat. No. 4,902,502; Enzon, Inc., PCT/US90/02133). Garman (U.S. Pat. No. 4,935,465) describes proteins modified with a water soluble polymer joined to the protein through a reversible linking group.

However, PEG-protein conjugates described to date suffer from several disadvantages. For example, modification of the protein with PEG often inactivates the protein so that the resulting conjugate has poor biological activity, particularly for proteins that bind to a receptor or act on a macromolecular substrate. One approach to overcoming this problem is to attach the PEG chains at specific sites in the protein, avoiding the binding site to leave it unhindered for interaction. Alternatively, in some cases, the protein binding site can be protected (Caliceti et al., *J. Bioactive Compat. Polym.*, 9:251 (1994)). However, these remedies are often difficult to implement. Typically, PEG in a PEG-protein conjugate is stably linked to the protein so that the beneficial properties provided by PEG remain. This in turn sometimes results in accumulation/vacuolization of conjugates that have difficulty to biodegrade (Bendele, A. et al., *Toxicol. Sci.*, 42:152 (1998)). Having a cleavable linkage between the polymer and protein would alleviate these shortcomings.

PEG has also been described for use in improving the blood circulation lifetime of liposomes (U.S. Pat. No. 5,103,556). Here, the PEG is covalently attached to the polar head group of a lipid in order to mask or shield the liposomes from being recognized and removed by the reticuloendothelial system. Liposomes having releasable PEG chains have also been described, where the PEG chain is released from the liposome upon exposure to a suitable stimulus, such as a change in pH (PCT/US97/18813) or thiolysis (Kirpotin, D. et al, *FEBS Letters*, 38:115 (1996)). However, release of the PEG chain from the liposome suffers from the drawback that the decomposition products are chemically modified and can have unpredictable, potentially negative effects in vivo.

SUMMARY OF THE INVENTION

Accordingly, it is an object of the invention to provide a conjugate having a ligand covalently yet reversibly linked to a hydrophilic polymer. The ligand is derived from an amine-, hydroxy- or carboxyl-containing compound. Upon cleavage of the linkage, the ligand in its native form is regenerated.

In one aspect, the invention includes a conjugate having the general structure I.

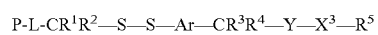

$$\text{P-L-CR}^1\text{R}^2\text{—S—S—Ar—CR}^3\text{R}^4\text{—Y—X}^3\text{—R}^5 \qquad \text{I}$$

wherein P is a hydrophilic polymer and L is a linker moiety; $R^1$, $R^2$, $R^3$ and $R^4$ are independently selected from the group consisting of H, alkyl, aralkyl and aryl; Ar is an aromatic group to which S—S and $CR^3R^4$ are linked in a configuration which promotes rapid cleavage of the $CR^3R^4$—Y bond, via a 1,4-, 1,6- or related elimination reaction involving the bonds of the aromatic group, following cleavage of the S—S bond; Y is a direct bond or —$X^1$—(C=$X^2$)—, where $X^1$ and $X^2$ are independently O or S; and $X^3R^5$ is a ligand derived from an amine-, hydroxy- or carboxyl-containing compound, such that $X^3$ is an oxygen or secondary or tertiary nitrogen atom.

In one embodiment, Ar is selected from (i) an aromatic hydrocarbon or a ring nitrogen-containing analog thereof, to which groups S—S and $CR^3R^4$ are linked in such a configuration that they are separated by an odd number of peripheral ring bonds; (ii) a 5-membered heteroaromatic ring selected from 2,4-imidazolyl, 2,4-thiazolyl, 2,4-oxazolyl, 2,5-pyrrolyl, 2,5-furanyl, and 2,5-thiophenyl; and (iii) a polycyclic aromatic group containing a 5-membered heteroaromatic ring, to which groups S—S and $CR^3R^4$ are linked in such a configuration that they are separated by a path containing an odd number of peripheral ring bonds, with the proviso that the path does not include an oxygen, sulfur, or trisubstituted nitrogen ring atom.

In one exemplary embodiment, Ar is selected from 1,2-phenyl, 1,4-phenyl, 1, 7-napthyl, 2,9-anthracyl, and 4,5-phenanthracyl.

In another embodiment, the linker moiety L is a direct bond, amine, amide, carbamate, ether, or a carbon chain, where the carbon chain may have one or more functional groups selected from amine, amide, carbamate, and ether, at either terminus of the chain or intervening between carbon atoms of the chain.

In yet another embodiment of the conjugate, Y is O(C=O), and the ligand is derived from an amine-containing compound.

In still another embodiment, $R^1$ is H and $R^2$ is selected from the group consisting of $CH_3$, $C_2H_5$ and $C_3H_7$. In other embodiment, $R^1$ and/or $R^2$ can be a polymer.

The ligand $X^3R^5$ in various embodiments is a polypeptide, an amine-containing drug, or an amine-containing lipid. When the ligand is an amine-containing lipid, it can be a phospholipid having a double hydrocarbon tail. When the ligand is a polypeptide, it can be a recombinant polypeptide. Exemplary polypeptides include cytokines. Specific exemplary polypeptides are interferons, interleukins, growth factors, erythropoietin, and enzymes.

In another embodiment, $R^1$ and $R^2$ is alkyl.

The hydrophilic polymer P is typically selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethylene glycol, polyaspartamide, copolymers thereof, and polyethylene oxide-polypropylene oxide. One preferred polymer is polyethylene glycol.

The conjugate, in another embodiment, contains multiple hydrophilic polymers attached to a polypeptide, each polymer attached by a linkage represented by L-CR$^1$R$^2$—S—S—Ar—CR$^3$R$^4$—Y in structure I. It will be appreciated that a polypeptide can have a mixed population of polymers, some attached by the releasable linkage of structure I and others by a stable, covalent linkage. In particular, the releasable linkages can be on or surrounding sites required for bioactivity.

In other embodiments, the hydrophilic polymer includes a targeting moiety at its free terminus.

In another aspect, the invention includes a composition comprising, in a pharmaceutically acceptable carrier, a conjugate obtainable by reaction of an amine-, hydroxy- or carboxyl-containing compound with a compound having the general structural formula:

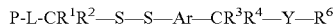

P-L-CR$^1$R$^2$—S—S—Ar—CR$^3$R$^4$—Y—R$^6$    II wherein P is a hydrophilic polymer and L is a linker moiety; $R^1$, $R^2$, $R^3$ and $R^4$ are independently selected from the group consisting of H, alkyl, aralkyl and aryl; Ar is an aromatic group to which S—S and CR$^3$R$^4$ are linked in a configuration which promotes rapid cleavage of the CR$^3$R$^4$—Y bond, via a 1,4-, 1,6- or related elimination reaction involving the bonds of the aromatic group, following cleavage of the S—S bond; Y is a direct bond or —X$^1$—(C=X$^2$)—, where X$^1$ and X$^2$ are independently O or S; and R$^6$ is a leaving group.

In one embodiment, Y is O(C=O) and R$^6$ is a hydroxy- or oxy-containing leaving group.

In other embodiments, the leaving group is derived from a compound selected from the group consisting of chloride, para-nitrophenol, ortho-nitrophenol, N-hydroxy-tetrahydrophthalimide, N-hydroxysuccinimide, N-hydroxy-glutarimide, N-hydroxynorbornene-2,3-dicarboxyimide, 1-hydroxybenzotriazole, 3-hydroxypyridine, 4-hydroxypyridine, 2-hydroxypyridine, 1-hydroxy-6-trifluoromethylbenzotriazole, immidazole, triazole, N-methyl-imidazole, pentafluorophenol, trifluorophenol and trichlorophenol.

The amine-containing compound, in various embodiments, is a phospholipid, a protein, or a drug, or a lipid.

In another embodiment, the composition containing the conjugate comprises a liposome. The liposome may further comprise, in some embodiments, an entrapped therapeutic agent.

In another aspect, the invention includes a liposome composition comprising vesicle-forming lipids and having a surface coating of hydrophilic polymers, wherein at least a portion of the lipids have the general structure:

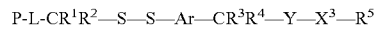

P-L-CR$^1$R$^2$—S—S—Ar—CR$^3$R$^4$—Y—X$^3$—R$^5$    I wherein P is a hydrophilic polymer and L is a linker moiety; $R^1$, $R^2$, $R^3$ and $R^4$ are independently selected from the group consisting of H, alkyl, aralkyl and aryl; Ar is an aromatic group to which S—S and CR$^3$R$^4$ are linked in a configuration which promotes rapid cleavage of the CR$^3$R$^4$—Y bond, via a 1,4-, 1,6- or related elimination reaction involving the bonds of the aromatic group, following cleavage of the S—S bond; Y is a direct bond or —X$^1$—(C=X$^2$)—, where X$^1$ and X$^2$ are independently O or S; and X$^3$R$^5$ is a ligand derived from an amine-, hydroxy- or carboxyl-containing compound, such that X$^3$ is an oxygen or secondary or tertiary nitrogen atom.

The liposomes, in one embodiment, further comprise an entrapped therapeutic agent.

In another embodiment, the liposomes further comprise vesicle-forming lipids stably linked to a hydrophilic polymer, wherein the total mole percent of lipids linked to a hydrophilic polymer is between 1% and about 20%. In another embodiment, hydrophilic polymers stably linked to vesicle-forming lipids are shorter than those contained in the conjugates of structure I.

In yet another embodiment, at least a portion of the hydrophilic polymers include a targeting moiety at the free terminus, e.g., distal end, of the polymer chain.

In yet another aspect, the invention includes a method for improving the blood circulation lifetime of liposomes having a surface coating of releasable hydrophilic polymer chains. The method includespreparing liposomes that include between about 1 to about 20 mole % of lipids conjugated to a hydrophilic polymer, wherein at least a portion of said conjugated lipids have the general structure I as represented above.

In still another aspect, the invention includes a polypeptide having a surface coating of hydrophilic polymer chains, wherein at least a portion of the polymer chains have the general structure I as represented above.

In one embodiment, $R^1$ of structure I is H and $R^2$ is $CH_3$, $C_2H_5$, or $C_3H_7$.

In a preferred embodiment, P is polyethylene glycol.

The polypeptide can be a natrually-occuring polypeptide isolated from a suitable source or a recombinant polypeptide. Exemplary polypeptides include the cytokines. Specific polypeptides are interferons, interleukins, growth factors, erythropoietin, and enzymes.

These and other objects and features of the invention will be more fully appreciated when the following detailed description of the invention is read in conjunction with the accompanying drawings.

BRIEF DESCRIPTION OF THE DRAWINGS

FIG. 18A is for mPEG$_{12000}$-MeDTB-erythropoietin with PEG/protein ratio of 6:1; FIG. 18B corresponds to mPEG$_{12000}$-erythropoietin at PEG/protein ratio of 8:1; FIG. 18C corresponds to mPEG$_{12000}$-MeDTB-erythropoietin with PEG/protein ratio of 9:1; FIG. 18D corresponds to mPEG$_{12000}$-erythropoietin at PEG/protein ratio of 12:1;

FIG. 19B shows the trace for the conjugate alone and FIG. 19B shows the trace for the conjugate after treatment with 5 mM cysteine;

DETAILED DESCRIPTION OF THE INVENTION

I. Definitions

Figure 1A:
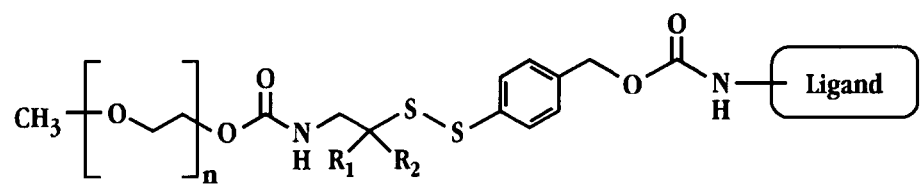
FIG. 1A shows an embodiment of the invention where dithiobenzyl (DTB) urethane links a methoxy-polyethyelene glycol (mPEG) moiety and an amine-containing ligand, where $R^1$ is a lower aryl, alkyl, aralkyl, e.g. $CH_3$, $C_2H_5$, Pr, or i-Pr, Bu, or H and $R^2$ is H or lower alkyl, aryl, or aralkyl.

"Polypeptide" as used herein refers to a polymer of alpha-amino acids and does not refer to a specific length of or amino acid sequence of a polymer. Thus, for example, the terms peptide, oligopeptide, protein, and enzyme are included within the definition of polypeptide. This term also includes post-expression modifications of the polypeptide, for example, glycosylations, acetylations, phosphorylations, and the like.

"Hydrophilic polymer" as used herein refers to a water-soluble, biocompatible polymer. Exemplary polymers of this type include polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers of the above-recited polymers, and polyethyleneoxide-polypropylene oxide copolymers. Properties and reactions with many of these polymers are described in U.S. Pat. Nos. 5,395,619 and 5,631,018.

"Polymer comprising a reactive functional group" or "polymer comprising a linkage for attachment" refers to a polymer that has been modified, typically but not necessarily, at a terminal end moiety for reaction with another compound to form a covalent linkage. Reaction schemes to functionalize a polymer to have such a reactive functional group or moiety are readily determined by those of skill in the art and/or have been described, for example in U.S. Pat. No. 5,613,018 or by Zalipsky et a., in for example, *Eur. Polymer. J.*, 19(12):1177–1183 (1983); *Bioconj. Chem.*, 4(4):296–299 (1993).

"Recombinant" as in "recombinant polypeptide" implies joining of alpha-amino acids through laboratory manipulation into a desired sequence.

"Alkyl" as used herein intends a group derived from an alkane by removal of a hydrogen atom from any carbon atom: "$C_nH_{2n+1}$". The groups derived by removal of a hydrogen atom from a terminal carbon atom of unbranched alkanes form a subclass of normal alkyl (n-alkyl) groups: H[CH$_2$]$_n$. The groups RCH$_2$—, R$_2$CH— (R not equal to H), and R$_3$C— (R not equal to H) are primary, secondary and tertiary alkyl groups respectively. "Lower alkyl" refers to alkyl groups having 1–6, and more preferably 1–4, carbon atoms.

"Aryl" refers to a substituted or unsubstituted monovalent aromatic radical having a single ring (e.g., phenyl), two condensed rings (e.g., naphthyl) or three condensed rings (e.g. anthracyl or phenanthryl). This term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl.

"Aralkyl" refers to a lower alkyl (preferably $C_1$–$C_4$, more preferably $C_1$–$C_2$) substituent which is further substituted with an aryl group; examples are benzyl and phenethyl.

An "aliphatic disulfide" linkage intends a linkage of the form $R^1$—S—S—R'', where R' and R'' are linear or branched alkyl chains that may be further substituted.

"Stably linked" refers to a linkage comprising functional groups which are appreciably more stable in vivo than the disulfide-based linkages described herein. Examples include, but are not limited to, amides, ethers, amines, and carbamates.

"Targeting moiety" intends a member that has binding affinity for a second member. Such members are also referred to in the art as targeting ligands or effector molecules. A preferred exemplary targeting moiety is a member that has binding affinity for a specific cell surface receptor on a target cell membrane or to a cell matrix. Another preferred exemplary targeting moieties are members having affinity for cells or pathogens circulating in the blood.

"Vesicle-forming lipids" refers to amphipathic lipids which have hydrophobic and polar head group moieties, and which can form spontaneously into bilayer vesicles in water, as exemplified by phospholipids, or are stably incorporated into lipid bilayers, with the hydrophobic moiety in contact with the interior, hydrophobic region of the bilayer membrane, and the polar head group moiety oriented toward the exterior, polar surface of the membrane. Such vesicle-forming lipids typically include one or two hydrophobic acyl hydrocarbon chains or a steroid group and may contain a chemically reactive group, such as an amine, acid, ester, aldehyde or alcohol, at the polar head group. Examples include phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14–22 carbon atoms in length, and have varying degrees of unsaturation. Other vesicle-forming lipids include glycolipids, such as cerebrosides and gangliosides, and sterols, such as cholesterol.

The following abbreviations are used herein: PEG, poly(ethylene glycol); mPEG, methoxy-PEG; DTB, dithiobenzyl; MeDTB, methyl-dithiobenzyl, EtDTB, ethyl-dithiobenzyl; DSPE, distearoyl phosphatidylethanolamine; DOPE, dioleoyl phosphatidylethanolamine; PHPC, partially hydrogenated phosphatidylcholine; MALDI-TOFMS, matrix-assisted laser desorption/ionization time-of-flight mass spectrometry.

II. The Conjugates of the Invention

In one aspect, the invention comprises a conjugate having the general structure I:

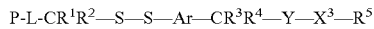

where:

P is a hydrophilic polymer and L is a linker moiety;

$R^1$, $R^2$, $R^3$ and $R^4$ are independently selected from the group consisting of H, alkyl, aralkyl and aryl;

Ar is an aryl group to which S—S and $CR^3R^4$ are linked in a configuration which promotes rapid cleavage of the Ar—$CR^3R^4$—Y moiety upon cleavage of the S—S bond, as described further below;

Y is —$X^1$—(C=$X^2$)— or a direct bond, where $X^1$ and $X^2$ are independently O or S; and $X^3R^5$ is a ligand derived from an amine-, hydroxy- or carboxyl-containing compound, such that $X^3$ is an oxygen or secondary or tertiary nitrogen atom.

The linker moiety L may be a direct bond, amine, amide, carbamate, ether, or a carbon chain, where the carbon chain may have one or more functional groups selected from amine, amide, carbamate, and ether, at either terminus of the chain or intervening between C atoms of the chain.

Ar is an aryl group to which S—S and $CR^3R^4$ are linked in a configuration which promotes rapid cleavage of the $CR^3R^4$—Y bond upon cleavage of the S—S bond. Such cleavage of the $CR^3R^4$—Y bond occurs via a 1,4-, 1,6-elimination reaction following S—S bond cleavage, as illustrated in FIG. 3A, FIG. 6B, FIG. 11B, and FIG. 20, or a related mechanism involving additional bonds of the aromatic system, as illustrated for a 1,7-naphthyl system in FIG. 3B.

In one embodiment, Ar is an aromatic hydrocarbon. Aromatic hydrocarbons include, for example, phenyl, to which the S—S and $CR^3R^4$ groups would be linked in a 1,2 (ortho) or 1,4 (para) configuration, as well as bicyclic (naphthalene), tricyclic (e.g. phenanthrene, anthracene) or higher aromatic hydrocarbons. The above noted groups are linked to the hydrocarbon in an ortho (1,2) or para (1,4) configuration, or they are otherwise in such a configuration that they are separated by an odd number of peripheral ring bonds. Examples of the latter case include, but are not limited to, 1,7-naphthyl, 1,5-anthracyl, 1,7-anthracyl, 1,10-anthracyl, 1,6-phenanthryl, 3,6-phenanthryl, and 4,10-phenanthryl. These designations employ the conventional numbering systems illustrated below.

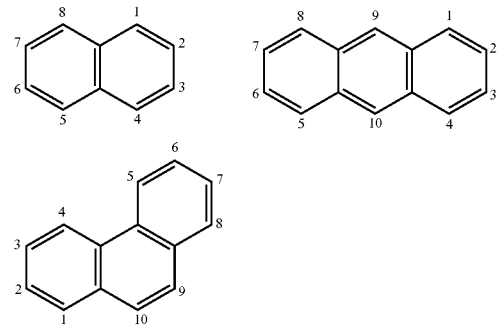

Also included in the definition of Ar are the corresponding 6-, 10-, or 14-membered heteroaromatic rings, where one or more non-fusion ring atoms (i.e. those numbered in the structures above), to which the above groups S—S and $CR^3R^4$ are not attached, are replaced with nitrogen. Again, the above noted groups are in an ortho or para configuration, or they are otherwise in such a configuration that they are separated by an odd number of peripheral ring bonds.

Also included in the definition of Ar are 5-membered heteroaromatic rings, where one or more ring atoms (to which the above noted groups S—S and $CR^3R^4$ are not attached) are replaced with nitrogen, oxygen, or sulfur. Preferred monocyclic systems include 2,4-imidazole, -thiazole, and -oxazole and 2,5-pyrrole, -furan, and -thiophene. Also included are fused counterparts, i.e. polycyclic aromatic groups containing such a 5-membered heteroaromatic ring. In this case, the above noted groups (S—S and $CR^3R^4$) are preferably in an ortho or para configuration, or they are otherwise in such a configuration that they are separated by an odd number of peripheral ring bonds. An exception in this case is that the path along the periphery containing the odd number of bonds does not contain an oxygen, sulfur, or trisubstituted nitrogen (e.g., as in indole) ring atom. Examples include, but are not limited to, 2,6- or 2,7-benzimidazole, -benzthiazole, and -benzoxazole, 2,4- or 2,6-indole, and analogs in which one or more non-fusing carbon atoms on a 6-ring are replaced with nitrogen.

$R^1$–$R^4$ are independently selected to be H, alkyl, aralkyl, or aryl, and, as will be seen, $R^1$ and $R^2$ can be varied to tailor the rate of disulfide cleavage. For example, to achieve a faster rate of cleavage, $R^1$ and $R^2$ are hydrogens. A slower rate of cleavage is achieved by sterically hindering the disulfide by selecting an alkyl, aralkyl or aryl group for one or both of $R^1$ and $R^2$. Preferably, $R^1$–$R^4$ are independently selected from hydrogen and lower ($C_h$ to $C_6$) alkyl. More preferably, $R^1$ and $R^2$ are hydrogen or $C_1$-$C_4$ alkyl, and $R^3$ and $R^4$ are hydrogen. In one embodiment, $R^1$ is hydrogen and $R^2$ is $C_1$-$C_4$ alkyl.

Y is a linking moiety, which may be a direct bond or $X^1$ (C=$X^2$), where $X^1$ and $X^2$ are independently O or S. It is joined to a ligand represented by $X^3R^5$, where $X^3$ is an oxygen or secondary or tertiary nitrogen atom. The ligand is derived from an amine-, hydroxy- or carboxyl-containing compound (e.g., $R^5NH_2$, $R^5OH$, or $R^5COOH$). Examples of drugs containing such groups include mitomycin C (amine containing), paclitaxel (Taxol®; (hydroxyl containing) and chlorambucil (carboxyl-containing). The ligand can be derived from any number of substrates, including, but not limited to, lipids, drugs, polypeptides, viruses, surfaces of biomaterials, and aminoglycosides. In preferred embodiments, the ligand compound is a primary or secondary amine-containing lipid, drug or polypeptide.

Figure 20A:
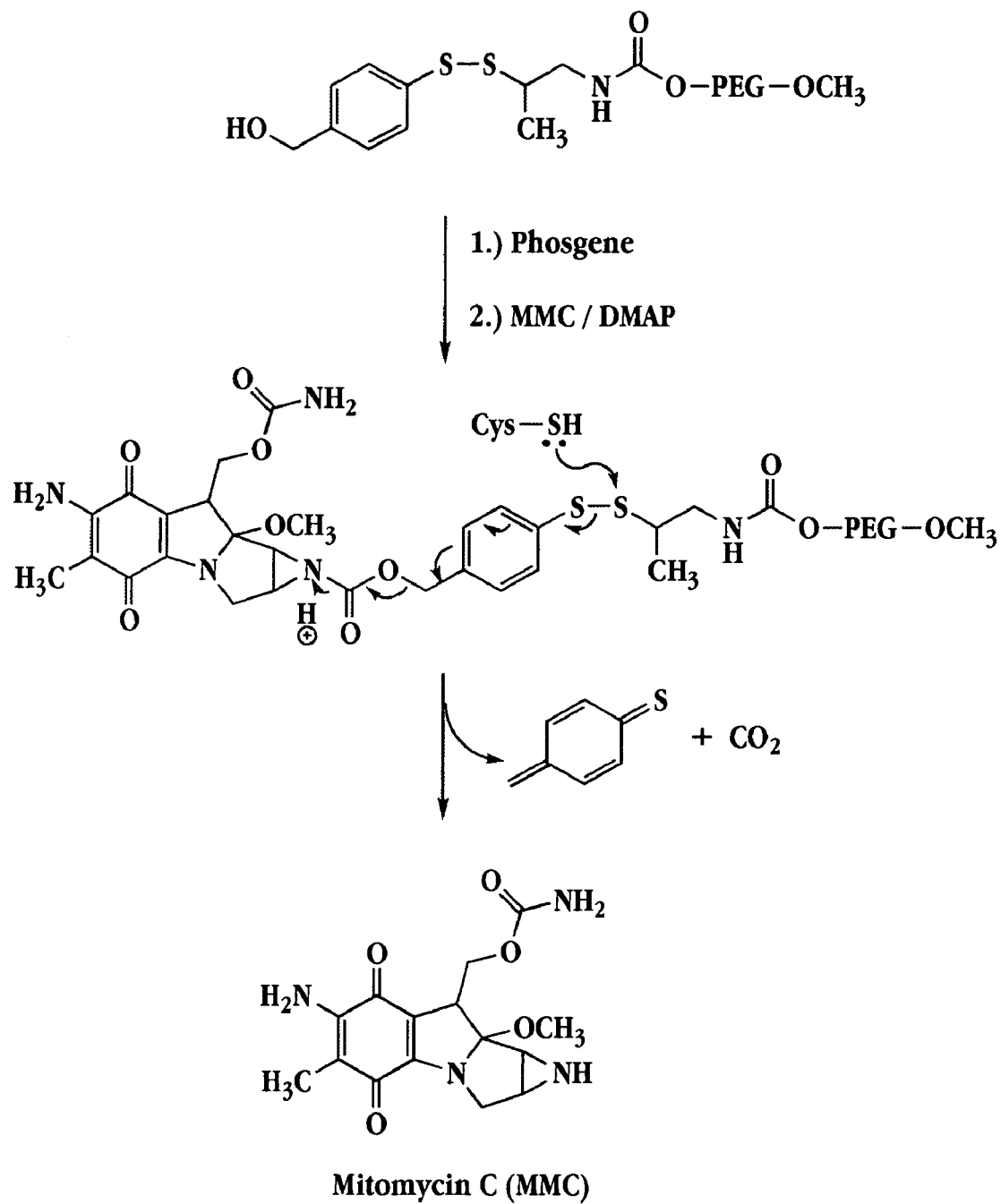
FIGS. 20A–20D show exemplary synthesis and thiolytic cleavage of mPEG-DTB-drug conjugates, where the mPEG-DTB is linked as urethane to an amino group of mitomycin C (FIG. 20A), as alkyl to N-4 position of 5-fluorouracil (FIG. 20B), as carbonate to 2' hydroxy moiety of paclitaxel (FIG. 20C), or as ester to a carboxyl group of chlorambucil (FIG. 20D)
Figure 20B:
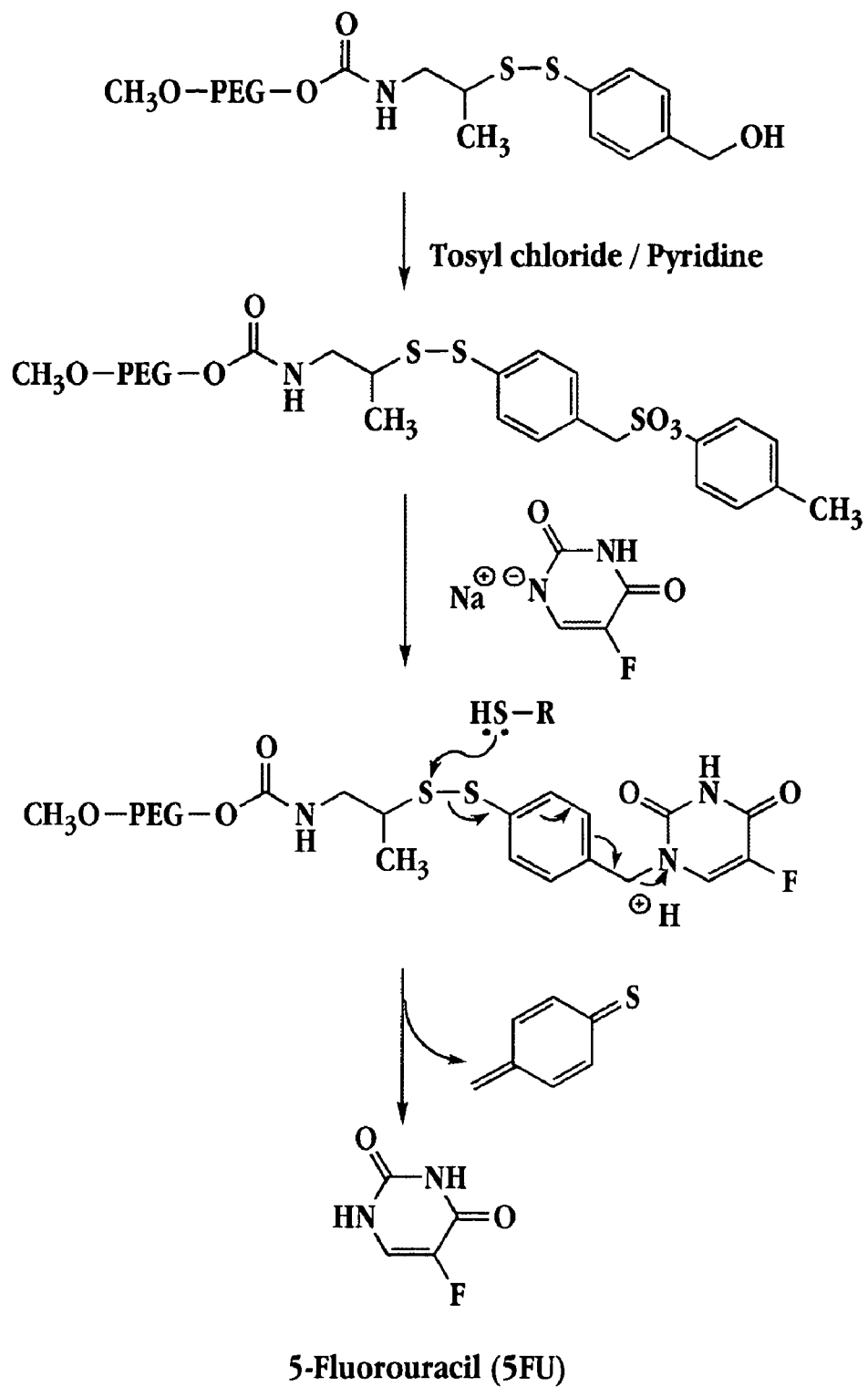

When the ligand is derived from an amine- or hydroxy-containing compound, Y is preferably —$X^1$—(C=$X^2$)— as recited above, and more preferably O(C=O), such that the conjugate contains a carbamate or carbonate linkage, respectively, to the ligand. Y can also be a direct attachment, thus conjugating via an ether linkage with $X^3$=O, or via a C—N linkage as shown in FIG. 20B (discussed below) for $X^3$=N. When the ligand is derived from a carboxyl-containing compound, Y is preferably a direct bond, such that the compound is directly linked to $CR^3R^4$ via the carboxyl group; i.e. an ester linkage. In all of these embodiments, the polymer-SS—Ar—$CR^3R^4$-drug conjugate, after administration in vivo, thiolytically decomposes to regenerate the drug in its native, active form. Note that while disulfide-substituted benzyl urethane (carbamate) is hydrolysis resistant under in vivo conditions, carbonate and esters might slowly hydrolyze and thus release the ligand portion of the conjugate. In this respect, the DTB urethane is preferable to the other two linkages, due to its purely thiolytic release mechanism.

Also provided are compositions containing a conjugate as described above and a pharmaceutically-acceptable carrier, such as saline, buffer or the like.

FIG. 1A shows the structure of an exemplary conjugate in accord with the invention, where $R^1$ is the hydrophilic polymer methoxy-polyetheylene glycol (mPEG), represented by the formula $CH_3O(CH_2CH_2O)_n$ where n is from about 10 to about 2300, which corresponds to molecular weights of about 440 Daltons to about 100,000 Daltons. The mPEG in this embodiment includes a urethane linking moiety. The selection of the molecular weight of the polymer depends to some extent on the selection of the attached ligand. In embodiments where the ligand is derived from an amine-containing lipid, for use in a liposome, a preferred range of PEG molecular weight is from about 750 to about 10,000 Daltons, more preferably from about 2,000 to about 5,000 Daltons. In embodiments where the ligand is derived from an amine-containing polypeptide, e.g., a protein, a preferred range of PEG molecular weight is from about 2,000 to about 40,000 Daltons, more preferably from about 5,000 to about 20,000 Daltons. It will be appreciated that P can be selected from a variety of hydrophilic polymers, and exemplary polymers are recited above.

The hydrophilic polymer may also have a targeting moiety attached to its free terminus. Such targeting moieties include the molecules described in U.S. Pat. No. 5,891,468, and this section beginning at Col. 11, line 25 to Col. 16, line 13 is incorporated by reference herein. Other exemplary moieties are set forth in U.S. Pat. No. 6,043,094 and Col. 8, line 55 to Col. 13, line 30 are incorporated herein by reference. Exemplary targeting moieties include folate; growth factors, such as transferrin, vascular endothelial growth factor (VEGF), epidermal growth factor (EGF), fibroblast growth factor (FGF); antibodies of fragments thereof specific to various epitopes, e.g, her2; cytokines, CD4; and the like. It is contemplated that some targeting moieties will facilitate cell internalization. In these cases, the relatively higher intracellular glutathione concentration facilitates rapid DTB cleavage and release of the attached drug or protein.

For some ligands, such as polypeptide ligands, which have a variety of functional side groups, multiple polymers P can be conjugated to the ligand. They may be conjugated via the structure shown above (i.e, the moiety $L_{CR}{}^1R^2$—S—S—Ar—$CR^3R^4$—Y) or by a linkage which is more stable in vivo, or by a combination of linkages. The selection of the molecular weight of the polymers may depend on the number of polymer chains attached to the ligand, where a larger molecular weight polymer is often selected when the number of attached polymer chains is small, and vice versa.

With continuing reference to FIG. 1A, $R^1$ and $R^2$ in this exemplary conjugate are H; however, either or both of $R^1$ and $R^2$ can also be straight chain or branched alkyl, an aralkyl group, or an aryl group. In a preferred embodiment, $R^1$ is H and $R^2$ is an alkyl, and several examples are given below. In the conjugate shown in FIG. 1A, Y—$X^3R^5$ takes the general form of O(C=O)—(NH—ligand), where NH-ligand can be any amine-containing polypeptide, drug or lipid. Specific examples of each embodiment are given below. The moiety Y—$X^3R^5$ can also be of the form O(C=S)—(NH-ligand) or S(C=O)—(NH-ligand).

Figure 1B:
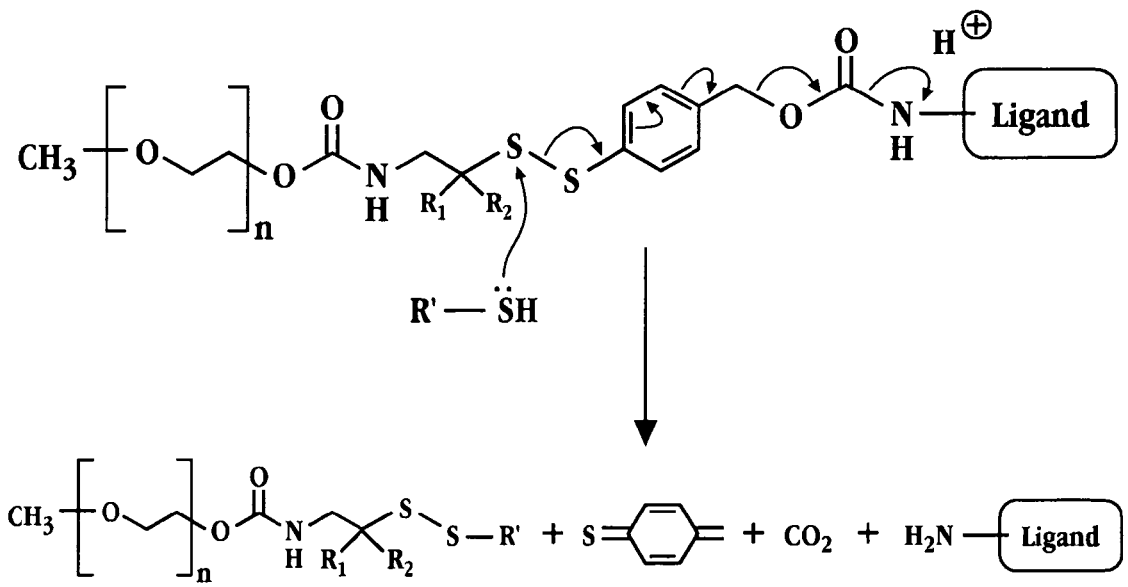
FIG. 1B shows the products after thiolytic cleavage of the conjugate in FIG. 1A.

FIG. 1B shows the mechanism of thiolytic cleavage of the mPEG-DTB-(NH-ligand) conjugate of FIG. 1A. The ortho- or para-dithiobenzyl carbamate moiety is cleavable under mild thiolytic conditions, such as in the presence of cysteine, glutathione, albumine, or other naturally-occurring reducing agents. Upon cleavage, the amine-containing ligand compound is regenerated in its natural, unmodified form (Senter, P. et al., *J. Org. Chem.*, 55(9):2975 (1990), Zalipsky, S. *Bioconjugate Chem.*, 10:703 (1999)). Studies in support of the invention, described below, show that natural, physiologic conditions in vivo are sufficient to initiate and achieve cleavage of the DTB linkage. It will be appreciated that a reducing agent can also be administered to artificially induce thiolytic conditions sufficient for cleavage and decomposition of the conjugate.

In preferred embodiments, the ligand compound comprises an amine-containing polypeptide, drug or lipid. Examples of these embodiments will now be described.

A. Amine-Containing Lipid Conjugates

In one embodiment, the amine-containing ligand compound is an amine-containing lipid. Lipids as referred to herein intend water-insoluble molecules having at least one acyl chain containing at least about eight carbon atoms, more preferably an acyl chain containing between about 8–24 carbon atoms. A preferred lipid is a lipid having an amine-containing polar head group and an alkyl chain, such as stearoylamine. Exemplary lipids are phospholipids having a single acyl chain, or two acyl chains. Preferred phospholipids with an amine-containing head group include phosphatidylethanolamine and phosphatidylserine. The lipid tail(s) preferably have between about 12 to about 24 carbon atoms and can be fully saturated or partially unsaturated. One preferred lipid is distearoylphosphatidylethanolamine (DSPE); however, those of skill in the art will appreciate the wide variety of lipids that fall within this description. It will also be appreciated that the lipid can naturally include an amine group or can be derivatized to include an amine group (see for example FIGS. 6A–6B). Other hydrophobic moieties that do not have an acyl tail, such as cholesterolamine, are also suitable.

A1. Synthesis

Figure 2:
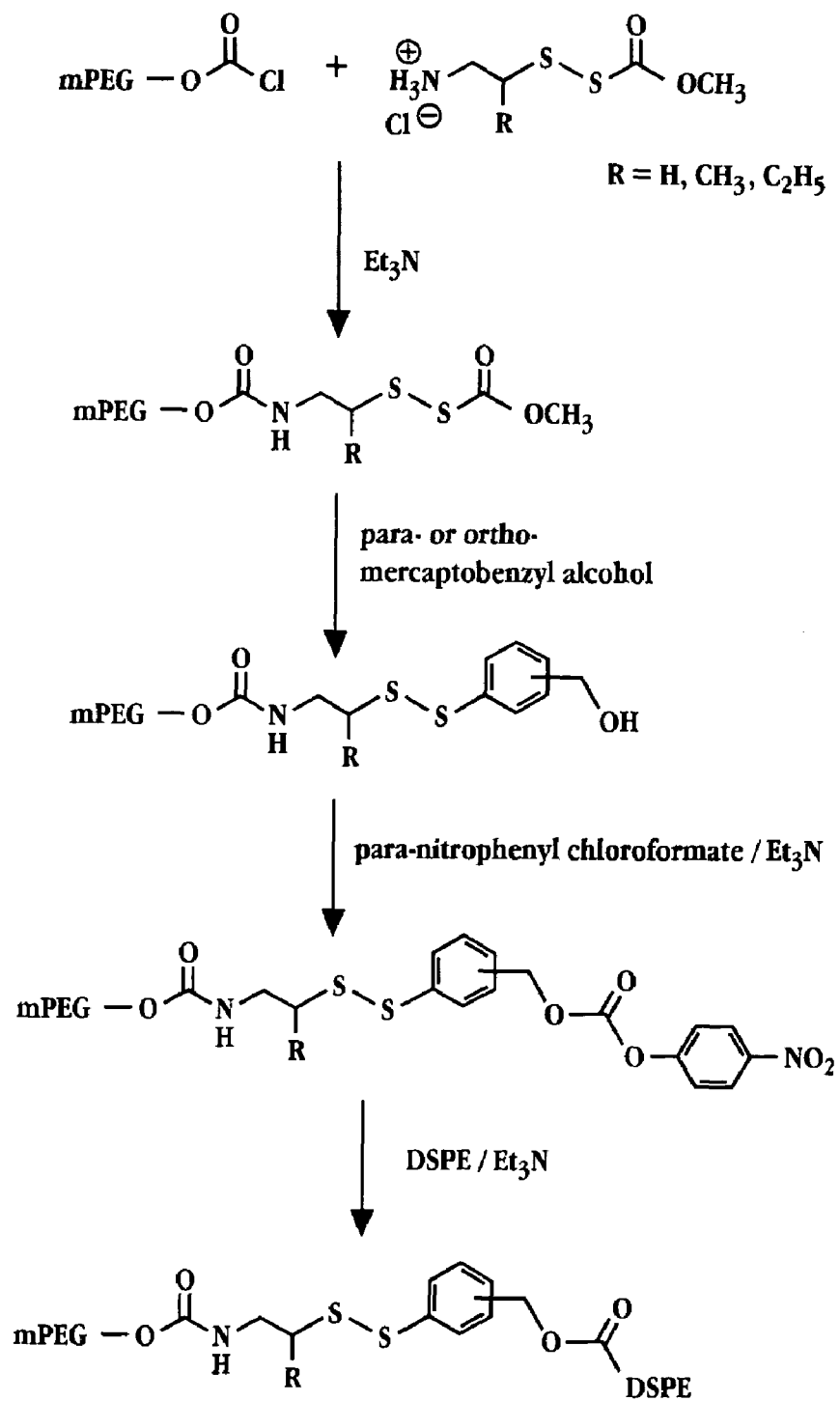
FIG. 2 illustrates a synthetic reaction scheme for synthesis of an mPEG-DTB-amine-lipid conjugate, where the amine-lipid is distearoyl-phosphatidyl-ethanolamine (DSPE)

The synthesis of a polymer-DTB-lipid conjugate is schematically depicted in FIG. 2. mPEG derivatives (MW 2000 and 5000 Daltons) having a methoxycarbonyldithio end group were prepared by reacting 2-(methoxycarbonyidithio) ethaneamine with mPEG-chloroformate, which was readily prepared by phosgenation of dried mPEG-OH solution (Zalipsky, S. et al., *Biotechnol. Appl. Biochem.* 15:100–114 (1992)). The former compound was obtained through 2-aminoethanethiol hydrochloride reaction with an equivalent amount of methoxycarbonylsulfenyl chloride, according to published procedures (Brois, S. J. et al., *J. Amer. Chem. Soc.* 92:7629–7631 (1970); Koneko, T. et al., *Bioconjugate Chem.* 2:133–141 (1991)). Both the para and ortho isomers of mercaptobenzyl alcohol (Grice, R. et al., *J. Chem. Soc.* 1947–1954 (1963)) coupled cleanly with the resulting PEG-linked acyl disulfide (alternative name PEG-S-sulfenycarbomethoxy (Scm)), yielding mPEG bearing a dithio benzyl alcohol end group. Active carbonate introduction proceeded as with underivatized mPEG-OH, to give the para-nitrophenyl carbonate (mPEG-DTB-NPC). Addition of DSPE in chloroform in the presence of triethylamine (TEA) formed the desired mPEG-DTB-DSPE product. Both ortho- and para-DTB-lipid conjugates were prepared and purified by silica gel chromatography and characterized by NMR and MALDI-TOF MS, the details of which are given in Example 1.

Aromatic compounds analogous to mercapto benzyl alcohol, e.g. 1-mercapto-2-naphthalenemethanol, 2-mercapto-1-naphthalenemethanol, 3-mercapto-2-naphthalenemethanol, and 5-mercapto-1-naphthalenemethanol, can be purchased or prepared by standard methods of organic synthesis (see e.g. H. Meier et al., *Synthesis* 3:327–9 (1996), *Liebigs Ann.* 12:2221–6 (1995), and *Tetrahedron Lett.* 35(14):21614 (1994); A. H. Weinstein, *J. Org. Chem.* 24:1609–10 (1959)). Compounds having additional aromatic-ring substitutions, e.g., methyl or methoxy substitution on the aromatic ring, may also be used.

Figure 3A:
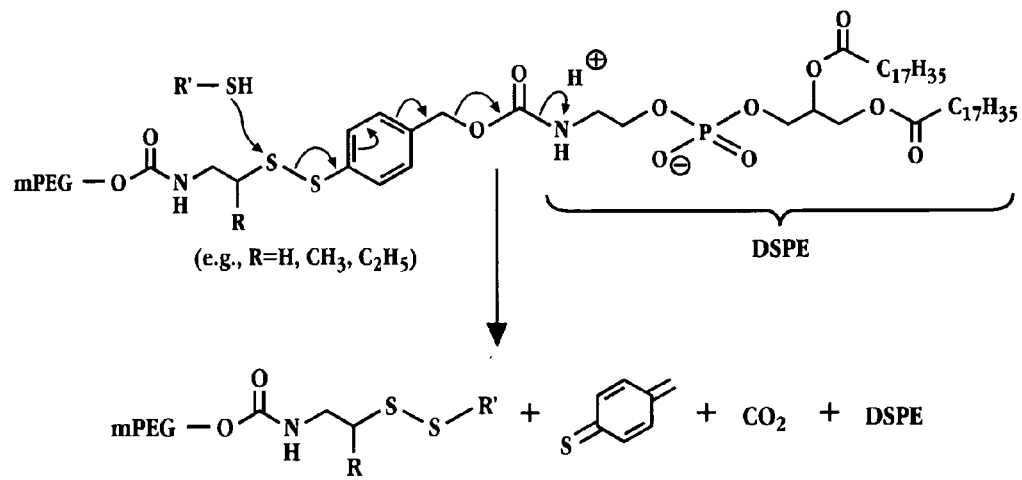
FIG. 3A illustrates the thiolytic cleavage mechanism of a para-dithiobenzyl urethane linked mPEG-DSPE conjugate.
Figure 3B:
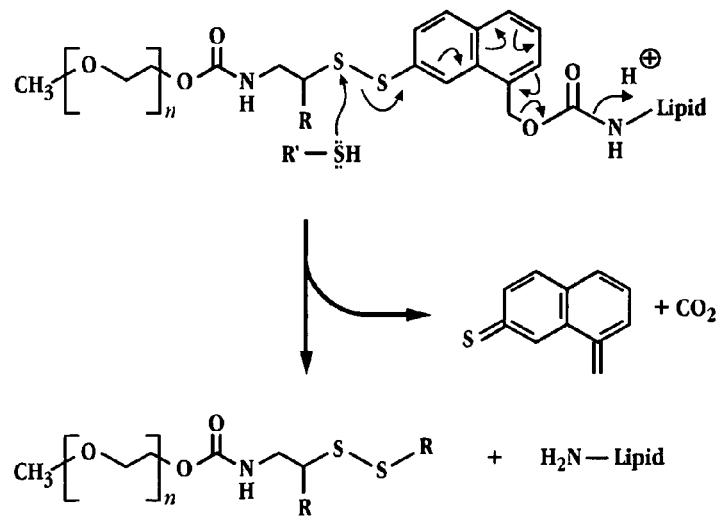
FIG. 3B illustrates the thiolytic cleavage of an mPEG-DSPE conjugate having a 1-dithio-7-(carbamoyl methyl) naphthyl linkage.

FIG. 3A shows the mechanism of thiolytic cleavage of the above-described mPEG-DTB-DSPE conjugate, involving initial scission of the disulfide followed by 1,6-elimination and decarboxylation. Upon cleavage, the phosphatidylethanolamine lipid is regenerated in its natural, unmodified form. An example of analogous liberation of amino lipid from a 1,7-napthyl substituted linker is shown in FIG. 3B.

Figure 4A:
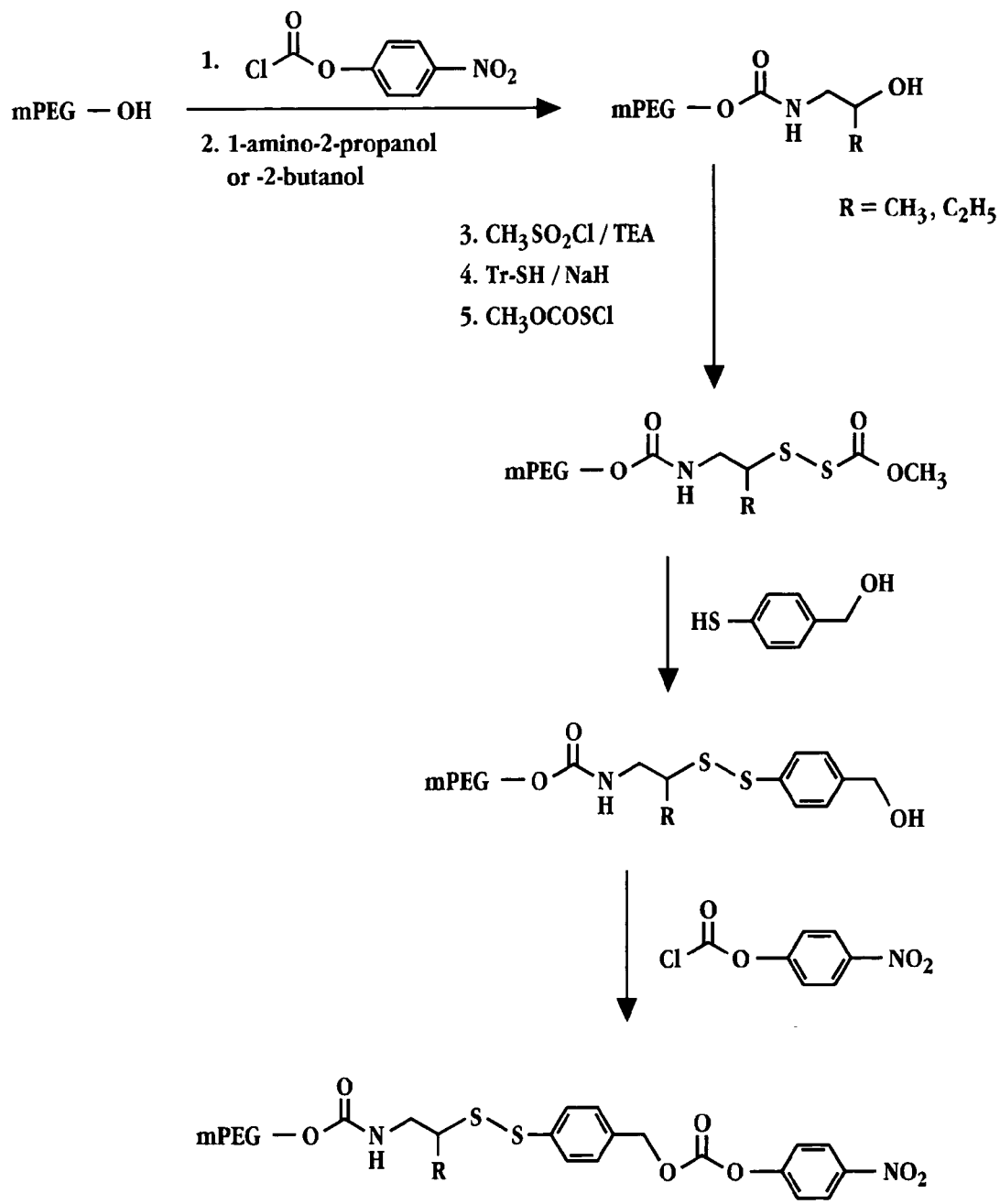
FIGS. 4A–4B show synthetic reaction schemes for preparation of an mPEG-DTB-NPC (nitrophenylcarbonate) reagent (FIG. 4A) and mPEG-DTB-DSPE conjugate where the DTB linkage is sterically hindered by an alkyl group R.
Figure 4B:
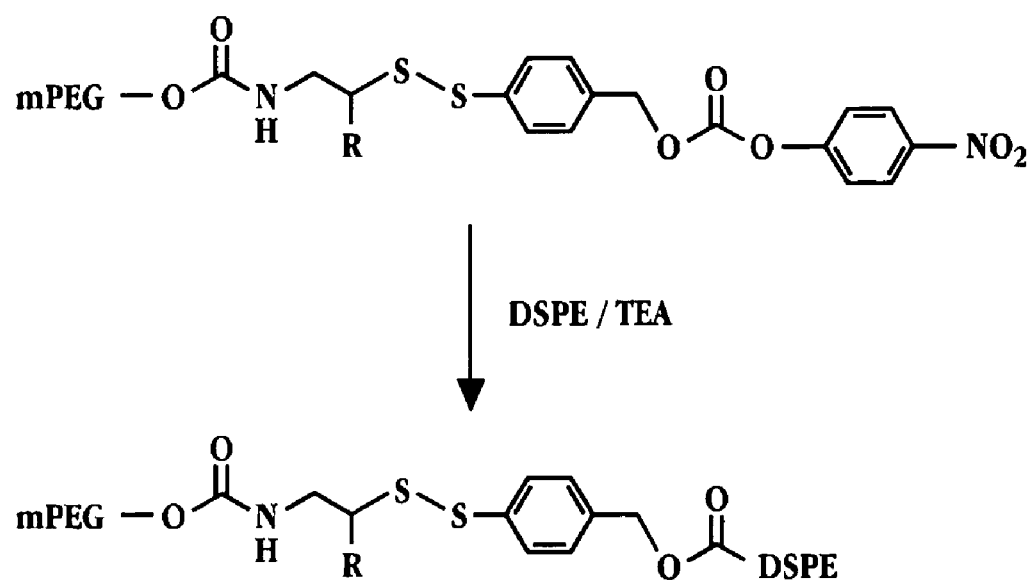

FIGS. 4A–4B show a reaction scheme for synthesis of mPEG-DTB-DSPE conjugates having an alkyl group adjacent the disulfide linkage, i.e., a more hindered disulfide linkage. As described more fully in Example 2A, mPEG-OH in dichloromethane was reacted with p-nitrophenylchloroformate in the presence of triethylamine (TEA) to form mPEG-nitrophenyl carbonate (Veronese, F. et al., *Appl. Biochem. Biotechnol.*, 11:141 (1985)). An amino alcohol, such as 1-amino-2-propanol or 1-amino-2-butanol, in dimethylformamide (DMF) was reacted with the mPEG-nitrophenyl carbonate in the presence of TEA to form a secondary alcohol attached to PEG. The secondary alcohol was then converted to the desired mPEG-DTB-DSPE conjugate as illustrated in FIG. 4A and detailed in Example 2A.

In the reaction scheme illustrated in FIG. 4B, mPEG-α-R-dithiobenzyl nitrophenyl carbonate (R=methyl (Me), ethyl (Et), isopropyl, etc.) was reacted with DSPE to form the desired lipopolymer mPEG-R-DTB-NPC. The nitrophenyl moiety in the mPEG-α-R-dithiobenzyl-nitrophenyl carbonate compound acts as a leaving group to yield the desired product upon reaction with an amino lipid.

Example 2C describes preparation of an mPEG-EtDTB-lipid conjugate where the disulfide linkage is hindered by an ethyl moiety on the α-carbon.

Figure 5:
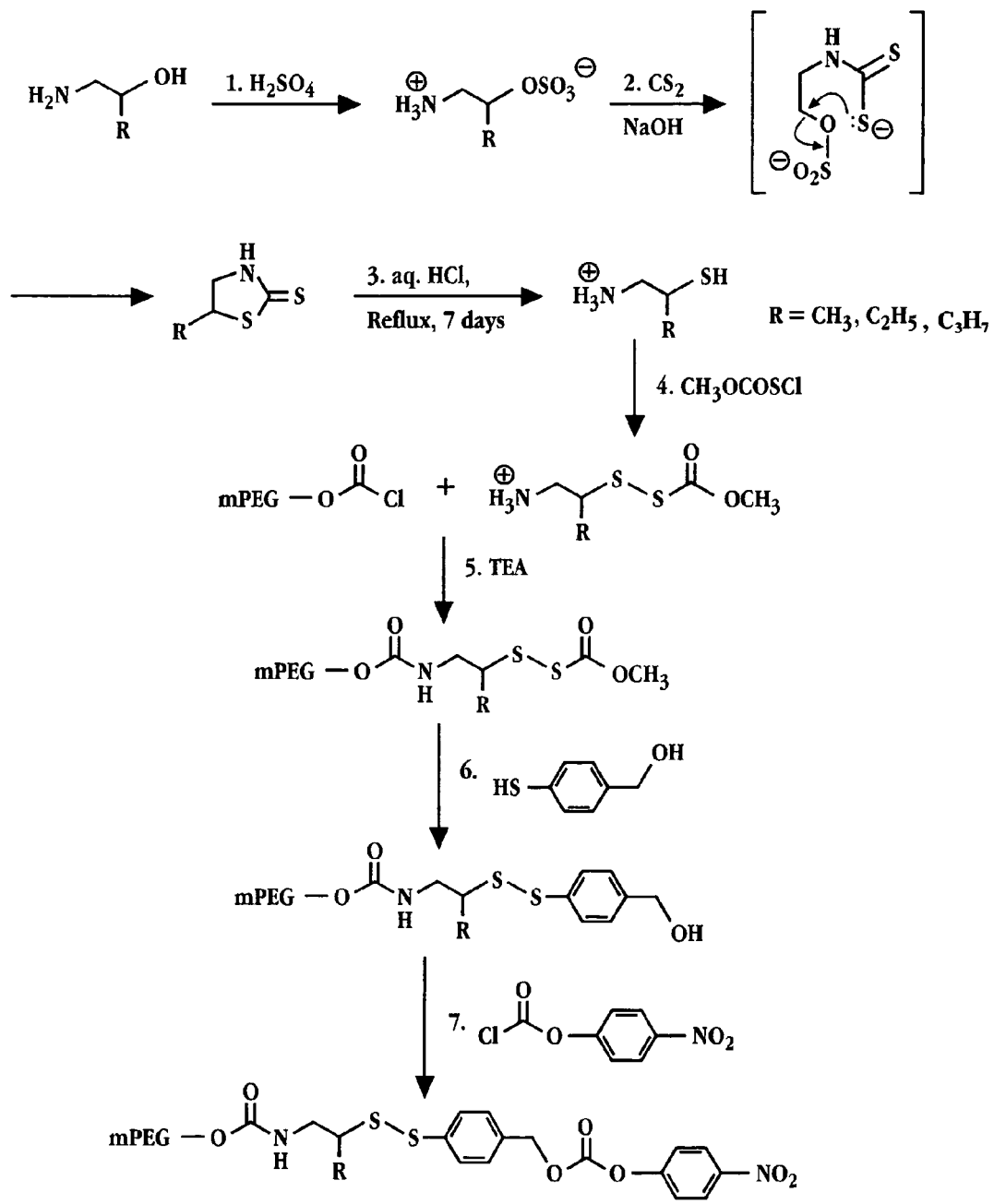
FIG. 5 shows another synthetic reaction scheme for preparation of mPEG-DTB-NPC for conjugation with amino-containing ligands in accord with the invention.

FIG. 5 shows another synthetic reaction scheme for preparation of a-carbon substituted mPEG-DTB-NPC reagents in accord with the invention. The details of the reaction procedures are given in Examples 3A–3B. In these examples, R-substituted aminoethanols were first converted into the corresponding aminoethanethiols, and then to the mPEG-S-Scm derivatives. The latter, as illustrated above in FIG. 2 and FIG. 4A, are easily converted into mPEG-DTB-NPC.

Figure 6A:
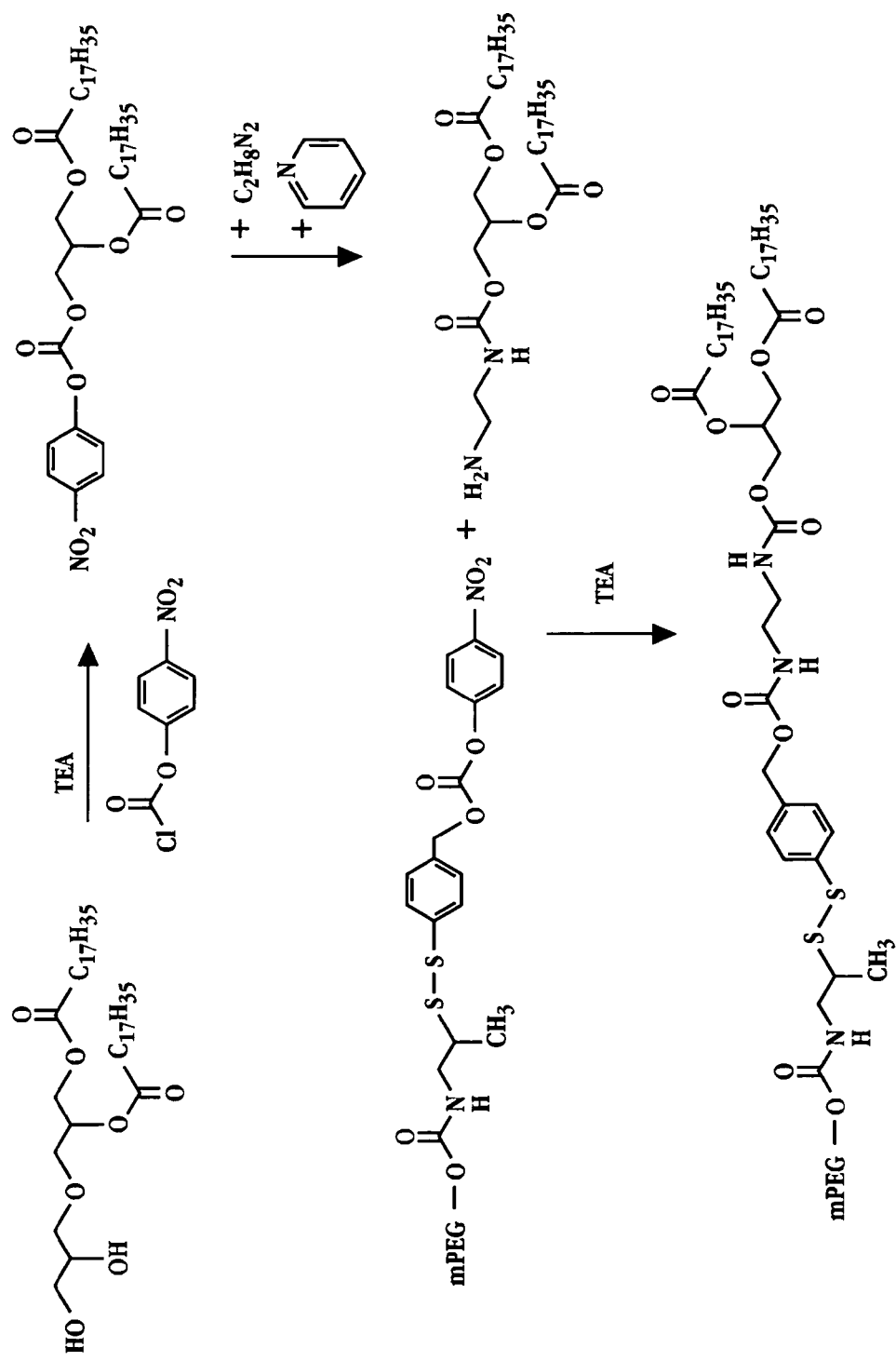
FIG. 6A is a synthetic reaction scheme for synthesis of an mPEG-DTB-lipid conjugate which upon thiolytic cleavage yields a cationic lipid (as illustrated in FIG. 6B)
Figure 6B:
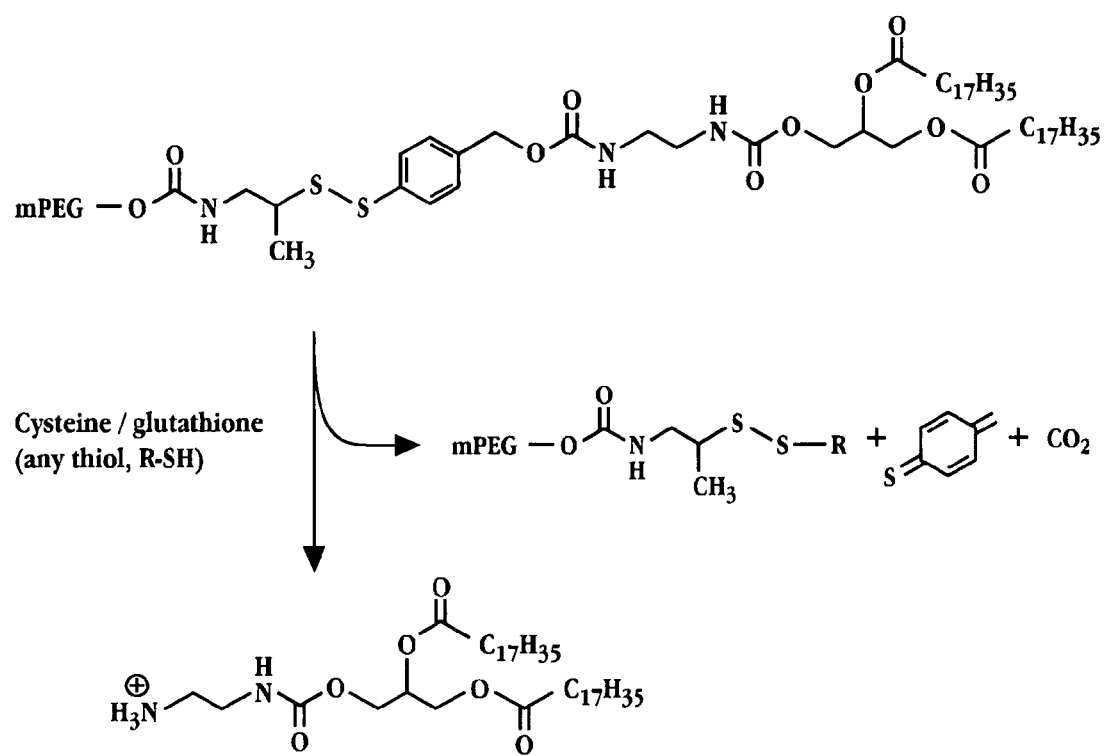
FIG. 6B shows the products after thiolytic cleavage of the conjugate in FIG. 6A.
Figure 6C:
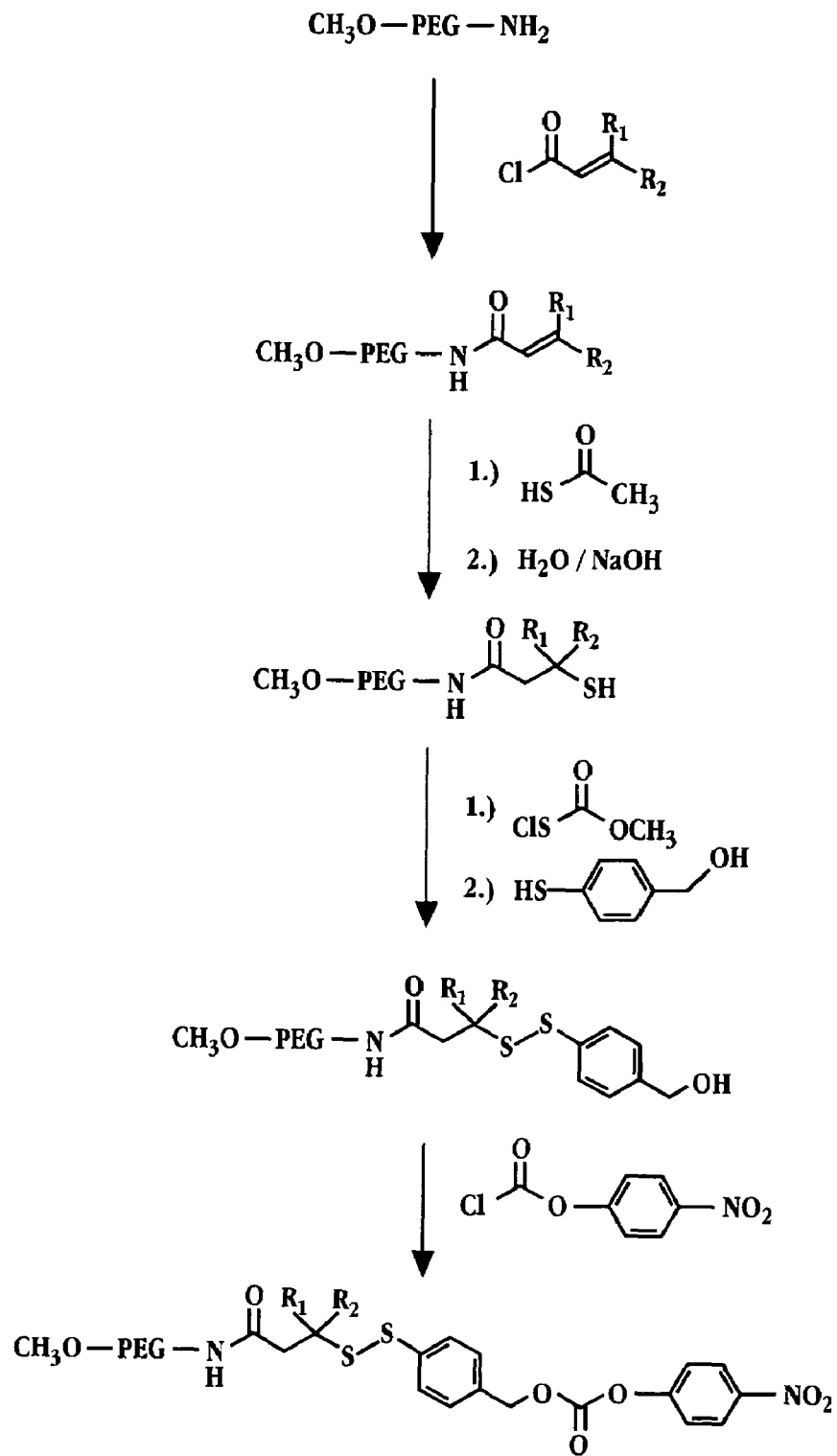
FIG. 6C shows an alternative reaction scheme for synthesis of a disulfide-hindered mPEG-DTB-NPC reagent.

FIG. 6A shows a reaction scheme for preparation of another mPEG-DTB-lipid conjugate in accord with the invention. The reaction details are provided in Example 4. The lipid 1,2-distearoyl-sn-glycerol derivatized with an amino group and then coupled with mPEG-DTB-nitrophenyl, prepared as described in FIG. 4A or FIG. 5. The resulting mPEG-DTB-lipid differs from the conjugates described above in the absence of a phosphate head group. The mPEG-DTB-lipid of FIG. 6A is a neutral, uncharged lipopolymer. As shown in FIG. 6B, upon thiolytic reduction of the disulfide bond, the conjugate decomposes to yield a cationic lipid. The positively-charged lipid provides for electrostatic interaction with biological cells and commensurate advantages in in vivo targeting (see, for example, WO 03/053409). An alternative method to make hindered mPEG-DTB-NPC linker is shown in FIG. 6C.

In the reaction schemes described above, $R^1$ of the claimed conjugate is H. However, in other embodiments $R^1$ is an alkyl, aralkyl or aryl moiety. In this approach, for example, where $R^1$ and $R^2$ are both $CH_3$, an α,β-unsaturated acyl chloride (R'R"C=CHCOCl, where R' is, for example $CH_3$ and R" is $CH_3$, however any alkyl or aryl is contemplated) is reacted with an amine-terminated PEG to give the corresponding N-PEG-substituted α,β-unsaturated amide, as shown in FIG. 6C. This compound is reacted with thiolacetic acid, giving the corresponding N-PEG-substituted β-(acetylthio) amide via addition to the C=C bond (Worrell, N. R. et al., *Anti-Cancer Drug Design*, 1:179 (1986); Greenfield, L. et al., *Bioconjugate Chem.*, 1:400 (1990)). The acetylthio group (—$SCOCH_3$) is hydrolyzed to a thiol group (—SH), which is then reacted with methoxycarbonyl (sulfenyl)chloride ($ClSCOOCH_3$), generating the S-Scm end group (—$SSCOOCH_3$). The mPEG-S-Scm, as in the examples above, is then reacted with p-mercapto benzyl alcohol to provide for PEG-linked DTB-alcohol (having the structure PEG-NH—CO—$CH_2CR'R"$—SS-p-phenyl-$CH_2OH$). The benzyl alcohol moiety is then reacted with nitrophenyl chloroformate as in previous examples to give the nitrophenyl carbonate, which is a convenient reactive group for linking amino-containing ligands.

Pertinent to the above syntheses, the invention also includes a composition comprising a conjugate obtainable by reaction of an amine-, hydroxy- or carboxyl-containing compound with a compound having the general structural formula II:

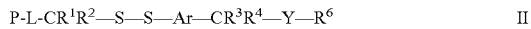

P-L-CR$^1$R$^2$—S—S—Ar—CR$^3$R$^4$—Y—R$^6$    II wherein P is a hydrophilic polymer and L is a linker moiety, as described above;

R$^1$, R$^2$, R$^3$ and R$^4$ are independently selected from the group consisting of H, alkyl, aralkyl, and aryl;

Ar is an aryl group to which S—S and CR$^3$R$^4$ are linked in a configuration which promotes rapid cleavage of the Ar—CR$^3$R$^4$—Y moiety upon cleavage of the S—S bond, as described above;

Y is a direct bond or —X$^1$—(C═X$^2$)—, where X$^1$ and X$^2$ are independently O or S; and R$^6$ is a leaving group.

The leaving group is displaced upon reaction with an amine-, hydroxy- or carboxyl-containing ligand compound, such as DSPE, a polypeptide, or an amine-containing drug. The leaving group is selected according to the reactivity of the displacing group in the ligand compound, and is preferably derived from various acidic alcohols that have a hydroxy- or oxy-containing leaving group. These include chloride, p-nitrophenol, o-nitrophenol, N-hydroxy-tetrahydrophthalimide, N-hydroxysuccinimide, N-hydroxy-glutarimide, N-hydroxynorbornene-2,3-dicarboxyimide, 1-hydroxybenzotriazole, 3-hydroxypyridine, 4-hydroxypyridine, 2-hydroxypyridine, 1-hydroxy6-trifluoromethylbenzotriazole, immidazole, triazole, N-methyl-imidazole, pentafluorophenol, trifluorophenol and trichlorophenol.

When the compound of formula 11 is reacted with an amine- or hydroxy-containing compound that displaces R$^6$ to form a conjugate, such as represented by formula I above, Y is preferably —X$^1$—(C═X$^2$)— as recited above, and more preferably O(C═O), such that the resulting conjugate contains a carbamate or carbonate linkage, respectively, to the ligand. See, for example, FIG. 20A, 20C and Examples 10A–10B.

When the compound of formula II is reacted with a carboxyl-containing compound, e.g. chlorambucil, Y is preferably a direct bond, such that the compound is directly linked to CR$^3$R$^4$ via the carboxyl group; i.e. an ester linkage. In the exemplary case of chlorambucil, the conjugate of formula I above would have the formula:

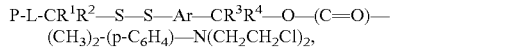

P-L-CR$^1$R$^2$—S—S—Ar—CR$^3$R$^4$—O—(C═O)—
(CH$_3$)$_2$-(p-C$_6$H$_4$)—N(CH$_2$CH$_2$Cl)$_2$, where, in accordance with the definition of formula I above, Y is a direct bond, and X$^3$ is the ester oxygen of chlorambucil. See FIG. 20D. The conjugate could also be formed by condensing an activated derivative of chlorambucil, e.g. Cl—(C═O)—(CH$_3$)$_2$-(p-C$_6$H$_4$)—N(CH$_2$CH$_2$Cl)$_2$, with

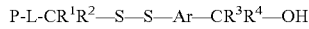

P-L-CR$^1$R$^2$—S—S—Ar—CR$^3$R$^4$—OH where the variables are as defined above. This synthetic scheme would also apply to activated derivatives of other carboxyl-containing compounds.

A2. In vitro Cleavage of mPEG-DTB-DSPE Conjugates

Figure 7:
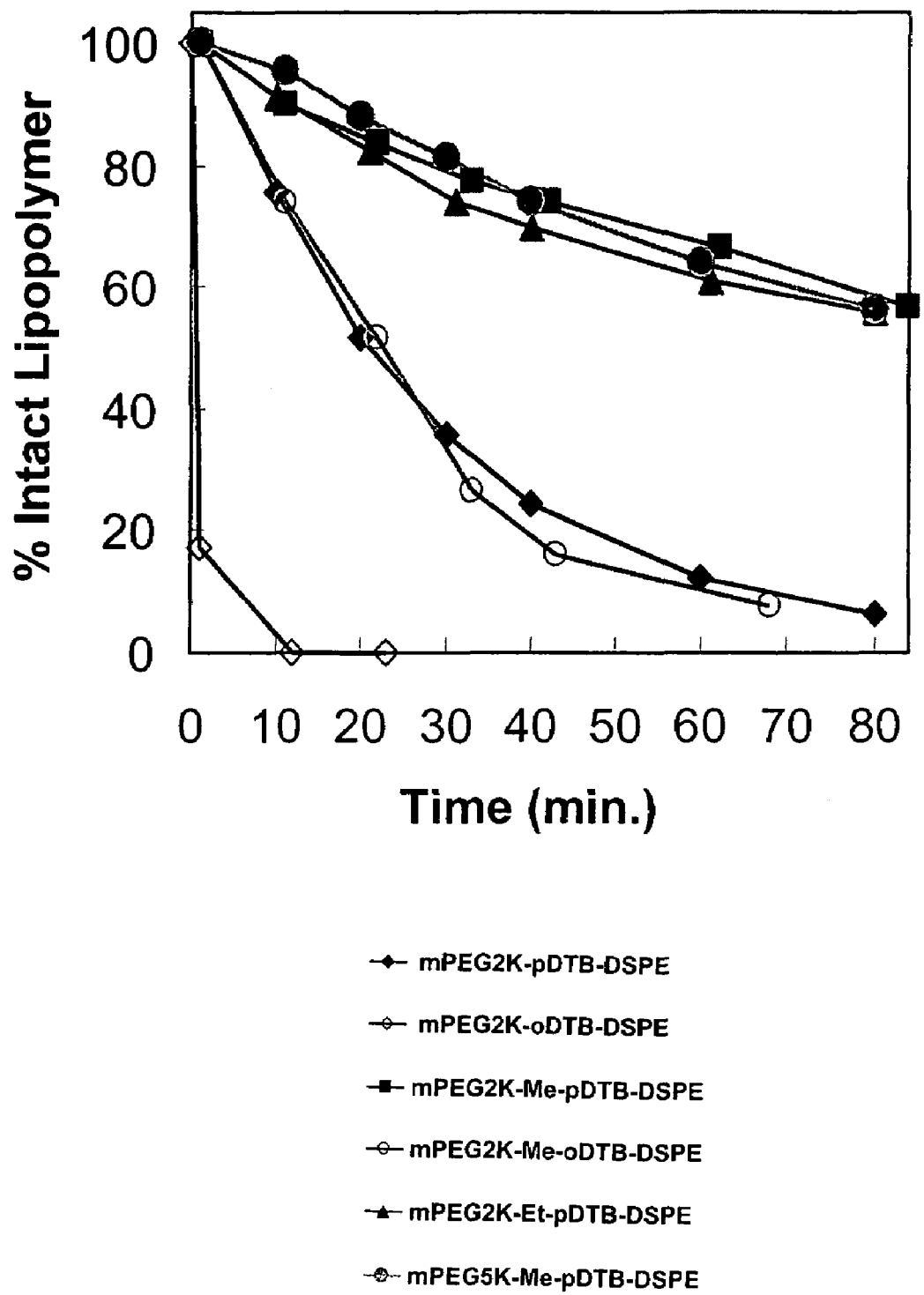
FIG. 7, which compares the stability of various mPEG-DTB-DSPE conjugates, shows the percentage of intact mPEG-DTB-DSPE micellar conjugates as a function of time, incubated in phosphate buffer containing 1 mM cysteine, the conjugates tested were para-mPEG$_{2000}$-DTB-DSPE (solid diamonds); ortho-mPEG$_{2000}$-DTB-DPSE (open diamonds); para-mPEG$_{2000}$-MeDTB-DSPE (solid squares); ortho-mPEG$_{2000}$-MeDTB-DPSE (open circles); para-mPEG$_{2000}$-EtDTB-DSPE (solid triangles); and para-mPEG$_{5000}$-DTB-DSPE (solid circles)

FIG. 7 illustrates cysteine-mediated cleavage of ortho- and para-mPEG-DTB-DSPE, ortho- and para-mPEG-MeDTB-DSPE, and para mPEG-EtDTB-DSPE (prepared as described in Example 1) micellar solutions of the conjugates in a buffered phosphate-saline aqueous solution (pH 7.2). The thiolytic cleavage was monitored in the presence of 1 mM cysteine by analyzing for disappearance of the conjugates by RP-HPLC, as described in Example 5. As seen, the conjugates having an unhindered DTB group, para-mPEG$_{2000}$-DTB-DSPE (solid diamonds) and ortho-mPEG$_{2000}$-DTB-DPSE (open diamonds), exhibited the fastest rate of cleavage, with the ortho conjugate considerably faster than the para conjugate. Hindering the DTB linkage with an methyl (Me) or ethyl (Et) group, as in the para-mPEG-MeDTB-DSPE (solid squares), ortho-mPEG-MeDTB-DPSE (open circles), and para-mPEG-EtDTB-DSPE (solid triangles) conjugates, significantly slowed the rate of cleavage. Increasing the molecular mass of PEG from 2000 Da to 5000 Da did not change the rate of cysteine-mediated cleavage (solid squares and solid circles). This experiment clearly illustrates that increasing the R group (FIG. 3A) makes the thiolysis noticeably slower.

A3. Liposome Compositions Comprising an mPEG-SS—Ar—CR$^3$R$^4$-Lipid Conjugate a. In vitro Characterization In one embodiment, the conjugates of the invention are formulated into liposomes. Liposomes are closed lipid vesicles used for a variety of therapeutic purposes, and in particular, for carrying therapeutic agents to a target region or cell by systemic administration. In particular, liposomes having a surface coating of hydrophilic polymer chains, such as polyethylene glycol (PEG), are desirable as drug carriers, since these liposomes offer an extended blood circulation lifetime over liposomes lacking the polymer coating. The polymer chains in the polymer coating shield the liposomes and form a "brush" of water solvated polymer chains about the liposomes. Thus, the polymer acts as a barrier to blood proteins, preventing binding of the protein and recognition of the liposomes for uptake and removal by macrophages and other cells of the reticuloendothelial system. However, to facilitate interactions with target cells all or a portion of the polymer "brush" would be removed with the cleavable lipopolymer of the current invention is used. This is particularly important for intracellular drug delivery and gene delivery (liposomal plasmid-DNA delivery).

Typically, liposomes having a surface coating of polymer chains are prepared by including in the lipid mixture between about 1 to about 20 mole percent of the lipid derivatized with the polymer, also referred to herein as a "lipopolymer". The actual amount of lipopolymer can be higher or lower, depending on the molecular weight of the polymer. In the present invention, liposomes are prepared by adding between about 1 to about 20 mole percent of polymer-lipid conjugates, including at least some conjugates of formula I above, to other liposome lipid bilayer components.

In various embodiments, the polymer chains in the above-referenced 1 to about 20 mole percent of lipids are attached to the lipids via the cleavable linking structures shown herein (i.e, the moiety L-CR$^1$R$^2$—S—S—Ar—CR$^3$R$^4$—Y), or by a linkage which is more stable in vivo, or, in a preferred embodiment, by a combination of linkages. In this case, higher molecular weight polymer chains are preferably linked via the cleavable linking structures shown herein, and shorter, lower molecular weight polymer chains by more stable linkages.

In another embodiment, some or all of the polymer chains contain a targeting moiety at the free terminus. Such targeting moieties include any of the exemplary moieties described above and in U.S. Pat. Nos. 6,043,094 and 5,891, 468 and are intended to facilitate in vivo binding to specific cells.

In studies performed in support of the invention, liposomes comprised of the vesicle-forming lipid PHPC (partially hydrogenated phosphatidyl choline), in combination with cholesterol and either the ortho-mPEG-DTB-DSPE or the para-mPEG-DTB-DSPE conjugate, were prepared as described in Example 6.

In other studies, liposomes were prepared from the lipid dioleoyl phosphatidylethanolamine (DOPE) and either the ortho-mPEG-DTB-DSPE or the para-mPEG-DTB-DSPE conjugate. DOPE is a hexagonal phase lipid which alone does not form lipid vesicles. However, liposomes form when DOPE is combined with a few mole percent of the mPEG-DTB-DSPE conjugate. Cleavage of the mPEG-DTB-DSPE conjugate triggers decomposition of the liposomes and release of liposomally-entrapped contents. Thus, the content release characteristics of such liposomes provides a convenient quantitative evaluation of cleavable PEG-bearing liposomes.

Liposomes comprised of DOPE and the ortho- or para-mPEG-DTB-DSPE (FIG. 3A, R=H) conjugate were prepared with entrapped fluorophores, p-xylene-bis-pyridinium bromide and trisodium 8-hydroxypyrenetrisulfonate, as described in Example 6A. Release of the fluorophores from liposomes incubated in the presence of cysteine at various concentrations was monitored as described in Example 6B.

Figure 8A:
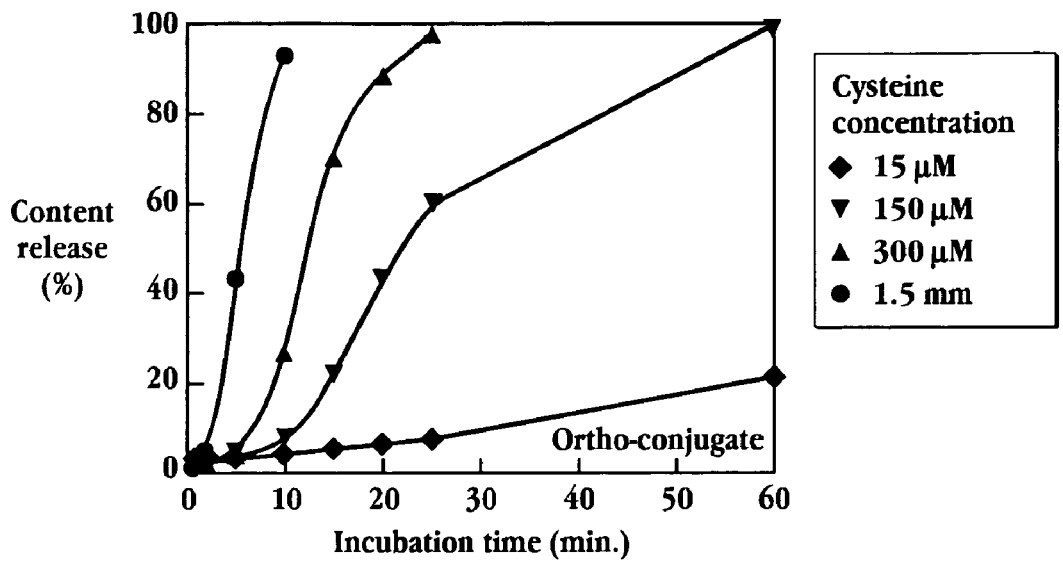
FIGS. 8A–8B show percentage of content release of entrapped fluorophore from liposomes comprised of DOPE:ortho-mPEG-DTB-DSPE (FIG. 8A) or of DOPE:para-mPEG-DTB-DSPE (FIG. 8B) conjugate, incubated in the presence of cysteine at the indicated concentrations.
Figure 8B:
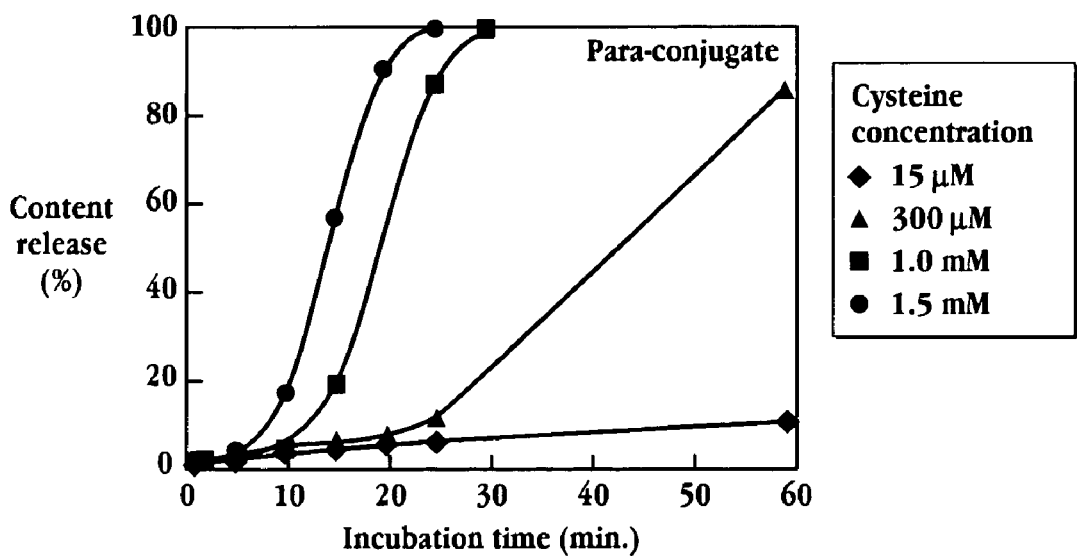

Results for liposomes comprising the ortho-conjugate are shown in FIG. 8A, where percentage of content release of entrapped fluorophore from liposomes incubated in the presence of cysteine at concentrations of 15 µM (solid diamonds), 150 µM (solid inverted triangles), 300 µM (solid triangles) and 1.5 mM (solid circles) are shown. FIG. 8B is a similar plot for liposomes comprising the para-conjugate, where the liposomes are incubated in cysteine at concentrations of 15 µM (solid diamonds), 300 µM (solid triangles), 1 µM (solid squares) and 1.5 mM (solid circles).

FIGS. 8A–8B show that both the ortho- and para-conjugates are cleaved when incorporated into liposomes, as evidenced by release of the entrapped dye, at a rate dependent on the concentration of cysteine. Control studies with non-cleavable mPEG-DSPE containing liposomes produced no content release (data not shown). These results also suggest that the ortho conjugate is more susceptible to thiolytic cleavage. For example, 300 µM cysteine liberates most of the contents of DOPE liposomes within 20 minutes. Under the same conditions, only a fraction of liposomes having para-mPEG-DTB-DSPE decomposed. Similarly, after incubation for 20 minutes at 150 µM cysteine, half of the entrapped contents was released for the ortho-containing liposomes, while even at 300 µm cysteine only approximately 10% of the contents were release in liposomes containing the para-conjugate. Both ortho and para conjugates have half-lives of less than 20 minutes at a cysteine level of 150 µM (Zalipsky, S. et al., *Bioconjugate Chem.*, 10:703 (1999)). This suggests that more than half of the original three mole percent of the mPEG-DTB-lipid must be cleaved to observe content release from the liposomes.

Decomposition of the mPEG-DTB-DSPE/DOPE liposomes in 15 µM cysteine, the average plasma concentration in both humans and rodents (Lash, L. H., et al., *Arch. Biochem. Biophys.* 240:583–592 (1985)), was minimal in the time frame of these experiments (60 minutes). This suggests that the mPEG-DTB-lipid conjugates might have sufficiently long lifetimes in plasma to allow the PEG-grafted vesicles to distribute systemically in vivo, or to accumulate in a specific site either passively or through ligand-mediated targeting. Local or short term increase in cysteine concentration can potentially be achieved by its intravenous or intra-arterial administration. The results shown in FIGS. 8A–8B also suggest that prolonged exposure to the natural plasma cysteine concentration (≈15 µM) would be sufficient to decompose most of these conjugates. These suggestions were studied in in vivo experiments, described below.

In another study performed in support of the invention, liposomes comprised of DOPE and three different mPEG$_{2000}$-DTB-lipid conjugates were prepared. The liposomes were prepared as described in Example 6 and included an entrapped fluorophore. The three lipopolymers were mPEG-DTB-DSPE as shown in FIG. 3A, where R is H; mPEG-MeDTB-DSPE as shown in FIG. 3A, where R is CH$_3$, and mPEG-MeDTB-distearoyl-glycerol, as shown in FIG. 6A. The liposomes were comprised of 97 mole percent DOPE and 3 mole percent of one of the mPEG-DTB-lipid conjugates. Cysteine-mediated rate of cleavage of the conjugates was determined by monitoring the release of entrapped fluorophore as a function of time in the presence of various cysteine concentrations. The results are shown in FIGS. 9A–9C, where the percent release of entrapped fluorophore is normalized for the release rate from liposomes incubated in buffer alone.

Figure 9A:
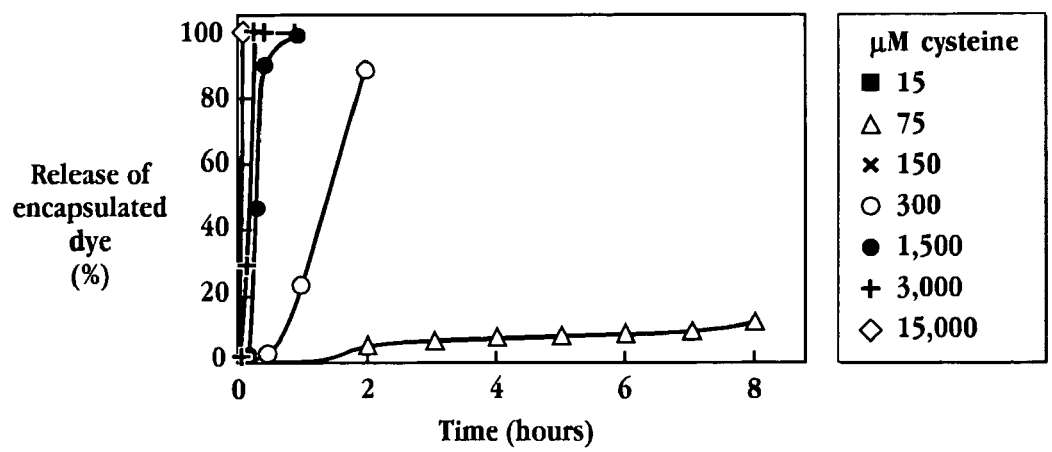
FIG. 9A shows normalized percent release of entrapped fluorophore as a function of time for liposomes comprised of DOPE and para-mPEG-DTB-DSPE (97:3 mole ratio). The percent release of entrapped fluorophore is normalized with respect to percent release of fluorophore from liposomes incubated in the absence of cysteine. The release rate from liposomes incubated in the presence of cysteine at concentrations of 15 μM (solid squares), 75 μM (open triangles), 150 μM (X symbols), 300 μM (open circles), 1500 μM (solid circles), 3000 μM (+symbols), and 15000 μM (open diamonds) is shown.

FIG. 9A shows the percent release of entrapped fluorophore as a function of time for liposomes comprised of DOPE and para-mPEG-DTB-DSPE (conjugate of FIG. 3A, R=H). The release rate from liposomes containing the conjugate and incubated in the presence of cysteine at concentrations of 15 µM (solid squares), 75 µM (open triangles), 150 µM (X symbols), 300 µM (open circles), 1500 µM (solid circles), 3000 µM (+symbols), and 15000 µM (open diamonds) is shown.

Figure 9B:
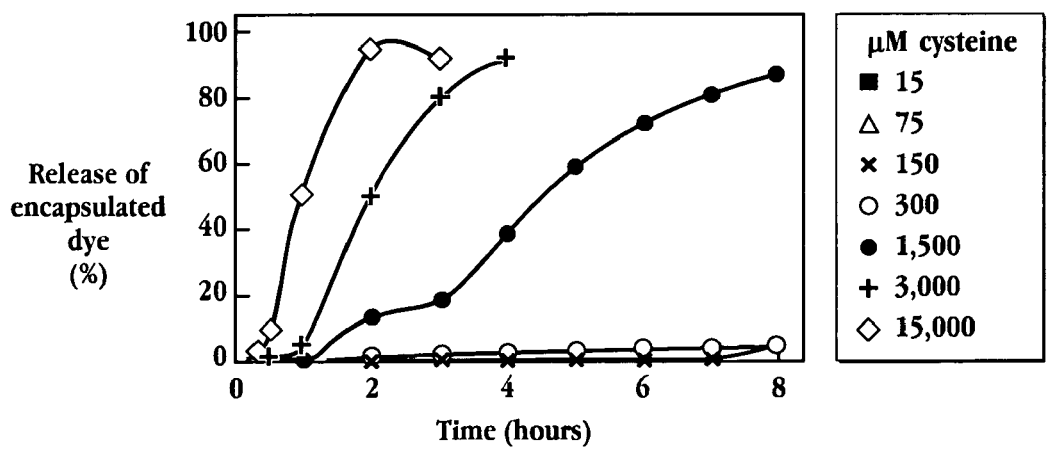
FIG. 9B shows normalized percent release of entrapped fluorophore as a function of time for liposomes comprised of DOPE and para-mPEG-MeDTB-DSPE (see FIG. 3A structure, R=CH$_3$). The percent release of entrapped fluorophore is normalized with respect to percent release of fluorophore from liposomes incubated in the absence of cysteine. The release rate for liposomes incubated in the presence of cysteine at concentrations of 15 μM (solid squares), 75 μM (open triangles), 150 μM (X symbols), 300 μM (open circles), 1500 μM (solid circles), 3000 μM (+symbols), and 15000 μM (open diamonds) is shown.

FIG. 9B shows the percent release of entrapped fluorophore as a function of time for liposomes comprised of DOPE and para mPEG-MeDTB-DSPE (R=CH$_3$, conjugate of FIG. 3A & 4B). The release rate of the fluorophore from liposomes incubated in the presence of cysteine at concentrations of 15 µM (solid squares), 75 µM (open triangles), 150 µM (X symbols), 300 µM (open circles), 1500 µM (solid circles), 3000 µM (+symbols), and 15000 µM (open diamonds) is shown. The content release is markedly slower than in FIG. 9A.

Figure 9C:
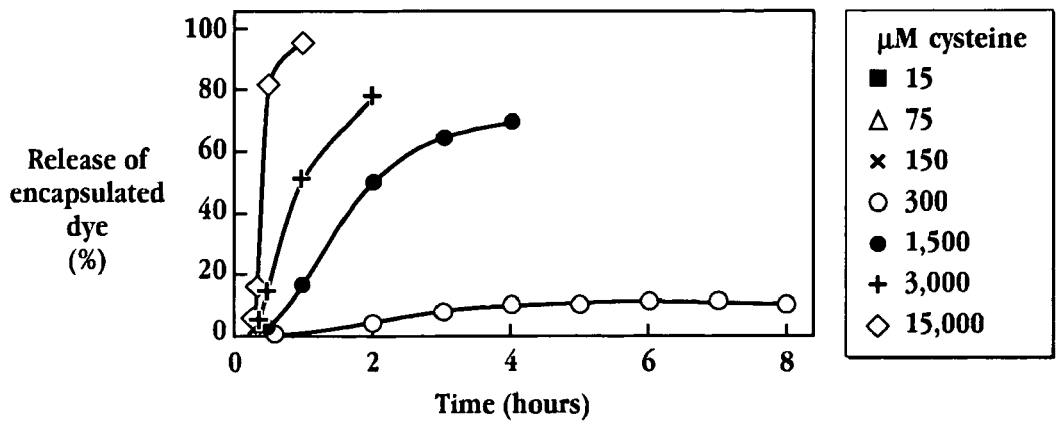
FIG. 9C shows normalized percent release of entrapped fluorophore as a function of time for liposomes comprised of DOPE and the mPEG-MeDTB-distearoyl-glycerol (conjugate of FIG. 6). The percent release of entrapped fluorophore is normalized with respect to percent release of fluorophore from liposomes incubated in the absence of cysteine. The release rate of dye upon cleavage of the conjugate from liposomes incubated in the presence of cysteine at concentrations of 15 μM (solid squares), 75 μM (open triangles), 150 μM (X symbols), 300 μM (open circles), 1500 μM (solid circles), 3,000 μM (+symbols), and 15,000 μM (open diamonds) is shown.

FIG. 9C is a similar plot for liposomes formed with DOPE and mPEG-MeDTB-distearoyl glycerol (conjugate of FIG. 6A). The release rate of dye from liposomes incubated in the presence of cysteine at concentrations of 15 µM (solid squares), 75 µM (open triangles), 150 µM (X symbols), 300 µM (open circles), 1500 µM (solid circles), 3000 µM (+symbols), and 15000 µM (open diamonds) is shown.

FIGS. 9A–9C show that the rate of mPEG-MeDTB-lipid cleavage is cysteine-concentration dependent, with a slow rate of cleavage, as evidenced by release of entrapped fluorophore, at cysteine concentrations of 15–75 µM. In comparing the data in FIG. 9A with that in FIG. 9B, it is seen that the mPEG-MeDTB-DSPE conjugate (FIG. 9B) containing liposomes release their contents approximately 10 times more slowly than the mPEG-DTB-DSPE-containing counterpart liposomes (FIG. 9A). Thus, the rate of cleavage can be tailored according to the R moiety (see FIGS. 3A and 7) in the DTB linkage, which hinders the access of thiols to the disulfide linkage of the DTB. Note that the results in FIGS. 9B and 9C are very similar, supporting the notion that R group size can be used to fine tune the lipopolymer cleavage rate.

b. In vivo Characterization

The blood circulation lifetimes of liposomes that include a mPEG$_{2000}$-DTB-lipid conjugates in accord with the invention, prepared as described in Example 7, was determined in mice. EDTa-chelated In$^{111}$ was entrapped in the liposomes, to allow their quantification in plasma at various time points. After intravenous administration in mice, blood samples were taken at various times and analyzed for the presence of liposomes, as evidenced by the presence of In$^{111}$.

Figure 10:
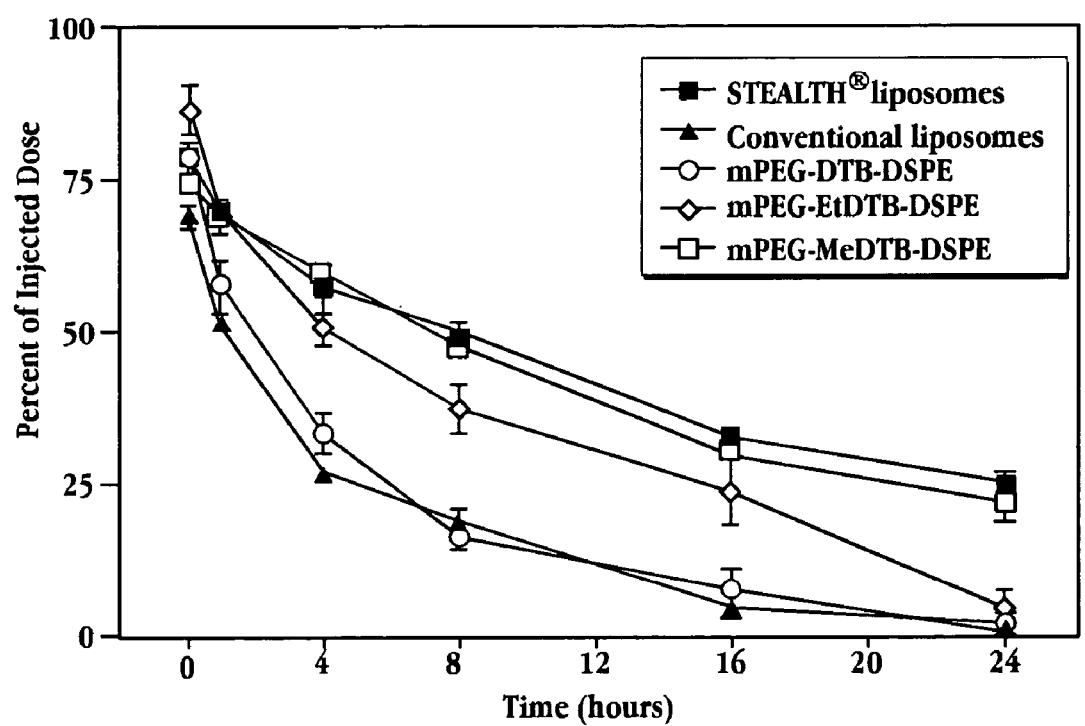
FIG. 10 is a plot showing the percent of injected dose of $^{111}$In-DTPA liposomes of HSPC/cholesterol/mPEG$_{2000}$-derived lipopolymer (55:40:5) in mice as a function of time, in hours. Liposomes containing an mPEG-DTB conjugate (see FIG. 3A, R=H, open circles), an mPEG-EtDTB-DSPE conjugate (open diamonds), or an mPEG-MeDTB-DPSE conjugate (see FIG. 3A, R=CH$_3$, open squares), and for liposomes containing an mPEG-DSPE conjugate joined by a non-cleavable urethane linkage ("Stealth®" liposomes, closed squares) and liposomes without PEG coating ("conventional" liposomes HSPC/Chol (55:45), closed triangles)

The blood clearance curves are shown in FIG. 10. Liposomes containing an mPEG-DTB-DSPE conjugate (open circles, FIG. 3A, R=H), an mPEG-EtDTB-DSPE conjugate (open diamonds, FIG. 3A, R=Et), or an mPEG-MeDTB-DPSE conjugate (open squares, FIG. 3A, R=Me) were prepared as described in Example 7.

For comparison, liposomes containing an mPEG-DSPE conjugate joined by a non-cleavable urethane linkage ("Stealth®" liposomes, closed squares) and liposomes with no PEG coating ("conventional" liposomes (closed triangles)) were also administered to the mice. As seen in FIG. 10, liposomes with no PEG coating (closed triangles) were cleared rapidly from the bloodstream, with a few percent remaining 24 hours after injection. Essentially the same clearance curve was obtained for "unhindered" mPEG-DTB-DSPE (FIG. 3A, R=H) liposomes (open circles). Liposomes having an mPEG-Me-DTB-DSPE conjugate (open squares) have a significantly extended blood circulation time with over 25% of the liposomes in circulation 24 hours after injection. The circulation lifetime of these liposomes was comparable to that of so-called "Stealth®" liposomes, that have a coating of PEG joined by a non-cleavable linkage (closed squares). The liposomes with an mPEG-EtDTB-DSPE (open diamonds) had an extended blood circulation time for the period between about 1–16 hours, similar to MeDTB-linked analog. These results indicate that the MeDTB linkage survives for a long time in blood plasma, and increasing the R group size from methyl (Me) to ethyl (Et) has little effect. Preferably, however, to obtain long-circulating liposomes, R group (FIG. 3A) should be larger than hydrogen.

In other studies not shown here, the blood circulation lifetime of liposomes containing an mPEG-MeDTB-lipid conjugate was compared to that of liposomes containing a polymer-lipid conjugate where the polymer and lipid were joined by an unhindered aliphatic disulfide bond. Unhindered disulfide linkages are readily cleaved in vivo (Worrell, N. R. et al., *Anti-Cancer Drug Design*, 1:179 (1986); Thorpe, P. E. et al., *Cancer Res.*, 47:5924 (1987)), and the blood circulation lifetime of liposomes having polymer chains grafted to their surface by an unhindered aliphatic disulfide typically do not have the extended blood circulation lifetime observed for liposomes having stably linked polymer chains. The —SS—Ar—CR$^3$R$^4$— linkage of the invention, and in particular the more sterically hindered DTB, e.g, R=CH$_3$ linkages, are more stable in vivo and achieve a longer blood circulation lifetime than liposomes with polymer chains attached via an unhindered aliphatic disulfide linkage. Importantly, cleavage of the polymer-DTB-lipid conjugate of the invention results in regeneration of the original lipid in unmodified form. This is desirable since unnatural, modified lipids can have undesirable in vivo effects. At the same time, the conjugate is stable when stored in the absence of reducing agents.

B. Amine-linked Polypeptide Conjugates

Figure 11A:
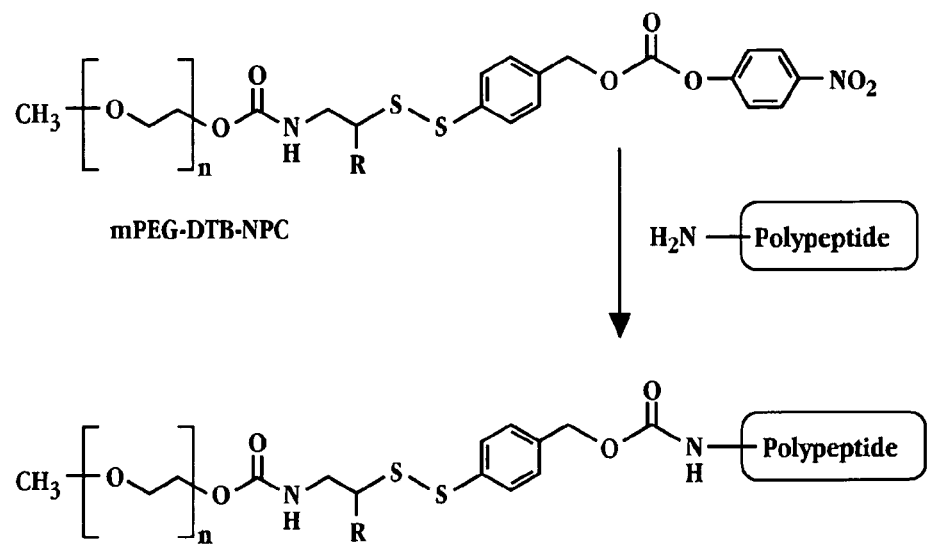
FIG. 11A shows a synthetic reaction scheme for synthesis of an mPEG-DTB-protein conjugate in accord with another embodiment of the invention.

In another embodiment, the invention includes a conjugate as described above, where the amine-containing ligand compound is a polypeptide. A synthetic reaction scheme showing preparation of a polymer-DTB-polypeptide conjugate is shown in FIG. 11A, with mPEG as the exemplary polymer. In general, an amino-reactive derivative, such as mPEG-DTB-NPC, is prepared according to one the synthetic routes described above in FIGS. 2, 4A, 5, and 6C. The leaving group can be nitrophenol or any one of the others described above. The mPEG-DTB-nitrophenyl carbonate compound is coupled to an amine group on a polypeptide forming a urethane linkage. The R group adjacent the disulfide can be H, CH$_3$, C$_2$H$_5$, C$_3$H$_7$, or the like, and is selected according to the desired rate of disulfide cleavage.

Figure 11B:
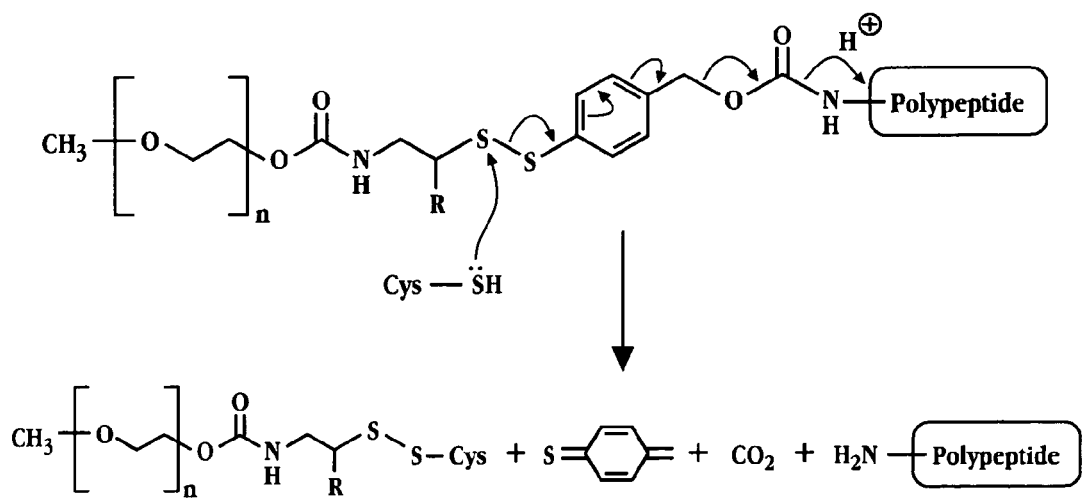
FIG. 11B shows the decomposition products after thiolytic cleavage of the conjugate in FIG. 11A and release of the parent protein.

FIG. 11B shows the thiolytic decomposition reaction and products exemplified by cysteine-mediated cleavage of the conjugate. As can be seen, the native protein, with no modification to the protein amine group, is regenerated upon cleavage. This is a significant feature of the present invention, i.e., the parent protein, polypeptide, and/or peptide is regenerated unchanged.

Attachment of polymer chains, such as PEG, to a polypeptide often diminishes the enzymatic or other biological activity (Zalipsky, S., *Adv. Drug Delivery Rev.*, 16:157 (1995)), e.g., receptor binding, of the polypeptide. However, polymer modification of a polypeptide provides the benefits of decreased immunogenicity and antigenicity, as well as increased polypeptide blood circulation lifetime, improved polypeptide solubility, and increased polypeptide resistance to proteolysis. In the present invention, the polymer-polypeptide conjugate is administered to a subject. As the conjugate circulates, exposure to physiologic reducing conditions, such as blood cysteine and other in vivo thiols and reducing enzymes, initiates cleavage of the hydrophilic polymer chains from the polypeptide (FIG. 11B). As the polymer chains are cleaved from the polypeptide, the biological activity of the polypeptide is gradually increased and ultimately restored to the level of the native protein. In this way, the polypeptide initially has a sufficient blood circulation lifetime for biodistribution, and over time regains its full biological activity as the polymer chains are cleaved. This is essentially a prodrug approach where a polymer, e.g., PEG, is acting as pro-moiety of a polypeptide drug.

In various embodiments, the polymer chains are attached to the polypeptide via the cleavable linking structures shown herein (i.e, the moiety L-CR$^1$R$^2$—S—S—Ar—CR$^3$R$^4$—Y), or by a linkage which is more stable in vivo, or by a combination of linkages. This approach allows for attachment of PEG chains to amino groups in the polypeptide essential for biological activity with a reversible linkage, and attachment to amino groups that are not essential to peptide activity with a more stable linkage.

In another embodiment, some or all of the polymer chains contain a targeting moiety at the free terminus. Such targeting moieties include any of the moieties discussed above.

In a study performed in support of the invention, lysozyme was used as a model polypeptide. As described in Example 8, lysozyme was incubated with mPEG-MeDTB-nitrophenylcarbonate in 0.1 M borate, at pH 9, at a 2:1 ratio of nitrophenylcarbonate to amino group of lysozyme. After reactions times of 15 minutes and 3 hours, separate samples were characterized by SDS-PAGE. A comparative conjugate was prepared by reacting lysozyme under the same conditions for 60 minutes with mPEG-nitrophenyl carbonate, which will form a stable mPEG-lysozyme conjugate.

Figure 12A:
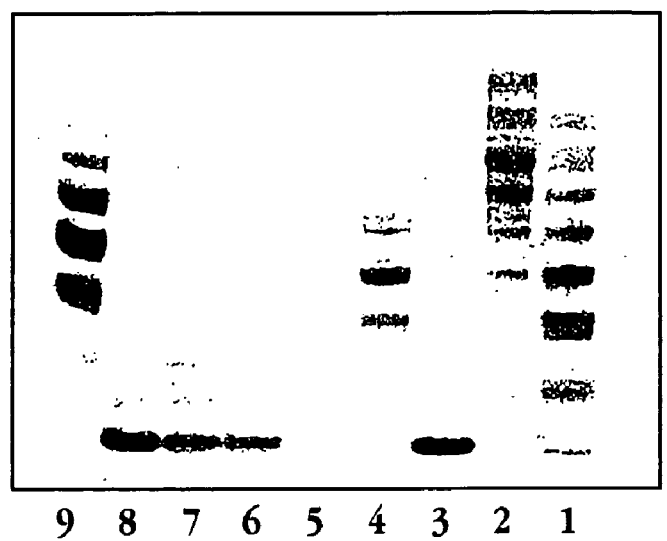
FIG. 12A is a rendering of a photograph of an sodium-dodecyl-sulfate polyacrylamide gel electrophoresis (SDS-PAGE) profile of lysozyme reacted for 15 minutes (Lane 1) or for 1 hour (Lane 2) with mPEG-MeDTB-nitrophyenyl carbonate (prepared according to FIGS. 4A & 5 from mPEG, 5000 Daltons) to form a mPEG-MeDTB-lysozyme conjugate; native lysozyme (Lane 3); lysozyme reacted for 1 hour with mPEG-nitrophenylcarbonate (Lane 4); molecular weight markers (Lane 5); and the samples of Lanes 1–4 treated with 2% β-mercaptoethanol for 10 minutes at 70° C. (Lanes 6–9)

FIG. 12A shows a rendering of the SDS-PAGE gel. Lane 1 corresponds to the reaction product formed after 15 minutes reaction of lysozyme with mPEG-MeDTB-nitrophenyl carbonate, and Lane 2 represents the reaction product formed after 1 hour reaction time. Lane 3 represents native lysozyme, and Lane 4 corresponds to lysozyme reacted for 1 hour with mPEG-nitrophenylcarbonate (Veronese et al., Applied Biochem. and Biotech, 11:141–152 (1985)). The molecular weight markers in Lane 5 are as follows, from the top down:

| Molecular Weight (kDaltons) | Marker |
|---|---|
| 1163 | β-galactosidase |
| 97.4 | phosphorylase b |
| 66.3 | bovine serum albumin |
| 55.4 | glutamic dehydrogenase |
| 36.5 | lactate dehydrogenase |
| 31 | carbonic anhydrase |
| 21.5 | trypsin inhibitor |
| 14.4 | lysozyme |

Comparison of Lane 1 and Lane 2 shows that the longer reaction time results in an increase in molecular weight of the product, consistent with additional mPEG chains conjugated to the polypeptide at longer incubation time.

Lanes 6–9 of the gel correspond to the samples in Lanes 1–4, but under reducing SDS-PAGE conditions, after treatment with 2% β-mercaptoethanol for 10 minutes at 70° C. The mPEG-MeDTB-lysozyme conjugate, after exposure to a reducing agent, decomposed to regenerate native lysozyme, as evidenced by the band in Lanes 6 and 7 at 14.4 kDa. In contrast, the stable mPEG-lysozme conjugate was not affected upon incubation with a reducing agent, as evidenced by the agreement in the profile in Lane 9 and Lane 4.

Also evident from the SDS-PAGE profile is that covalent attachment of mPEG-MeDTB to a protein forms a mixture of conjugates containing various mPEG-protein ratios. This ratio is dependent on the reaction time and conditions. This is clearly seen in viewing the bands in Lanes 1 and 2, where Lane 1 shows lysozyme derivatized with about 1–6 PEG chains. In Lane 2, the longer reaction time yielded mPEG-MeDTB-lysozyme conjugates with a higher mPEG-protein ratio. All cleavable conjugates were readily cleaved to regenerate the native protein, as seen in the bands of Lanes 6 and 7.

Figure 12B:
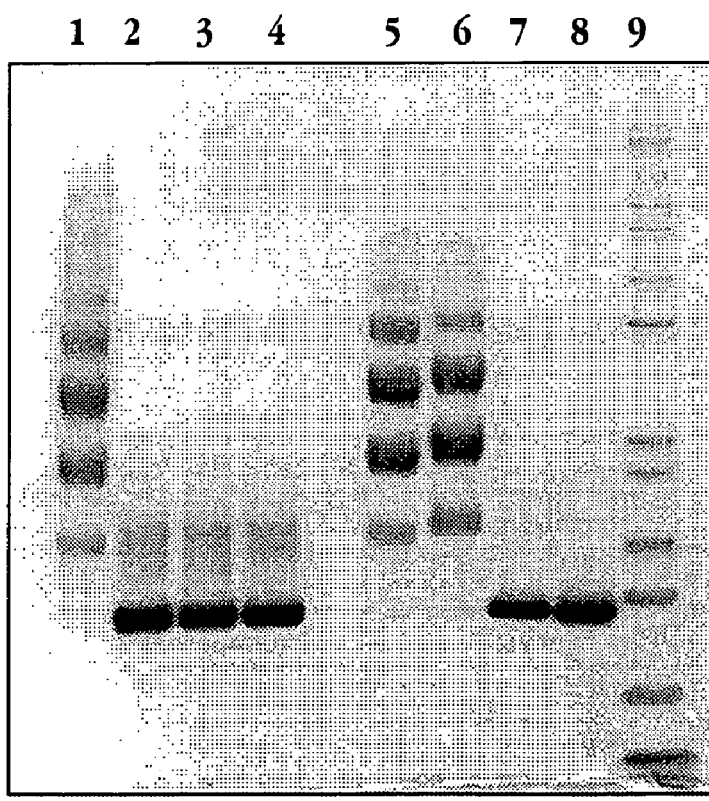
FIG. 12B is another SDS-PAGE profile of an mPEG$_{5000}$-MeDTB-lysozyme conjugate (Lane 1) treated with 1 mM cysteine (Lane 2), 5 mM cysteine (Lane 3), and 50 mM cysteine (Lane 4). Also shown are an mPEG-lysozyme conjugate (no cleavable linkage) before (Lane 5) and after treatment (Lane 6) with 50 mM cysteine. Lysozyme before (Lane 7) and after (Lane 8) treatment with 50 mM cysteine are also shown. Lane 9 corresponds to protein markers.

A similar study was done using cysteine as a reducing agent on a purified mPEG$_{5000}$-MeDTB-lysozyme conjugate. The results of the SDS-PAGE profile are shown in FIG. 12B, where an mPEG-MeDTB-lysozyme conjugate (Lane 1) treated with 1 mM cysteine (Lane 2), 5 mM cysteine (Lane 3), and 50 mM cysteine (Lane 4) are shown. Also shown are an mPEG-lysozyme conjugate (no cleavable linkage) before (Lane 5) and after treatment (Lane 6) with 50 mM cysteine. Lysozyme before (Lane 7) and after (Lane 8) with 50 mM cysteine are also shown. Lane 9 corresponds to protein markers. It is apparent that cysteine is an effective reducing agent for the DTB linkage and it does not affect the non-cleavable control.

Figure 13A:
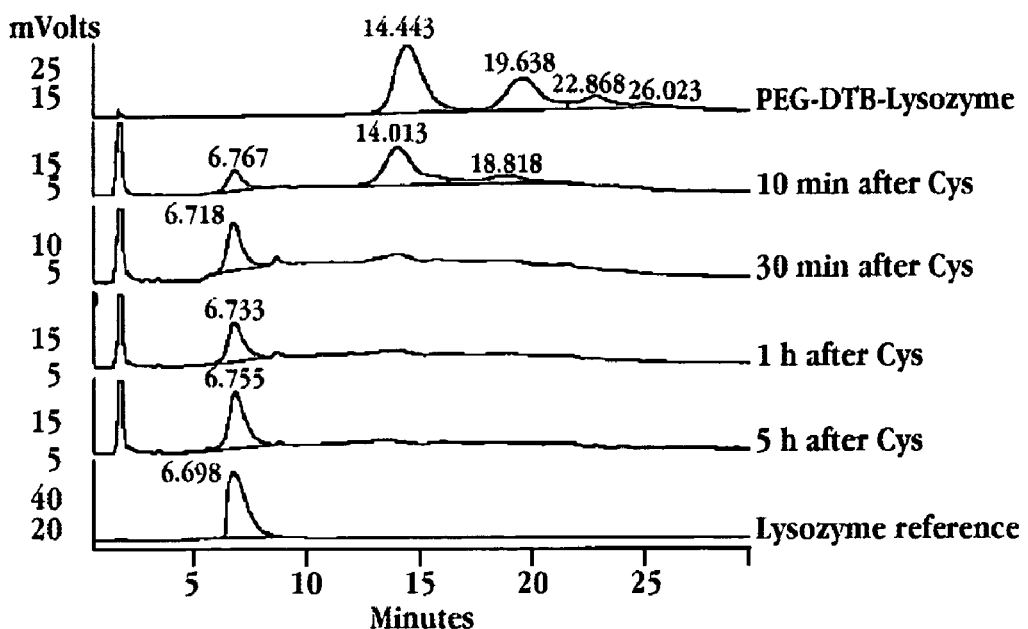
FIG. 13A shows RP-HPLC traces of PEG$_{5000}$-MeDTB-lysozyme conjugate (structure of FIG. 11, R=CH$_3$, polypeptide=lysozyme) before contact with 1 mM cysteine and as a function of time after contact with cysteine. The trace at the bottom of FIG. 13A corresponds to neat lysozyme.
Figure 13B:
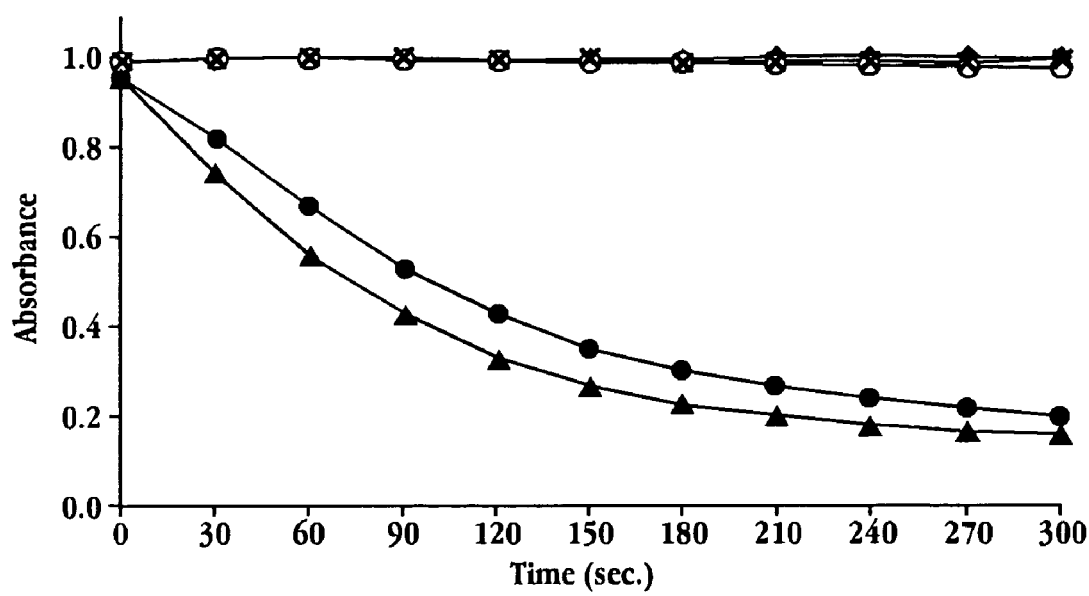
FIG. 13B graphically shows the bacterial cell wall lysis turbidometric assay of enzyme activity with lysozyme (solid triangles), mPEG-lysozyme with non-cleavable urethane linkage (X symbols), and mPEG$_{5000}$-MeDTB-lysozyme (open circles) before thiolysis and of mPEG$_{5000}$-MeDTB-lysozyme (solid circles) and mPEG-lysozyme (solid diamonds) after thiolysis with 1 millimolar (mM) cysteine.

FIG. 13A shows the reverse-phase HPLC traces of mPEG$_{5000}$-MeDTB-lysozyme conjugates before contact with 1 mM cysteine and as a function of time after contact with cysteine. Example 8 describes the methodology of the reverse-phase HPLC analysis. The trace at the bottom of FIG. 13A corresponds to neat lysozyme. As seen, cleavage of the DTB linkage to release lysozyme is apparent in the trace taken at 10 minutes post contact with cysteine, with cleavage and release of lysozyme near completion by the 30 minute time point. As illustrated in FIG. 13B, nearly all the cell-lysing activity of lysozyme was restored upon the cleavage of PEG.

Figure 14A:
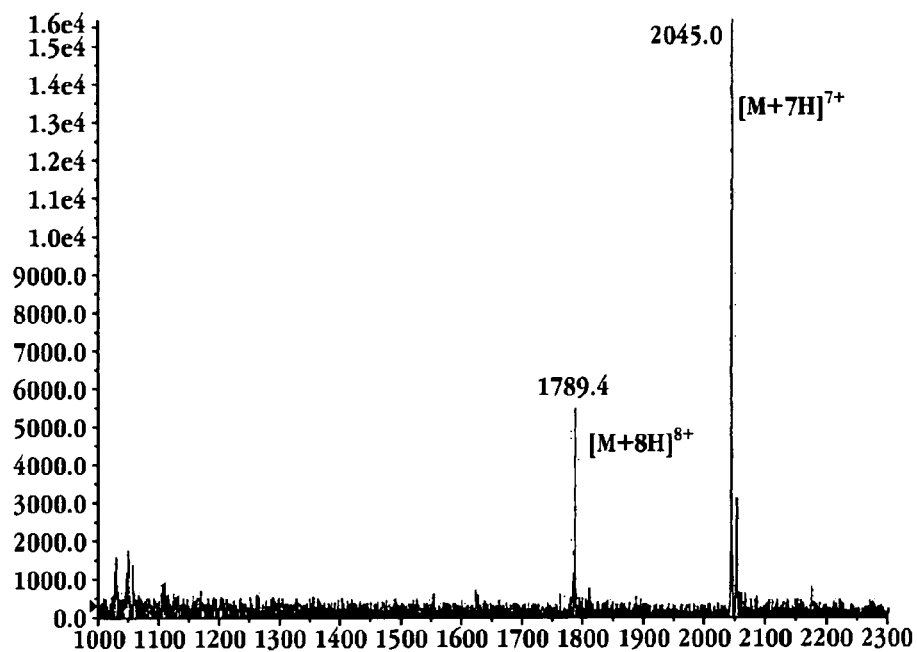
FIGS. 14A–14B are ion spray LC/MS scans of an mPEG-MeDTB-lysozyme conjugate after exposure to cysteine (FIG. 14A) and of neat lysozyme (FIG. 14B)
Figure 14B:
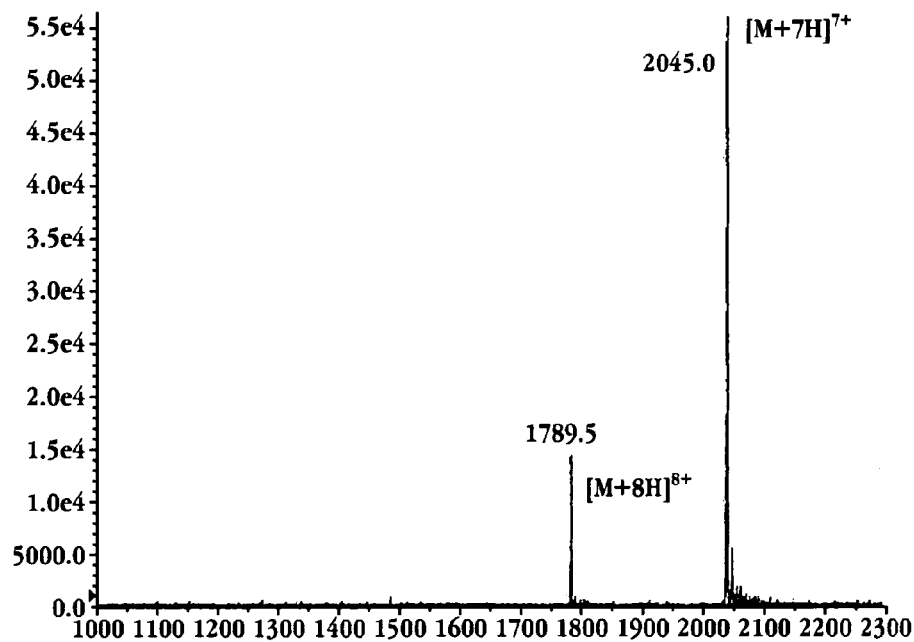

FIG. 14A–14B are ion spray LC/MS scans of an mPEG-MeDTB-lysozyme conjugate after exposure to cysteine (FIG. 14A) and of neat lysozyme (FIG. 14B) (Example 8). As seen the two traces are identical, indicating the lysozyme in its native form is released from the conjugate upon cleavage of the DTB linkage.

The mPEG$_{12000}$-MeDTB-lysozyme conjugates were administered in vivo to rats to characterize the in vivo behavior of the conjugate and its ability to cleave under physiologic conditions. In a first study, nine rats were divided into three test groups for administration of PEG-lysozyme, PEG-MeDTB-lysozyme, or free lysozyme. The test compound was administered intravenously or subcutaneously and blood samples were taken at defined times for analysis of blood lysozyme concentration. The results are shown in FIGS. 15A–15B.

Figure 15A:
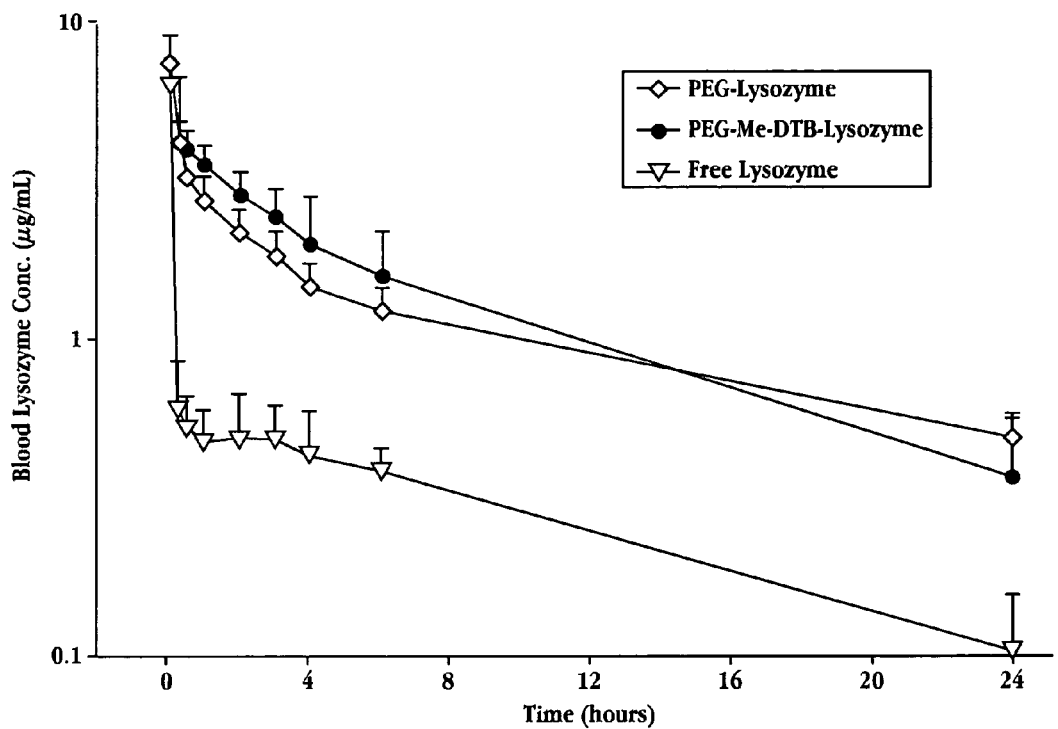
FIGS. 15A–15B show the blood lysozyme concentrations (ng/mL) in rats after intravenous (FIG. 15A) and subcutaneous (FIG. 15B) administration of $^{125}$I-lysozme (inverted triangles), non-cleavable urethane-linked PEG$_{12000}$-lysozyme (diamonds) and PEG$_{12000}$-MeDTB-lysozyme (circles)

FIG. 15A shows the results for the animals treated intravenously (i.v.) with $^{125}$I-lysozyme (inverted triangles), PEG$_{12000}$-lysozyme (diamonds) or PEG$_{12000}$-MeDTB-lysozyme (circles). Free lysozyme is rapidly cleared from the bloodstream, with more than 10-fold blood concentration decrease within one hour after administration ($T_{1/2\alpha}$=0.25 hr; $T_{1/2\beta}$=24.1 hr). The lysozyme-PEG conjugates had a substantially longer blood circulation lifetime (PEG$_{12000}$-MeDTB-lysozyme $T_{1/2\alpha}$=3.71 hr; $T_{1/2\beta}$=37.2 hr; PEG$_{12000}$-lysozyme $T_{1/2\alpha}$2.17 hr; $T_{1/2\beta}$=32.9 hr). This experiment suggests that MeDTB linkage survives in circulation long enough to realize the benefits associated with PEG, discussed above. Hindered disulfides have improved stability in plasma (Worrell, N. R. et al., *Anti-Cancer Drug Design*, 1:179 (1986); Thorpe, P. E. et al., *Cancer Res.*, 47:5924 (1987)).

Figure 15B:
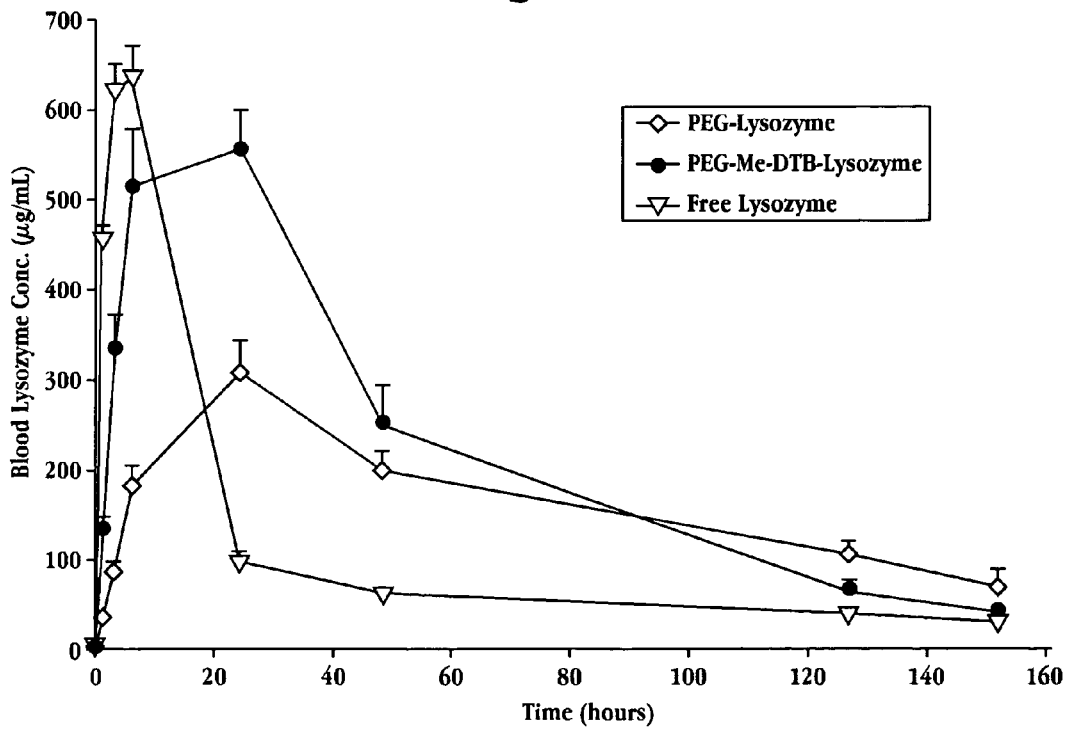

FIG. 15B shows the results for the animals treated subcutaneous with $^{125}$I-lysozyme (inverted triangles), PEG$_{12000}$-lysozyme (diamonds) or PEG$_{12000}$-MeDTB-lysozyme The PEG-linked lysozyme conjugates are slower to reach the bloodstream and are cleared more slowly from the blood, relative to native lysozyme. In this study, the best bioavailability (larger AUC) was obtained for the cleavable PEG$_{12000}$-MeDTB-lysozyme.

Figure 16A:
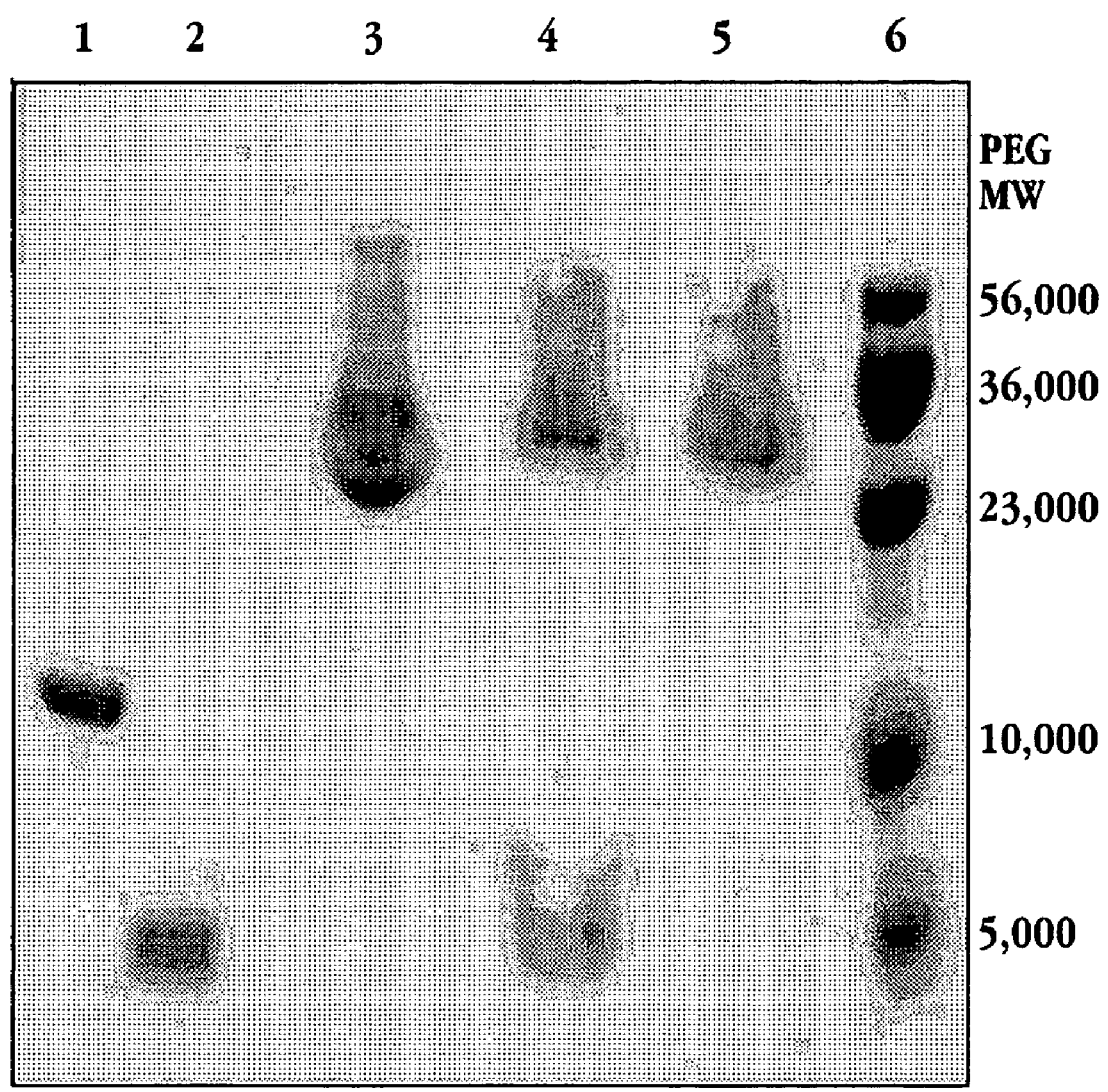
FIG. 16A is a polyacrylamide gel (SDS-PAGE) stained for visibility of PEG of PEG-lysozyme under various conditions, where Lane 1 corresponds to mPEG$_{5000}$-MeDTBlysozyme, Lane 2 corresponds to mPEG$_{5000}$-MeDTB-lysozyme in cysteine buffer, Lane 3 corresponds to mPEG$_{5000}$-MeDTB-lysozyme in plasma for 18 hours, Lane 4 corresponds to mPEG$_{5000}$-MeDTB-lysozyme in plasma treated with 1,4-dithio-DL-threitol (DTT), Lane 5 is a plasma sample control, and Lane 6 is PEG molecular weight markers.

A PEG-MeDTB-lysozyme conjugate was assessed by SDS-PAGE, and the results are shown in FIG. 16A. The samples were stained with iodine, for PEG visualization. Lane 1 corresponds to mPEG$_{5000}$-MeDTB-lysozyme, Lane 2 corresponds to mPEG$_{5000}$-MeDTB-lysozyme in cysteine buffer, Lane 3 corresponds to mPEG$_{5000}$-MeDTB-lysozyme in plasma for 18 hours, Lane 4 corresponds to mPEG$_{5000}$-MeDTB-lysozyme with 1,4-dithio-DL-threitol (DTT) added, Lane 5 is a plasma sample control, and Lane 6 is PEG molecular weight markers. The gel suggests that MeDTB is cleaved in plasma by a high molecular weight protein, forming a disulfide-linked PEG intermediate. Free PEG is liberated after treatment with low molecular weight thiol, such as DTT.

Figure 16B:
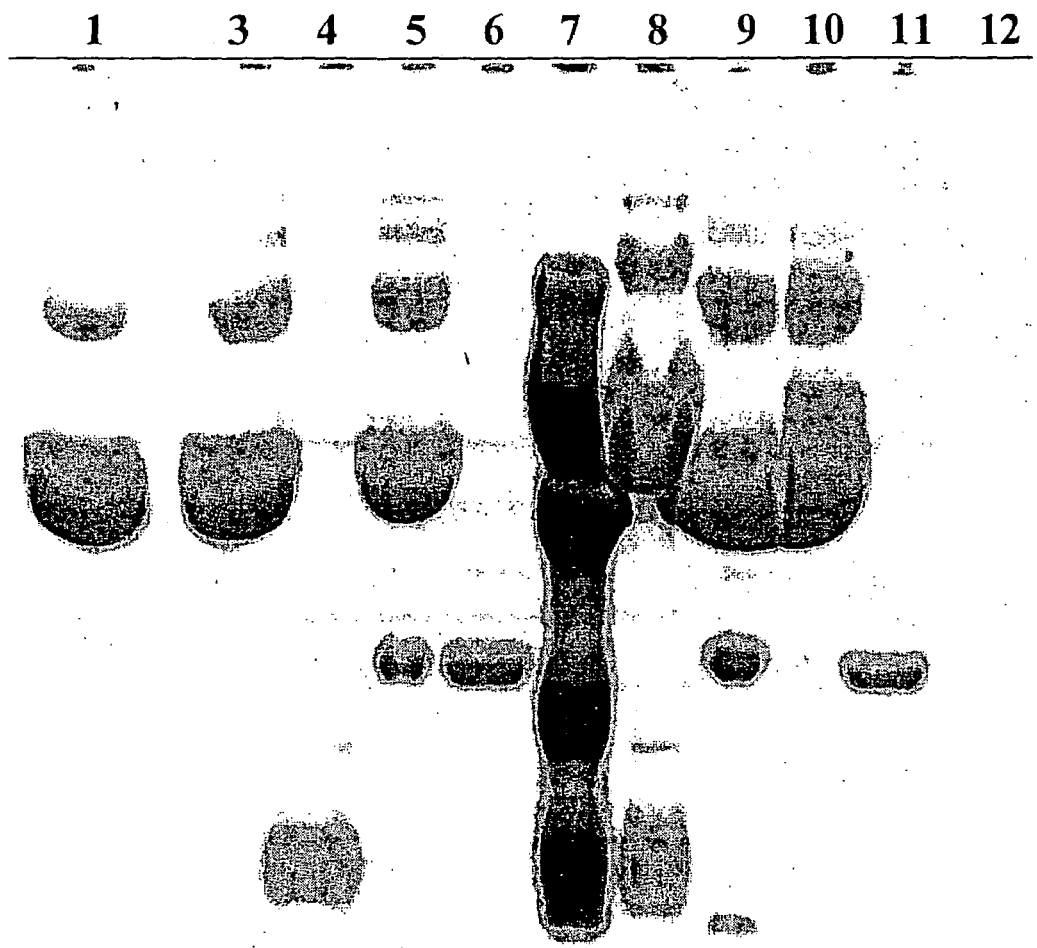
FIG. 16B is a polyacrylamide gel (SDS-PAGE) stained for visibility of PEG of PEG-lysozyme under various conditions, where Lane 1 corresponds thiol-blocked (I—CH$_2$CONH$_2$) albumin, Lane 2 is empty, Lane 3 corresponds to albumin, Lane 4 corresponds to mPEG$_{5000}$-MeDTB-lysozyme treated with cysteine, Lane 5 corresponds to mPEG$_{5000}$-MeDTB-lysozyme treated with albumin, Lane 6 corresponds to mPEG$_{5000}$-lysozyme, Lane 7 corresponds to PEG molecular weight markers, Lane 8 corresponds to mPEG$_{5000}$-MeDTB-lysozyme treated with albumin and with 1,4-dithio-DL-threitol (DTT), Lane 9 corresponds to mPEG$_{5000}$-MeDTB-lysozyme treated with corresponds thiol-blocked albumin; Lane 10 corresponds to mPEG$_{5000}$-MeDTB-lysozyme treated with albumin, Lane 11 corresponds to mPEG$_{5000}$-MeDTB-lysozyme, and Lane 12 corresponds to lysozyme.

In another set of studies, it was shown that the thiol group of albumin was acting as the cleaving agent. Albumin is an abundant protein-thiol in plasma (Kratz, F. et al. *J. Med. Chem.*, 45:5523 (2002)). The SDS-PAGE gel from this studying is shown in FIG. 16B, where Lanes 1–12 were as follows:

| Lane | Test Substance |
|---|---|
| 1 | thiol-blocked (I—CH$_2$CONH$_2$) albumin[1] |
| 2 | empty |
| 3 | albumin (0.7 thiols/mole) |
| 4 | mPEG-DTB-lysozyme + cysteine |
| 5 | mPEG-lysozyme + albumin |
| 6 | mPEG-lysozyme |
| 7 | PEG molecular weight markers (5, 10, 23, 36, 56 kDaltons) |

-continued

| Lane | Test Substance |
|------|----------------|
| 8 | mPEG-DTB-lysozyme + albumin + dithio threitol (DTT) |
| 9 | mPEG-DTB-lysozyme + thiol-blocked albumin |
| 10 | mPEG-DTB-lysozyme + albumin |
| 11 | mPEG-DTB-lysozyme |
| 12 | lysozyme |

[1] all references to "albumin" are bovine serum albumin

The gel was stained for visibility of PEG. Lanes 1 and 3 show that albumin appears as a pair of spots near the top portion of the gel. Lane 11 shows the position of the mPEG-DTB-lysozyme conjugate, close to the 10,000 Dalton PEG molecular weight marker. Lane 4 shows that the mPEG-DTB-lysozyme conjugate is cleaved in the presence of cysteine, as evidenced by the spot at 5000 Daltons that corresponds to the released PEG. Lane 10 corresponds to mPEG-DTB-lysozyme treated with albumin and no spot on the gel corresponding to the mPEG-DTB-lysozyme conjugate is visible (compare to Lane 11), nor is a spot corresponding to released PEG visible (compare to Lane 4). This suggests that the mPEG-DTB-lysozyme conjugate was cleaved by the albumin and that the cleavage products are in the spot at the top of the gel that corresponds to the albumin. Treatment of the mPEG-DTB-lysozyme with both albumin and dithio threitol (DTT) (Lane 8) resulted in release of the PEG from the albumin, lysozyme, PEG mixture, as evidenced by the appearance of a spot at the 5000 Dalton position. This study shows that the DTB linkage is cleaved by albumin.

In other studies, erythropoietin (EPO) was conjugated to mPEG$_{12000}$MeDTB-NPC at pH 7 and PEG/protein molar ratios of 6:1 ("lightly PEGylated") and at pH 8 and PEG/protein molar ratios of 9:1 ("heavily PEGylated"). As comparative non-cleavable conjugates, EPO was conjugated to mPEG$_{12000}$-NPC in the same buffer at PEG/protein molar ratios of 8:1 and 12:1. Preparation of the PEG-modified EPO is described in Example 9. The mPEG-MeDTB-EPO and mPEG-EPO conjugates were characterized by SDS-PAGE and HPLC-SEC, with the results shown in FIGS. 17A–17B and FIGS. 18A–18D.

Figure 17A:
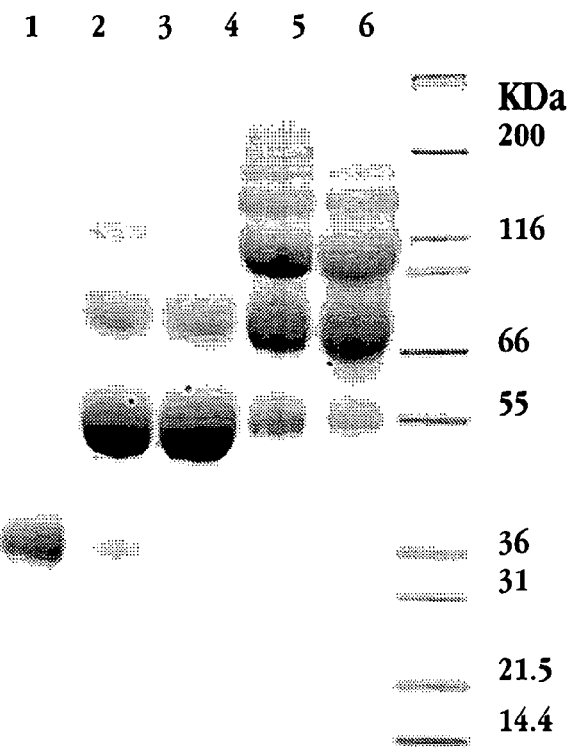
FIGS. 17A–17B are SDS-PAGE profiles of an mPEG$_{12000}$-erythropoietin conjugates after staining for protein detection with Coomassie blue (FIG. 17A) and after iodine staining for PEG detection (FIG. 17B), where in both figures Lane 1 corresponds to EPO control; Lane 2 corresponds to mPEG$_{12000}$-MeDTB-erythropoietin with PEG/protein ratio of 6:1; Lane 3 corresponds to mPEG$_{12000}$-erythropoietin at PEG/protein ratio of 8:1; Lane 4 corresponds to mPEG$_{12000}$-MeDTB-erythropoietin with PEG/protein ratio of 9:1; Lane 5 corresponds to mPEG$_{12000}$-erythropoietin at PEG/protein ratio of 12:1; Lane 6 corresponds to MW protein markers in FIG. 17A and MW PEG markers in FIG. 17B.
Figure 17B:
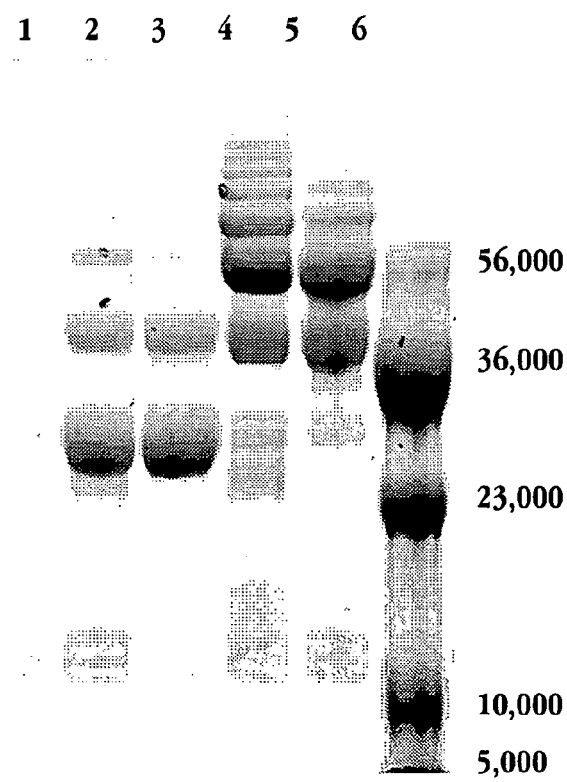
Figure 18A:
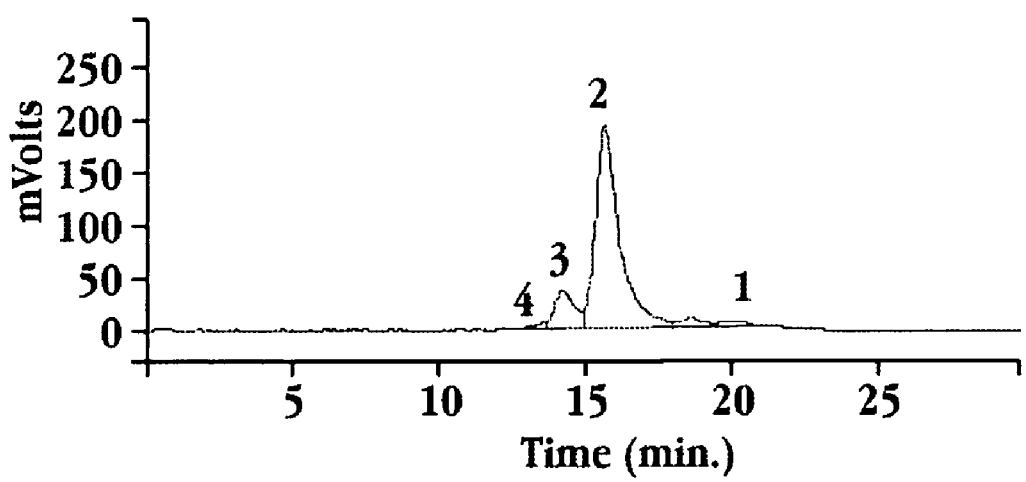
FIGS. 18A–18D are HPLC-SEC traces of mPEG$_{12000}$-erythropoietin conjugates, where
Figure 18B:
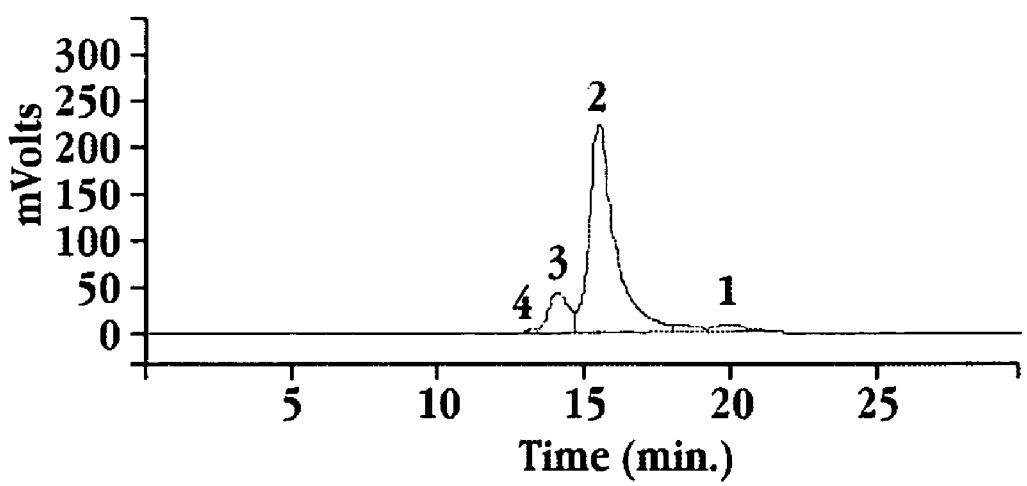

An SDS-PAGE profile of the mPEG-EPO conjugates is shown in FIGS. 17A–17B. The conjugates were stained for protein detection with Coomassie blue (FIG. 17A) and for PEG detection with iodine (FIG. 17B). In both FIGS. 17A–17B, Lane 1 corresponds to EPO control. Lanes 2 and 4 in the figures correspond to mPEG$_{12000}$-MeDTB-erythropoietin with PEG/protein ratio of 6:1 ("lightly PEGylated") and with a PEG/protein ratio of 9:1 ("heavily PEGylated"). Lanes 3 and 5 in both figures correspond to mPEG$_{12000}$-erythropoietin at PEG/protein ratio of 8:1 and 12:1 respectively. Lane 6 corresponds to molecular (MW) protein markers in FIG. 17A and MW PEG markers in FIG. 17B. The gels show formation of PEG-EPO with comparable numbers of PEG moieties after the conjugation with both cleavable and non-cleavable PEG reagents. corresponds to mPEFIGS. 18A–18D are HPLC-SEC traces of the mPEG$_{12000}$-erythropoietin conjugates prepared as described in Example 9. FIG. 18A shows the trace for mPEG$_{12000}$-MeDTB-erythropoietin with a PEG/protein ratio of 6:1. The peak (peak #2) that elutes at 15.6 minutes corresponds to conjugates having a 1:1 PEG/EPO ratio. FIG. 18B shows the trace for the comparative control conjugate of mPEG$_{12000}$-erythropoietin at PEG/protein ratio of 8:1. Peak #2 that elutes at 15.5 minutes corresponds to conjugates having a 1:1 PEG/EPO ratio.

Figure 18C:
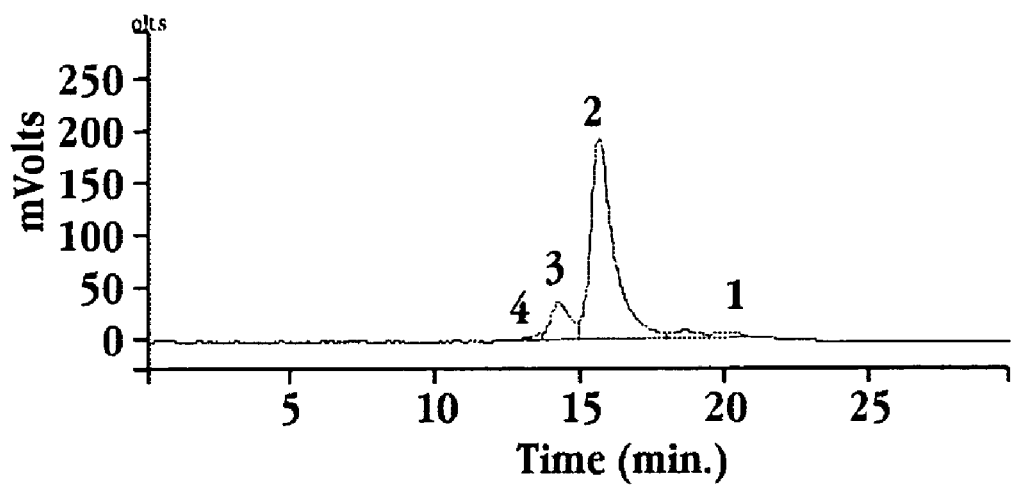
Figure 18D:
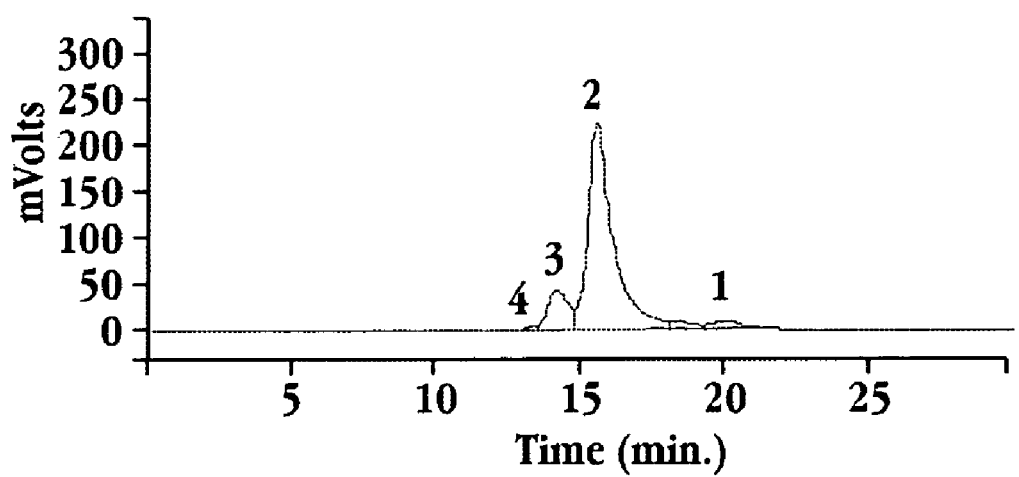

FIGS. 18C–18D show the HPLC-SEC traces for mPEG$_{12000}$-MeDTB-erythropoietin with PEG/protein ratio of 9:1 and for mPEG$_{12000}$-erythropoietin at PEG/protein ratio of 12:1, respectively. The largest peaks (peak nos. 3 and 4) in the traces correspond to conjugates of 2:1 PEG/EPO ratio (peak no. 3) and of PEG/EPO ratios of greater than 2:1, e.g., 3:1, 4:1, 5:1, etc. The traces in FIGS. 18C and 18D when compared to those in FIGS. 18A, 18B show that the higher degree of PEG conjugation in the more "heavily" pegylated conjugates of FIGS. 18C–18D.

Figure 19A:
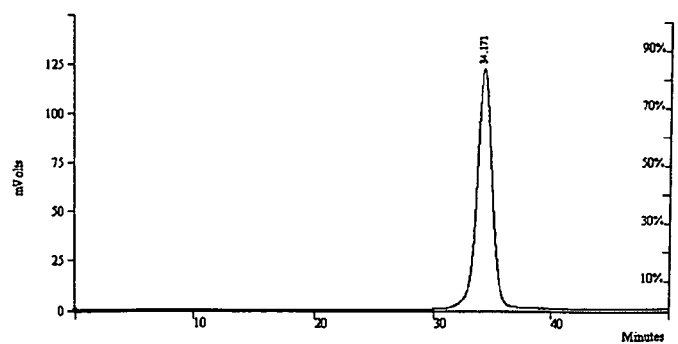
FIGS. 19A–19C are HPLC-SEC traces of erythropoietin (FIG. 19A) and of mPEG$_{30000}$-isopropyl-DTB-erythropoietin conjugates, where
Figure 19B:
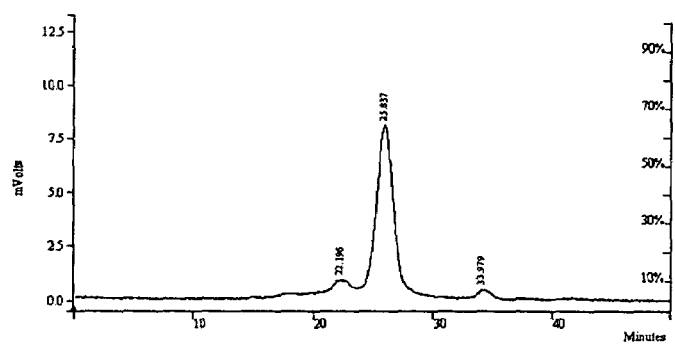
Figure 19C:
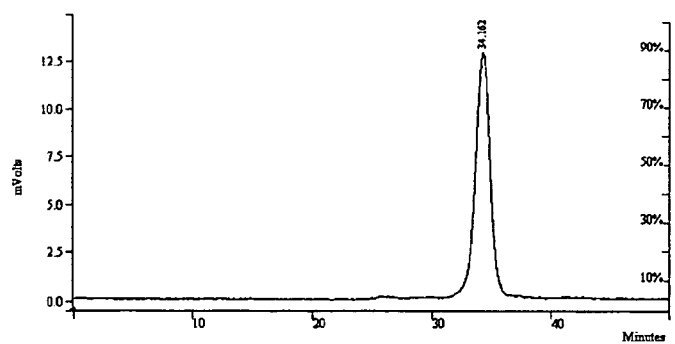

In another study, a PEG-DTB-EPO conjugate was prepared similar to the procedure set forth in Example 9, but with isopropyl ($C_3H_7$) as the R group (see FIG. 11A, R=$C_3H_7$, polypeptide=EPO). This conjugate is referred to as mPEG-iPrDTB-EPO. The conjugate was characterized via HPLC alone and in the presence of 5 mM cysteine, and the HPLC traces are shown in FIGS. 19A–19C. FIG. 19A is a trace for neat erythropoietin and a peak at 34 minutes is observed. FIG. 19B is the trace for mPEG$_{30000}$-isopropyl-DTB-erythropoietin and FIG. 19C for the conjugate after treatment with 5 mM cysteine. Recovery of the neat erythropoietin polypeptide after treatment of the conjugate with a reducing agent is evident from the appearance of the peak at 34 minutes in FIG. 19C.

The examples provided above for lysozyme and erythropoietin are merely exemplary, and polypeptides contemplated for use are unlimited and can be naturally-occurring or recombinantly produced polypeptides. Small, human recombinant polypeptides are preferred, and polypeptides in the range of 10–50 KDa are preferred. Exemplary polypeptides include chemokines, cytokines, such as tumor necrosis factor (TNF), interleukins and interferons, granulocyte colony stimulating factor (GCSF), enzymes, and the like. Viral polypeptides are also contemplated, where the surface of a virus is modified to include one or more polymer chain linked via a cleavable linkage as described herein. Modification of a virus containing a gene for cell transfection would extend the circulation time of the virus and reduce its antigenicity, thereby improving delivery of an exogeneous gene.

It will be appreciated that PEG is merely an exemplary hydrophilic polymer, and that any of the hydrophilic polymers described above are contemplated for use. The molecular weight of the polymer is selected depending on the polypeptide, the number of reactive amines on the polypeptide, and the desired size of the polymer-modified conjugate.

Moreover, in terms of cleaving the DTB linkage, cysteine is a simple thiol, ubiquitously present in physiological environments and an effective cleaving agent for the DTB linkage. However, other thiols, e.g., glutathione, protein-SH, are effective as well. In studies not shown here, PEG-DTB-lysozyme conjugates were cleaved by serum albumin, where the conjugate was incubated in vitro with bovine serum albumin and then analyzed by SDS-PAGE. The profiles of the SDS-PAGE showed successful cleavage of the DTB linkage by bovine serum albumin, as shown in FIGS. 16A–16B.

C. Cleavable Polymer-drug Conjugates

In yet another embodiment of the invention, a conjugate of the form 'polymer-SS—Ar—$CR^3R^4$-amine-containing drug' is contemplated. The conjugate is of the structure described above, where the amine-containing ligand is derived from the amine-containing drug. Modification of therapeutic drugs with PEG is effective to improve the blood circulation lifetime of the drug, to reduce any immunogenicity, and to allow for an enhanced permeability and retention (EPR) effect (Maeda, H. et al., *J. Controlled Release*, 65:271 (2000)). Typically, macromolecular drugs are subject to the EPR effect.

In this embodiment of the invention, in general a polymer-SS—Ar—$CR^3R^4$-amine-containing drug conjugate is prepared according to any of the reaction schemes described above, with modifications as necessary to provide for the particular drug. A wide variety of therapeutic drugs have a reactive amine moiety, and the invention contemplates any such drugs with no limitation. Examples include mitomycin C, bleomycin, doxorubicin, amphotericin B, and ciprofloxacin. FIGS. 20A–20B show the structures for conjugates of mitomycin C and 5-fluorouracil, respectively, modified with a PEG-DTB conjugate. The conjugate with 5-fluorouracil does not require acyl because 5FU by itself as a weak acid is a good leaving group moiety. Example 10A details preparation of an mPEG-MeDTB-mitomycin C conjugate.

Figure 20C:
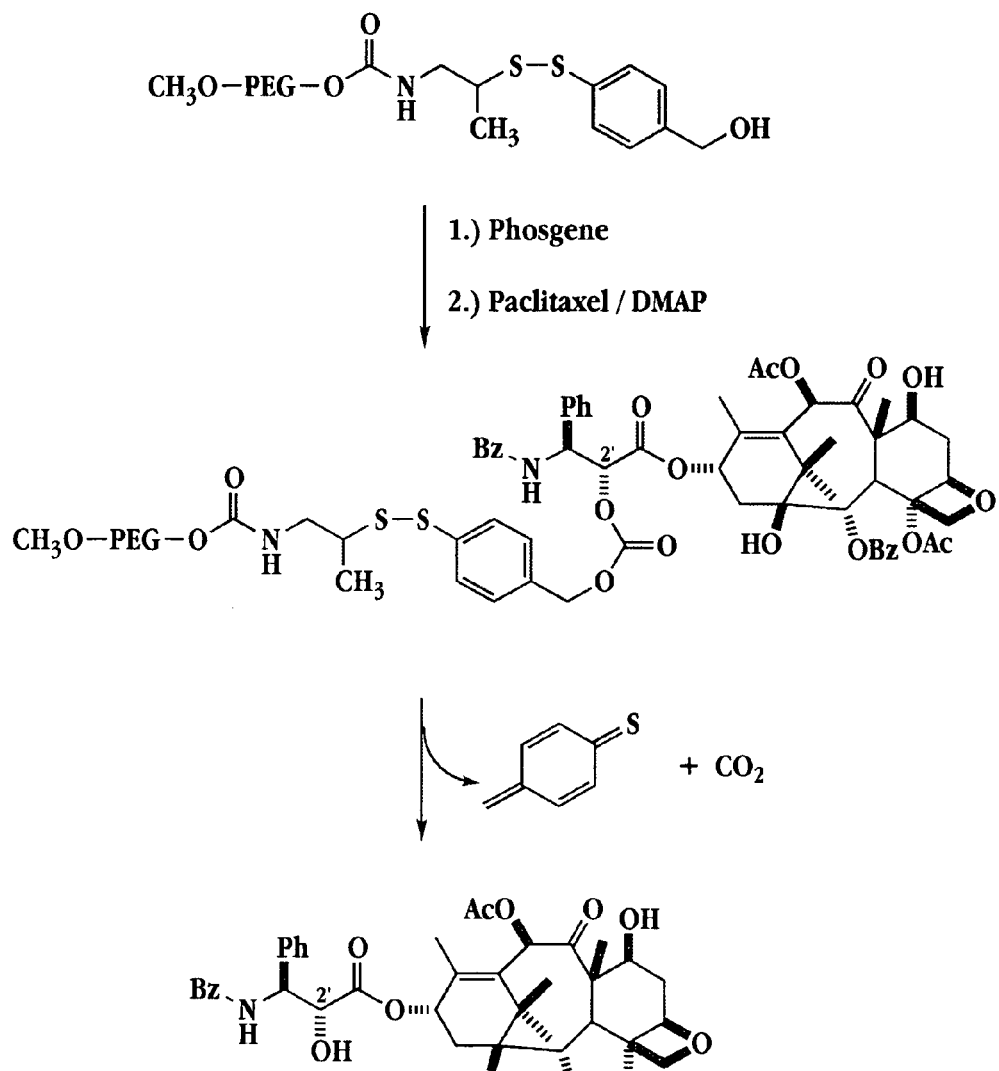
Figure 20D:
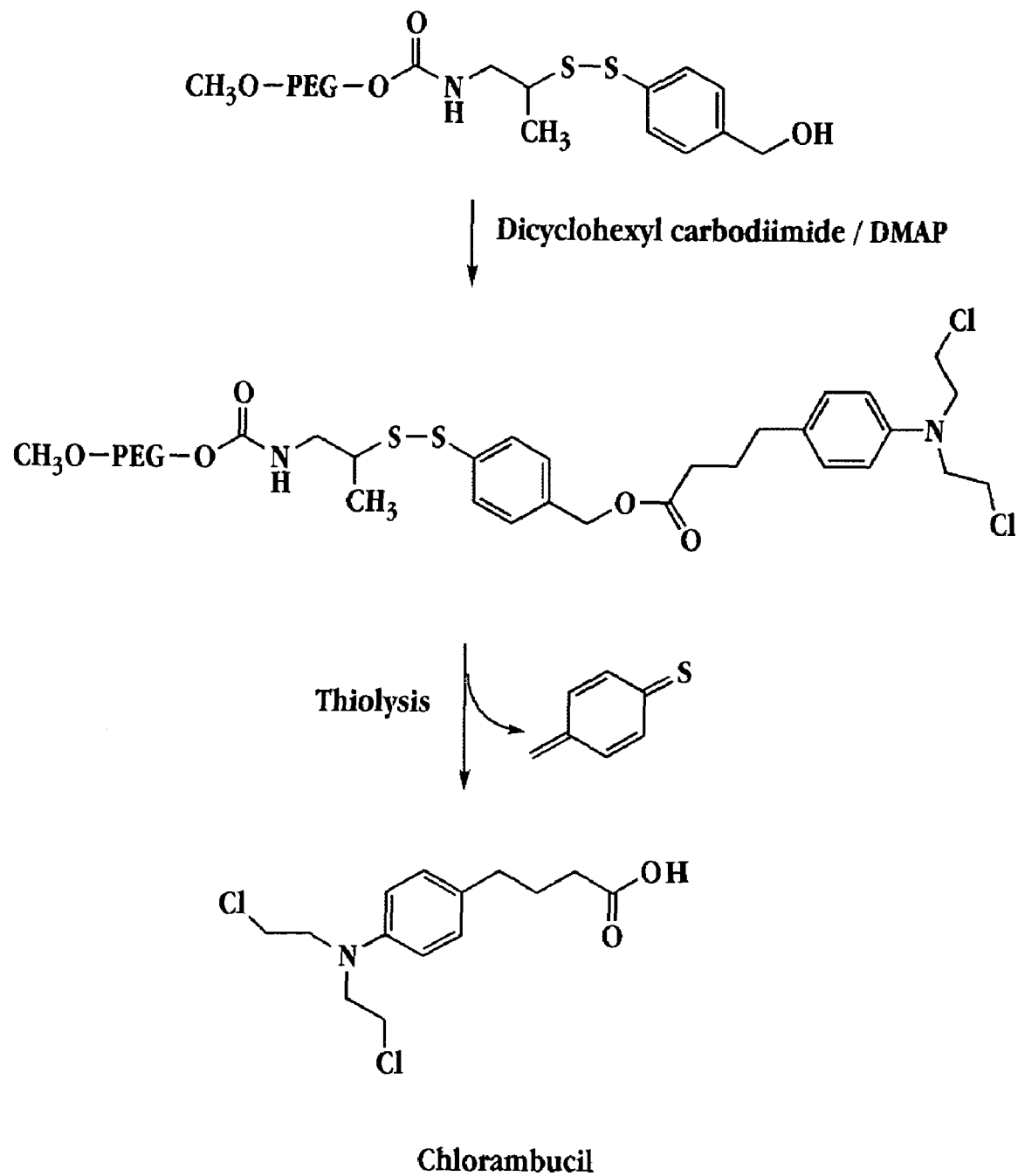

It will be appreciated that the scope of this embodiment is not limited to amine-containing drugs or to attachment of polymer-SS—Ar—$CR^3R^4$ conjugate to an amino moiety. For example, the conjugate can be attached to a drug through a hydroxy moiety or a carboxyl moiety, as FIGS. 20C–2D illustrate. FIG. 20C shows a drug conjugate of paclitaxel, where the cleavable polymer is attached via the 2'-hyroxyl group, and FIG. 20C shows a conjugate of chlorambucil, where the cleavable polymer is attached via a carboxyl moiety. Example 10B details preparation of an mPEG-DTB-paclitaxel drug conjugate.

Figure 21A:
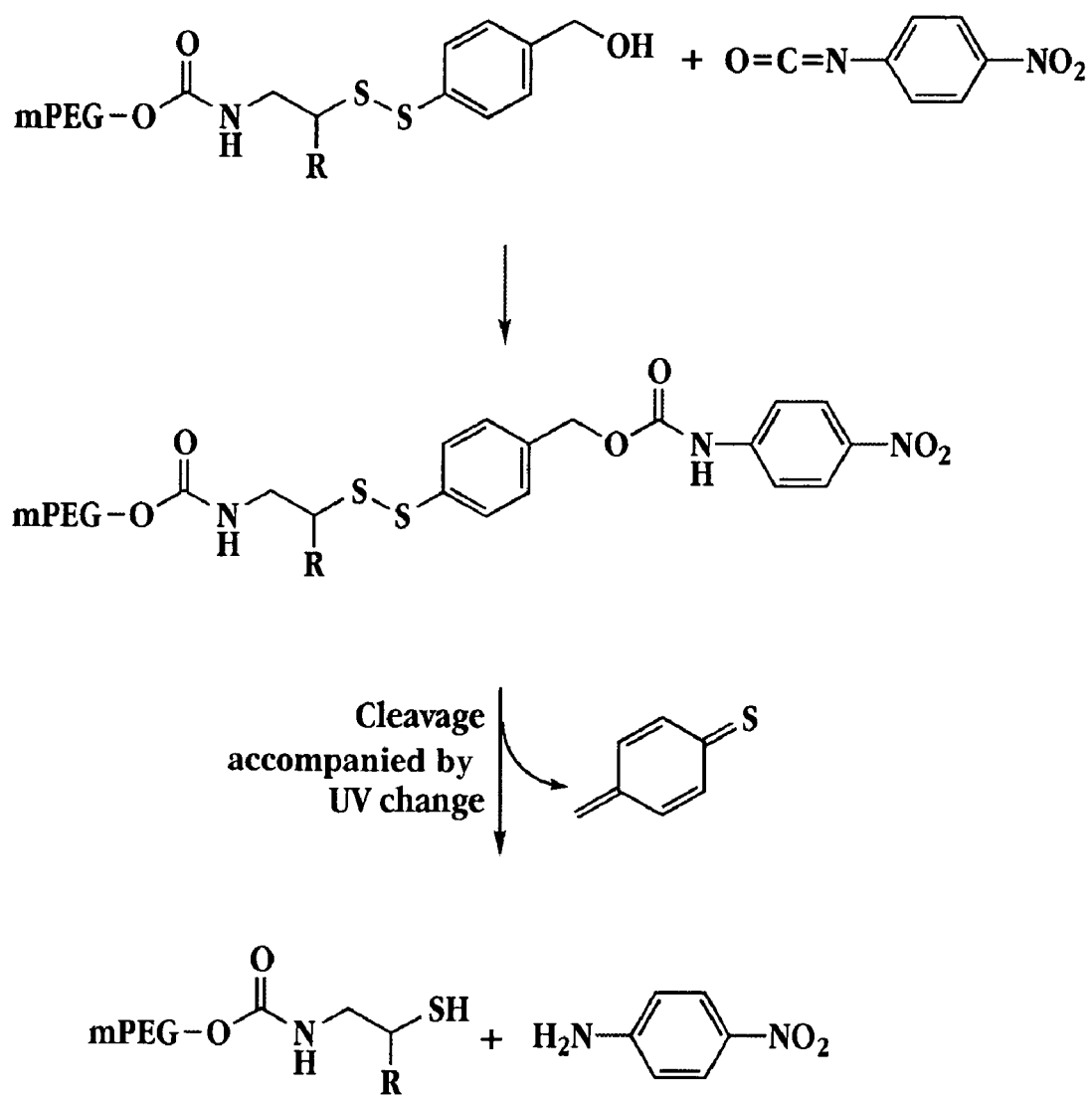
FIG. 21A shows the synthesis of and the decomposition products after thiolytic cleavage of the mPEG-DTB-p-nitroanilide conjugate.
Figure 21B:
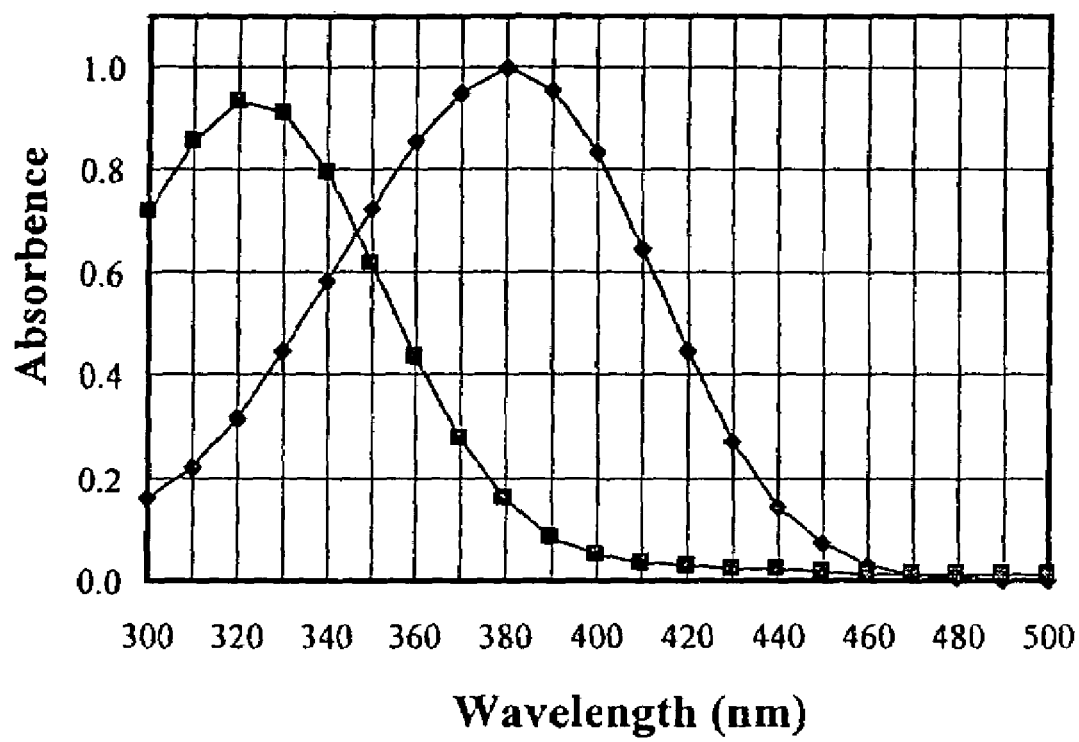
FIG. 21B shows the UV spectra of para-nitroaniline (diamonds) and of mPEG$_{2000}$-DTB-p-nitroanilide conjugate (squares)

In studies performed in support of the invention, the model compound para-nitroaniline (PNA) was incorporated into mPEG-MeDTB-para-nitroaniline to represent a model drug conjugate, as shown in FIG. 21A. Decomposition of the conjugate upon exposure to a reducing agent yields the products shown in the figure, with the drug para-nitroaniline regenerated in an unmodified state. The dramatic difference in UV, as seen in FIG. 21B (para-nitroaniline, diamonds; $mPEG_{2000}$-MeDTB-para-nitroaniline, squares), allows or convenient monitoring of the cleavage reaction and PNA liberation.

Figure 22A:
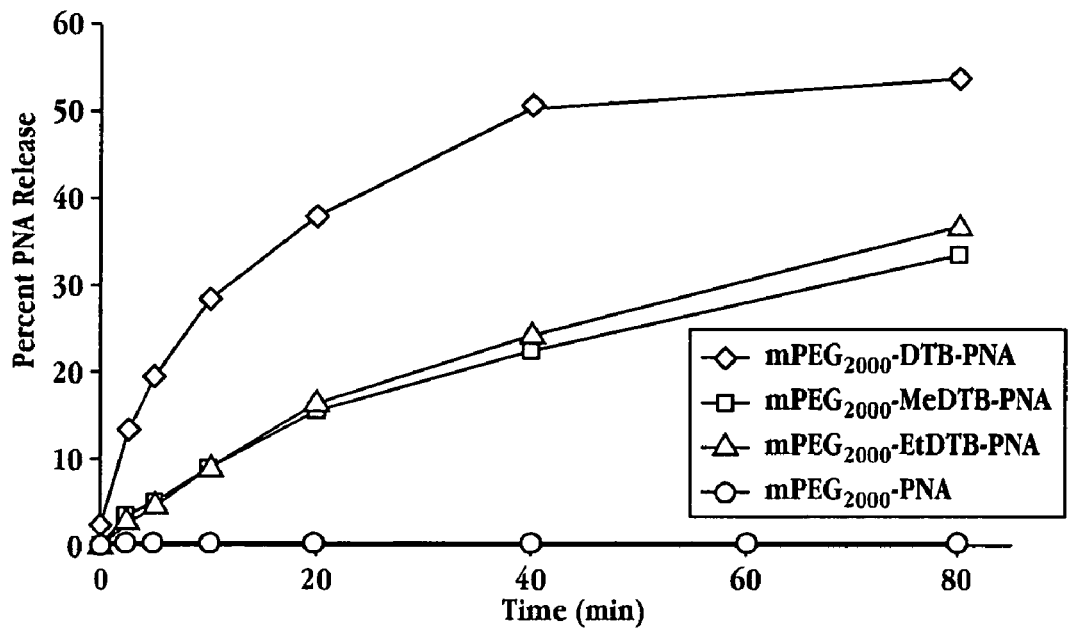
FIG. 22A shows the measured percentage of p-nitroanilide released from mPEG-DTB-para-nitroanilides upon their incubation with 0.15 mM cysteine at pH=7.3 (R=H, diamonds; R=CH$_3$, squares; R=C$_2$H$_5$, triangles) and non-cleavable analog (circles)
Figure 22B:
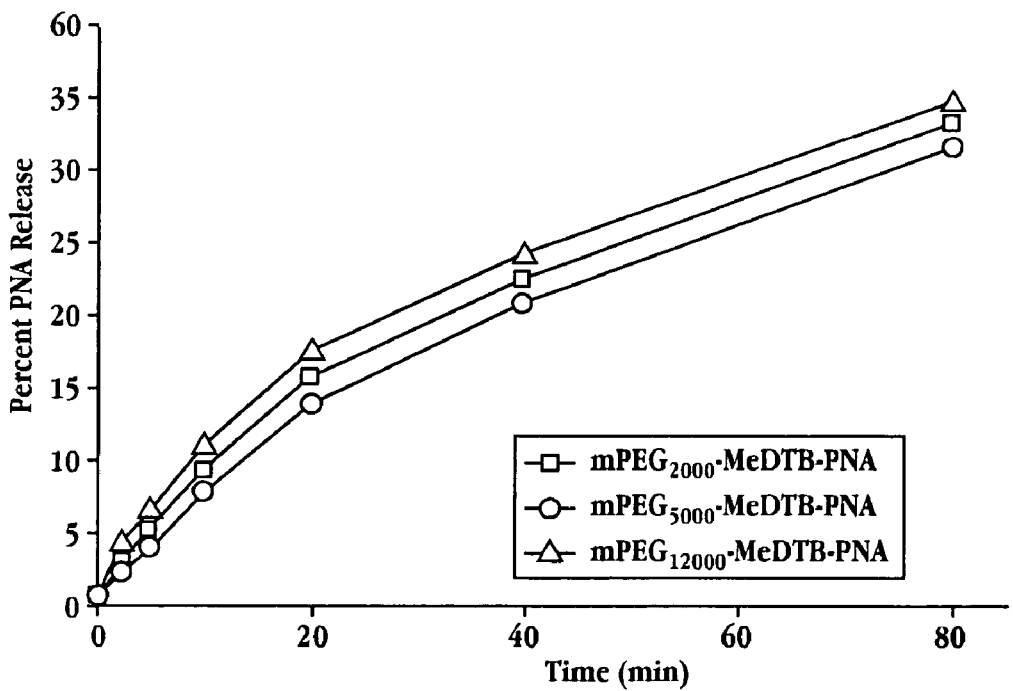
FIG. 22B shows the percent of para-nitroaniline released in vitro as a function of time, in minutes, from mPEG-MeDTB-para-nitroanilide conjugates of different molecular weight (2000 Daltons, squares; 5000 Daltons, circles; 12,000 Daltons, triangles) incubated in the presence of 0.15 mM cysteine at pH 7.3 (structures shown in FIG. 21A).

The mPEG-MeDTB-para-nitroanilide conjugate was incubated in vitro in buffer containing 0.15 mM cysteine, The percent of PNA release at various times is shown in FIGS. 22A–22B. It is apparent from FIG. 22A that mPEG-nitroanilide without the DTB linkage (circles) is not cleaved by cysteine, while the DTB-linked conjugates (DTB=diamond; MeDTB=square; EtDTB=triangle) liberated PNA with rates dependent on the R group (see FIG. 21A). When R=H, the PNA release was fast. Changing R to $CH_3$ (MeDTB, square) slowed down the PNA release, which was essentially of the same rate as for R=$C_2H_5$ (EtDTB, triangle) analog. The molecular weight of PEG had no effect on the rate of cysteine-mediated cleavage of the conjugates.

From the foregoing, it can be seen how various objects and features of the invention are met. The conjugates of the invention comprise an amine-, hydroxy- or carboxyl-containing ligand reversibly joined to a hydrophilic polymer via a cleavable linkage of the form —SS—Ar—$CR^3R^4$— as described above. This linkage, when subjected to mild thiolytic conditions, that are attainable under physiologically, is cleaved to regenerate accordingly the original amine-, hydroxyl-, and carboxyl-containing ligand compounds in their original, fully bioactive form. The rate of cleavage can be controlled by steric hinderance of the disulfide in the linkage and/or by controlling the thiolytic conditions in viva. The conjugates, prior to cleavage of the —SS—Ar—$CR^3R^4$— linkage and attached hydrophilic polymer(s), are provided with an increased blood circulation lifetime, improved stability and reduced immunogenicity. In cases where modification of the drug with the polymer and linkage moeity group causes a reduction or loss of therapeutic activity, activity of the drug is regained after administration and thiolytic cleavage.

III. EXAMPLES

The following examples further illustrate the invention described herein and are in no way intended to limit the scope of the invention.

Materials

All materials were obtained from commercial vendors, such as Aldrich Corporation.

Examples 1

Synthesis of mPEG-DTB-DSPE mPEG-DTB-nitrophenylcarbonate (300 mg, 0.12 mmol, 1.29 eq) was dissolved in $CHCl_3$ (3 mL). DSPE (70 mg, 0.093 mol) and TEA (58.5 µl, 0.42 mmol, 4.5 eq) were added to PEG-solution, and was stirred at 50° C. (oil bath temp). After 15 minutes, TLC showed that the reaction didn't go to completion. Then two portions of TEA (10 µl, and 20 µl), and few portions of mPEG-MeDTB-nitrophenylcarbonate (50 mg, 30 mg, 10 mg) were added every after 10 minutes, until the reaction went to completion. Solvent was evaporated. Product mixture was dissolved in MeOH, and 1 g of C8 silica was added. Solvent was evaporated again. Product containing C8 silica was added on the top of the column, and was eluted with MeOH: $H_2O$ gradient (pressure), MeOH: $H_2O$=30: 70, 60 mL; MeOH: $H_2O$=50: 50, 60 mL; MeOH: $H_2O$=70: 30, 140 mL (starting material eluted); MeOH: $H_2O$=75: 25=40 mL; MeOH: $H_2O$=80: 20, 80 mL (product eluted); MeOH: $H_2O$=85: 15, 40 mL; MeOH: $H_2O$=90: 10, 40 mL; MeOH=40 mL; $CHCl_3$: MeOH: $H_2O$=90: 18: 10, 40 mL. Fractions containing pure product were combined and evaporated to give product as colorless thick liquid. Tertiary butanol (5 mL) was added to it, lyophilized and the dried in vacuo over $P_2O_5$ to give product as white fluffy solid (252 mg, 89% yield).

Both the ortho- and para-$mPEG_{2000}$-DTB-DSPE conjugates prepared in a similar way were purified by silica gel chromatography (methanol gradient 0–10% in chloroform, ≈70% isolated yield) and the structures confirmed by NMR and MALDI-TOFMS. ($^1$H NMR for para conjugate: (d6-DMSO, 360 MHz) δ 0.86 (t, $CH_3$, 6H), 1.22 (s, $CH_2$ of lipid, 56H), 1.57 (m, $CH_2CH_2CO_2$, 4H), 2.50 (2×t, $CH_3$, 4H), 2.82 (t, $CH_2S$, 2H), 3.32 (s, $OCH_3$, 3H), 3.51 (m, PEG, ≈180H), 4.07 (t, PEG-$CH_2$OCONH, 2H), 4.11 & 4.28 (2×dd $CH_2$CH of glycerol, 2H), 4.98 (s, benzyl-$CH_2$, 2H), 5.09 (m, $CHCH_2$ of lipid), 7.35 & 7.53 (2×d, aromatic, 4H) ppm. The ortho conjugate differed only in benzyl and aromatic signals at 5.11 (s, $CH_2$, 2H), and 7.31 (d, 1H), 7.39 (m, 2H) 7.75(d, 1H) ppm.

MALDI-TOFMS produced a distribution of ions spaced at equal 44 Da intervals, corresponding to the ethylene oxide repeating units. The average molecular weights of the conjugates was 3127 and 3139 Da for para and ortho isomers respectively (theoretical molecular weight ≈3100 Da).

The reaction scheme is illustrated in FIG. 2 and FIG. 4B (R=H).

Example 2

Synthesis of mPEG-MeDTB-DSPE

2A. Synthesis of mPEG$_{2000}$-DTB-DSPE

Synthesis of mPEG-DTB-DSPE and the intermediate products according to the reaction scheme illustrated in FIGS. 4A–4B are representative procedures for R=Me and mPEG 5000 Daltons, but are applicable to other molecular weights and R=C$_2$H$_5$.

A. Synthesis of mPEG-nitrophenylcarbonate (mPEG-NPC)

mPEG(5K)-OH (40 g, 8 mmol) was dried azeotropically with toluene (total volume was 270 mL, 250 mL was distilled off by Dean-Stark). Dichloromethane (100 mL) was added to mPEG-OH. para-nitrophenyl chloroformate (2.42 g, 12 mmol, 1.5 eq), and TEA (3.3 mL, 24 mmol, 3 eq) were added to the solution at 4° C. (ice water), while taking precautions against moisture. Light yellow TEA hydrochloride salt was formed. After 15 minutes cooling bath was removed, and the reaction mixture was stirred at room temperature overnight. TLC showed (CHCl$_3$:MeOH: H$_2$O=90:18:2) that the reaction was complete. Solvent was evaporated. The residue was dissolved in ethyl acetate (~50° C.). TEA hydrochloride salt was filtered off and washed with warm ethyl acetate. Solvent was evaporated and the product recrystallized with isopropanol (three times). Yield: 38.2 g (92%). $^1$H NMR (DMSO-d$_6$, 360 MHz) δ 3.55 (s, PEG, 450H); 4.37 (t, PEG-CH$_2$, 2H); 7.55 (d, C$_6$H$_5$, 2H); 8.31 (d, C$_6$H$_5$, 2H).

B. Synthesis of mPEG-oxycarbonylamino-2-propanol

1-Amino-2-propanol (1.1 mL, 14.52 mmol, 3 eq), and TEA (2.02 mL, 14.52 mmol, 3 eq) were added to mPEG (5K)-nitrophenyl carbonate (25 g, 4.84 mmol) in DMF (60 mL) and CH$_2$Cl$_2$ (40 mL). The yellow, clear reaction mixture was stirred at room temperature for 30 minutes. TLC (CHCl$_3$:MeOH=90:10) showed that the reaction went to completion. Solvent (dichloromethane) was evaporated. Isopropanol (250 mL) was added to the product mixture in DMF (60 mL). Product precipitated immediately, and then recrystallized with iPrOH (three times). Yield: 22.12 g (90%). $^1$H NMR (DMSO-d$_6$, 360 MHz) δ 0.98 (d, CH$_3$CH (OH)CH$_2$, 3H); 3.50 (s, PEG, 180H); 4.03 (t, PEG-CH$_2$, 2H); 4.50 (d, CH$_3$CHOH, 1H); 7.0 (t, mPEG-OCONH).

C. Synthesis of mPEG-oxycarbonylamino-2-propyl methane sulfonate mPEG(5K)-oxycarbonyl-2-amino propanol (22.12 g, 4.34 mmol) was dried azeotropically with toluene (45 mL). Dichloromethane (60 mL) was added to it. Methane sulfonyl chloride (604.6 µl, 7.81 mmol, 1.8 eq) and TEA (3.93 mL, 28.21 mmol, 6.5 eq) were added to the solution at 0° C. while maintaining stirring and taking precautions against moisture. After 30 minutes, cooling bath was removed, and the reaction mixture was stirred at room temperature for 16 hours, and then evaporated. Ethyl acetate was added to remove TEA salts. The product was recrystallized with isopropanol (three times). Yield: 20.27 g (90%). $^1$H NMR (DMSO-d$_6$, 360 MHz) δ 1.27 (d, CH$_3$CHOSO$_2$CH$_3$, 3H); 3.162 (s, CH$_3$O$_2$SOCH, 3H); 3.50 (s, PEG, 180H); 4.07 (t, PEG-CH$_2$, 2H); 4.64 (q, CH$_3$CHOH, 1H); 7.43 (t, mPEG-OCONH).

D. Synthesis of mPEG-oxycarbonyl-2-aminopropyl-S-triphenylmethyl

Sodium hydride (377 mg, 9.4 mmol, 4.75 eq) was added to anhydrous toluene (60 mL) at 0° C. (on ice water). After 5 minutes, triphenylmethanethiol (3.92 g, 14.6 mmol, 7.15 eq) was added to the solution. After an additional 10 minutes, mPEG-oxycarbonyl-2-aminopropyl-methane sulfonate (10.27 gm, 1.98 mmol) was added to the reaction mixture. The solution turned yellow. After 45 minutes, TLC (CHCl$_3$:MeOH: H$_2$O=90:18:2) showed that the reaction went to completion. Acetic acid (445.57 µL, 7.42 mmol, 3.75 eq) was added to the reaction mixture to neutralize excess of sodium hydride. The solution became thick and whitish. Solvent was evaporated and the residue treated with warm ethyl acetate (30 mL) and isopropanol (7 mL). The precipitate was filtered off. Then the product was precipitated by cooling, and then recrystallyzed with isopropanol/tert-butyl alcohol (100 mL/20 mL). Yield: 8.87 g (84%). $^1$H NMR (DMSO-d$_6$, 360 MHz) δ 0.74 (d, CH$_3$CHSC(C$_6$H$_5$)$_3$, 3H), 3.50 (s, PEG, 180H), 4.0 (t, PEG-CH$_2$, 2H), 4.64 (q, CH$_3$CHOH, 1H); 7.49 (t, mPEG-OCONH); 7.20–7.41 (m, SC(C$_6$H$_5$)$_3$, 15H).

E. Synthesis of mPEG-oxycarbonyl-2-aminopropyl-S-sulfenyl carbomethoxy Derivative mPEG(5K)-oxycarbonyl-2-aminopropyl-S-triphenylmethyl (8.87 g, 1.65 mmol) was dissolved in TFA/CH$_2$Cl$_2$(10 mL/10 mL) at 0° C. Under vigorous stirring, methoxy carbonylsulfenyl chloride (185.5 µL, 1.99 mmol, 1.2 eq) was added to the solution. The reaction mixture was stirred at room temperature for 15 minutes. TLC (CHCl$_3$:MeOH=90: 10) showed that the reaction was complete. Solvents were evaporated. The product mixture was recrystallized with isopropanol:tert-butyl alcohol (80 mL: 20 mL) two times. Tertiary butanol (5 mL) was added to the product, which was then lyophilized and dried in vacuo over P$_2$O$_5$ to give product as white fluffy solid (8.32 g, 97% yield). $^1$H NMR (DMSO-d$_6$, 360 MHz) δ 1.17 (d, CH$_3$CHSSCOOCH$_3$, 3H); 3.42 (s, PEG, 180H); 3.84 (s, CH$_3$OCOSSCH, 3H); 4.05 (t, mPEG-CH$_2$, 2H); 7.38 (t, mPEG-OCONH, 1H).

F. Synthesis of mPEG-oxycarbonyl-2-aminopropyl dithiobenzyl alcohol (mPEG-MeDTB-OH)

mPEG(5K)-S-Scm (8.32 g, 1.6 mmol) was dissolved in dry methanol (20 mL), and chloroform (2.5 mL). A solution of mercapto benzyl alcohol (592 mg, 4 mmol, 2.5 eq) in dry methanol (2 mL) was added to the solution. The reaction mixture was stirred at room temperature for 18 h. Solvent was evaporated, product mixture was recrystallized with ethyl acetate/isopropanol, 30 mL/100 mL (3 times). NMR showed ~16% product was formed. So, another portion of mercapto benzyl alcohol (322 mg, 2.18 mmol, 1.8 eq) in MeOH (2 mL) was added dropwise to the product mixture in MeOH/CHCl$_3$ (24 mL/l mL) at 0° C. (ice water). After addition (~10 minutes) completion, ice bath was removed, and the reaction mixture was stirred at room temperature for 24 h. TLC (CHCl$_3$:MeOH:H$_2$O=90:18:2) showed that the reaction was complete. Solvent was evaporated, and then product mixture was recrystallized with ethyl acetate/isopropanol, 30 mL/100 mL. Yield: 7.25 g, (94%). $^1$H NMR (DMSO-d$_6$, 360 MHz) δ 1.56 (d, CH$_3$CHSSC$_6$H$_5$CH$_2$OH, 3H); 3.29 (CH$_3$O-PEG, 3H); 3.50 (s, PEG, 450H); 4.03 (t, mPEG-CH$_2$, 2H); 4.46 (d, HOCH$_2$C$_6$H$_5$, 2H); 5.16 (t, HOCH$_2$C$_6$H$_5$, 1H); 7.30 (d, C$_6$H$_5$, 2H); 7.40 (br t, mPEG-OCONH, 1H); 7.50 (d, C$_6$H$_5$, 2H);

G. Synthesis of mPEG-oxycarbonyl-2-aminopropyl dithiobenzyl nitrophenylcarbonate (mPEG-MeDTB-NPC)

mPEG(5K)-oxycarbonyl-2-aminopropyl-dithiobenzyl alcohol (6.75 9, 1.27 mmol) was dissolved in CHCl$_3$ (30 mL), p-nitrophenyl chloroformate (513 mg, 2.54 mmol, 2 eq) was added to it at 0° C. (ice water). After 5 minutes triethylamine (531 µL, 3.81 mmol, 3 eq) was added. After 30 minutes the ice bath was removed, and the reaction mixture was stirred at room temperature overnight. Solvent was evaporated. The product mixture was dissolved in ethyl acetate. TEA salt was filtered off, and then solvent was evaporated. Then the product mixture was recrystallized with ethyl acetate/isopropanol, 30 mL/100 mL (three times). Yield: 6.55 g (94%). $^1$H NMR (DMSO-$d_6$, 360 MHz) δ 1.17 (d, $CH_3CHSSC_6H_5$, 3H); 3.24 ($CH_3$O-PEG, 3H); 3.40 (s, PEG, 180H); 4.03 (br t, mPEG-$CH_2$, 2H); 5.28 (S, $C_6H_5CH_2OCO$, 2H); 7.45–8.35 (m, $C_6H_5$)$_2$, 8H)

H. Synthesis of mPEG$_{5000}$-MeDTB-DSPE Conjugate mPEG-MeDTB-nitrophenylcarbonate (766 mg, 0.14 mmol, 1.29 eq) was dissolved in CHCl$_3$ (5 mL). DSPE (70 mg, 0.093 mol) and TEA (58.5 µL, 0.42 mmol, 4.5 eq) were added to the solution, and was stirred at 50° C. (oil bath temp). After 20 minutes, TLC showed that the reaction didn't go to completion. More mPEG-MeDTB-nitrophenylcarbonate (total 1239 mg, 0.23 mmol, 2.47 eq) and 1-hydroxybenztriazole (HOBt) (25 mg, 0.19 mmol, 2 eq) were added. After 20 minutes, TLC (CHCl$_3$:MeOH:H$_2$O=90:18:2, with molybdenum and ninhydrin) showed that the reaction was complete. Solvent was evaporated. Product mixture was dissolved in warm (42° C.) ethyl acetate. It was a cloudy solution (TEA salt precipitated). The solution was filtered, and solvent was evaporated. MeOH, and 2 g of C8 silica was added to the product mixture. Solvent was evaporated again. Product containing C8 silica was added on the top of the column, and was eluted with MeOH: H$_2$O gradient (pressure), MeOH: H$_2$O 30: 70, 100 mL; MeOH H$_2$O 50: 50, 100 mL; MeOH H$_2$O 70: 30, 250 mL (starting material eluted); MeOH H$_2$O 75: 25=40 mL; MeOH H$_2$O 80: 20, 200 mL (product eluted); MeOH=100 mL; CHCL$_3$: MeOH: H$_2$O=90: 18: 2, 100 mL; CHCL$_3$: MeOH H$_2$O=75: 36: 6, 100 mL. Fractions containing pure product were combined and evaporated to give product as colorless thick liquid. Tertiary butanol (5 mL) was added to it, lyophilized and then dried in vacuo over P$_2$O$_5$ to give product as white fluffy solid (467 mg, 83% yield). $^1$H NMR (DMSO-$d_6$, 360 MHz) δ 0.83 (d, 2(CH$_3$), 3H); 1.16 (d, $CH_3CHSSC_6H_5$, 3H); 1.21 (s, 28(CH$_2$, 56H); 1.47 (br m, $CH_2CH_2$CO, 4H); 2.23 (2×t, $CH_2CH_2$CO, 4H); 3.50 (s, PEG, 180H); 4.04 (br t, mPEG-$CH_2$, 2H); 4.05 (trans d, PO$_4$CH$_2$CHCH$_2$, 1H); 4.24 (cis d, PO$_4$CH$_2$CHCH$_2$, 1H); 4.97 (s, $C_6H_5CH_2$OCO-DSPE, 2H); 5.03 (br s, (PO$_4$CH$_2$CH, 1H); 7.32 (d, $C_6H_5$, 2H) 7.53 (d, $C_6H_5$, 2H); 7.52 (br s, mPEG-OCONH, 1H). MALDI-TOFMS produced a bell shaped distribution of ions spaced at equal 44 Da intervals, corresponding to the ethylene oxide repeating units. The average molecular mass of the conjugate and mPEG-thiol (mostly cleaved disulfide) is 6376 and 5368 Da (theoretical molecular mass ~6053, and 5305 Daltons).

2B. Synthesis of mPEG$_{2000}$-ethylDTB-DSPE mPEG-oxycarbonylamino-2-butyl dithiocarbonyl methoxide (S—Scm derivative, 2 g, 0.90 mmol) was dissolved in dry methanol (8 mL). At the beginning the solution was cloudy, but after 5 minutes it became a clear solution. Mercaptobenzyl alcohol (265.2 mg, 1.79 mmol, 2 eq) was added to the PEG-solution. The reaction mixture was stirred at room temperature for 30 hours. Ether (70 mL) was added to the reaction solution to precipitate the product, and kept at 4° C. overnight. The white solid was filtered and recrystallized with ethyl acetate/ether, 30 mL/70 mL. Yield: 1.96 g, (94%). $^1$H NMR (DMSO-$d_6$, 360 MHz) δ0.86 (d, $CH_3CH_2CHSSC_6H_5CH_2OH$, 3H); 1.42 (p, $CH_3CH_2CHSSC_6H_5CH_2OH$, 1H); 1.64 (p, $CH_3CH_2CHSSC_6H_5CH_2OH$, 1H); 3.51 (s, PEG, 180H); 4.03 (t, mPEG-CH$_2$, 2H); 4.47 (d, HOCH$_2C_6H_5$, 2H); 5.20 (t, HOCH$_2C_6H_5$, 1H); 7.31 (d, $C_6H_5$, 2H); 7.42 (br t, mPEG-OCONH, 1H); 7.49 (d, $C_6H_5$, 2H). The resulting mPEG-EtDTB-OH was activated to form mPEG-EtDTB-NPC as described in Example 2A(G) above.

N-hydroxy-s-norbornene-2,3-dicarboxylic acid imide (HONB) (48 mg, 0.269 mmol) was added to DSPE (55 mg, 0.073 mmol) in CHCl$_3$ (3 mL) at 50° C. (oil bath temperature). After 3–4 minutes it became a clear solution. Then mPEG-EtDTB-nitrophenylcarbonate (334 mg, 0.134 mmol) was added, followed by triethylamine (TEA, 45 µl, 0.329 mmol). After 20 minutes TLC (CHCl$_3$: MeOH: H$_2$O=90: 18:2) showed that the reaction went to completion (molybdenum and ninhydrin sprays). Solvent was evaporated. Product mixture was dissolved in methanol, mixed with C8 silica (1 g) and striped of the solvent by rotary evaporation. The solid residue was added on the top of the C8-column, which was then eluted with MeOH:H$_2$O gradient (pressure), MeOH:H$_2$O=30:70, 60 mL; MeOH:H$_2$O=50:50, 60 mL; MeOH:H$_2$O=70: 30, 140 mL; MeOH:H$_2$O=75:25=140 mL (starting material eluted); MeOH:H$_2$O=80:20, 80 mL; MeOH:H$_2$O=90:10, 140 mL (product eluted); MeOH=40 mL; CHCl$_3$:MeOH:H$_2$O=90:18:10, 40 mL. Fractions containing pure product were combined and evaporated to give product as colorless thick liquid. Tertiary butanol (5 mL) was added, lyophilized and then dried in vacuo over P$_2$O$_5$ to give product as white fluffy solid (175 mg, 78% yield). $^1$H NMR (DMSO-$d_6$, 360 MHz) δ 0.85 (d, 2(CH$_3$), 6H; d, $CH_3CHSSC_6H_5$, 3H); 1.22 (s, 28(CH$_2$), 56H); 1.49 (br m, $CH_2CH_2$CO, 4H); 2.24 (2×t, $CH_2CH_2$CO, 4H); 3.50 (s, PEG, 180H); 4.04 (br t, mPEG-CH$_2$, 2H); 4.08 (trans d, PO$_4$CH$_2$CHCH$_2$, 1H); 4.27 (cis d, PO$_4$CH$_2$CHCH$_2$, 1H); 4.98 (s, $C_6H_5CH_2$OCO-DSPE, 2H); 5.06 (br s, (PO$_4$CH$_2$CH, 1H); 7.34 (d, $C_6H_5$, 2H); 7.53 (d, $C_6H_5$, 2H); 7.55 (br s, mPEG-OCONH, 1H).

Example 3

Alternative Synthesis of
mPEG-S-Sulfenylcarbomethoxy (Scm) Derivatives
(R=CH$_3$ or R=C$_2$H$_5$)

The reaction scheme is illustrated in FIG. 5. Synthesis of R-substituted aminoethanethiols from amino alcohols was accomplished according to Owen, T. C., *J. Chem. Soc.*, C:1373 (1967).

1. Synthesis of methoxycarbonyldisulfanyl-1-2-propyl-ammonium chloride

Methoxycarbonyldisulfanyl-2-propylammonium chloride was prepared by reacting methoxycarbonylsulfenyl chloride with equivalent amount of amino-2-propanethiol hydrochloride according to the previously published procedures (Brois, *J Am Chem Soc* 92:7629 (1970); Koneko, et al., *Bioconjung Chem* 2:133–141, (1991)). Amino-2-propanethiol hydrochloride (1.83 ml, 19.44 mmol) in methanol (15 ml) was added dropwise (~1.0 ml/minute) to a cold (4° C.) solution of methoxycarbonylsulfenyl chloride (Scm-Cl, 2.5 g, 19.6 mmol) in methanol (15 ml). The solution was stirred at room temperature for 3 h and then rotary evaporated. The residue was taken up in acetone and then stripped of the solvent two more times resulting in formation of white solid. Silica-C8 (1 g) was added to the product solution in MeOH, which was then evaporated. The product-containing residue was added to the top of the C8-silica column, and was eluted with water under N$_2$ pressure. Fractions containing pure product were combined, evaporated, and lyophilized from tert-butanol (5 ml). It was further dried in vacuo over P$_2$O$_5$ to give product as white solid (2 g, 47% yield): $^1$H MNR δ: 1.30 (d, CH$_3$CH, 3H), 2.94 (br t, $CH_2NH_3Cl$, 2H), 3.37 (q, $CH_3CHCH_2NH_3Cl$, 1H), 3.88 (s, $CH_3OCO$, 3H), 8.21 (br s, $CH_3CHCH_2NH_3Cl$, 3H) ppm.

2. Synthesis of mPEG5000-oxycarbonyl-2-aminopropyl-S-sulfenylcarbomethoxy (mPEG-S-Scm) mPEG-oxycarbonyl-2-aminobutyl-S-Scm.

MPEG-OH (15 g, 3 mmol) was dried by azeotropic removal of toluene (100 ml). The solution was cooled, diluted with dichloromethane (40 ml) and treated with toluene solution of phosgene (10 ml, 19.3 mmol) at 4° C. The ice bath was removed and the reaction was stirred at room temperature overnight, and then evaporated to dryness leaving solid mPEG-chloroformate. Methoxycarbonyldisulfanyl-2-propylammonium chloride (686.7 mg, 3.15 mmol) and TEA (836.3 µl, 6 mmol) were added to the mPEG-chloroformate in chloroform (30 ml). The reaction mixture was stirred at room temperature overnight and then evaporated. The residue was taken up in warm ethyl acetate (150 ml) and filtered to remove the TEA hydrochloride. The solvent was removed and the product was purified by recrystallization from ethyl acetate/iso-propanol (100/100 ml, three times) and dried in vacuo over $P_2O_5$ yielding white solid (14.5 g, 93%). $^1H$ NMR δ: 1.18 (d, $CH_3CHSS_2$, 3H), 3.10 (m, $CH_2NH$, 2H), 3.24 (s, $CH_3O$, 3H), 3.50 (s, PEG, ~520H), 3.86 (s, $CH_3OCOSSCH$, 3H), 4.05 (t, $OCOCH_2$, 2H), 7.38 (t, OCONH, 1H) ppm.

Example 4

Synthesis of mPEG-DTB-lipid According to FIG. 6A 1, 2-distereoyl-sn-glycerol (500 mg, 0.8 mmol) was dried azeotropically with benzene (3 times). Para-nitrophenyl chloroformate (242 mg, 1.2 mmol, 1.5 eq), dimethylaminopyridine (DMAP) (10 mg, 0.08 mmol, 0.1 eq), and TEA (334.5 µl, 2.4 mmol, 3 eq) were added to 1,2-distereoyl glycerol in $CHCl_3$ (5 mL). The reaction mixture was stirred at room temperature for 2 h. TLC (Toluene: ethyl acetate=7:3) showed that the reaction was complete. Then the product mixture was extracted with 10% citric acid to remove dimethylaminopyridine (DMAP), washed with acetonitrile (3 mL, 4 times) to remove excess of p-nitrophenyl chloroformate. Pure product was dried in vacuo over $P_2O_5$. Yield: 557 mg(88%). %). $^1H$ NMR ($CHCl_3$, 360 MHz) δ 0.88 (t, end $CH_3$, 6H); 1.25 (s, 28×$CH_2$, 56H); 1.58 (m, $CH_2CH_2CO$, 4H); 2.34 (2×t, $CH_2CO$, 4H); 4.22 (trans d, $CH_2OCOC_{17}H_{35}$, 1H); 4.35 (m, $OCOOCH_2CH$, 2H); 4.51 (cis d, $CH_2OCOC_{17}H_{35}$, 1H); 5.37 (m, $OCOOCH_2CH$, 1H); 7.39 (d, $C_6H_5$, 2H); 8.28 (d, $C_6H_5$, 2H).

Ethylene diamine (42 µl, 0.63 mmol, 5 fold excess), and pyridine (200 µl, were added in $CHCl_3$ (1 mL). 2-disteroyl-sn-p-nitrophenyl carbonate (100 mg, 0.13 mmol) was dissolved in $CHCl_3$ (1 mL) and added dropwise to ethylene diamine solution with a pasteur pipette at 0° C. (ice water) and continued overnight (16 h). TLC ($CHCl_3$:MeOH: $H_2O$ 90:18:2, and $CHCl_3$: MeOH=90:10) showed that the reaction was complete. Solvent was evaporated to remove pyridine. Then the product mixture was dissolved in $CHCl_3$, loaded onto the column (Aldrich, Silica gel, 60° A, 200–400 mesh), and eluted with $CHCl_3$:$CH_3COCH_3$, and $CHCl_3$:MeOH gradient, $CHCl_3$:$CH_3COCH_3$=90:10, 60 mL (upper spot eluted); $CHCl_3$:NeOH=90:10, 60 mL (product eluted). Fractions containing pure product were combined and evaporated. Tert-butanol was added and dried in vacuo over $P_2O_5$. Yield: 64 mg (75%). $^1H$ NMR (DMSO-$d_6$, 360 MHz) δ 0.83 (t, end $CH_3$, 6H); 1.22 (s, 28×$CH_2$, 56H); 1.51 (m, $CH_2CH_2CO$, 4H); 2.25 (2×t, $CH_2CO$, 4H); 2.83 (m, $H_2NCH_2CH_2NH$, 2H); 3.21 (m, $H_2NCH_2CH_2NH$, 2H); 4.10–4.14 (m & cis d, $COOCH_2CHCH_2$, 4H); 5.17 (m, $OCOOCH_2CH$, 1H); 7.78 (m, $H_2NCH_2CH_2NH$, 2H).

mPEG-MeDTB-nitrophenylchloroformate (400 mg, 0.162 mmol, 2.2 eq) was dissolved in $CHCl_3$ in (2 mL). 1,2-steroyl-sn-ethylene amine (51 mg, 0.075 mmol) and TEA (37 µl, 0.264 mmol, 3.52 eq) were added to the solution. Then the reaction mixture was stirred at 45° C. for 20 minutes. TLC ($CHCl_3$:MeOH:$H_2O$=90:18:2, and $CHCl_3$:MeOH=90:10) showed that the reaction went to completion. Solvent was evaporated. The product mixture was dissolved in methanol. 2 g of C8 silica was added and then solvent was evaporated. C8 silica containing product mixture was added on the top of the C8 column ((Supelco, Supel clean. Lot no. SP0824), and was eluted with MeOH: $H_2O$ gradient (pressure), MeOH:$H_2O$=60:40, 40 mL; MeOH:$H_2O$=70:30, 80 mL (starting material eluted); MeOH:$H_2O$=80:20, 40 mL; MeOH:$H_2O$=90:0=20 mL; $CHCl_3$: MeOH:$H_2O$=5:80:15, 20 mi; $CHCl_3$:MeOH:$H_2O$=90:18:10, 40 mL (product eluted). Fractions containing pure product were combined and evaporated to give product as colorless thick liquid. Tertiary butanol (5 mL) was added and the solution was lyophilized and then dried in vacuo over $P_2O_5$ to give product as white solid (200 mg, 89% yield). $^1H$ NMR (DMSO-$d_6$, 360 MHz) δδ 0.83 (t, end $CH_3$, 6H); 1.22 (s, 28×$CH_2$, 56H); 1.48 (m, $CH_2CH_2CO$, 4H); 2.25 (2×t, $CH_2CO$, 4H); 3.10 (m, $HNCH_2CH_2NH$, 4H); 3.50 (s, PEG, 180H); 4.04 (t, mPEG-$CH_2$, 2H); 4.09 (trans d, $COOCH_2CHCH_2$, 1H); 4.25 (cis d, $COOCH_2CHCH_2$, 1H); 4.98 (s, $C_6H_5CH_2OCO$, 2H); 5.23 (m, $COOCH_2CHCH_2$, 1H); 7.18 (m, $NHCH_2CH_2NH$, 2H); 7.33 (d, $C_6H_5$, 2H); 7.38 (m, mPEG-OCONH, 1H); 7.52 (d, $C_6H_5$, 2H).

Example 5

In vitro Cleavage of mPEG-DTB-DSPE Compound

Ortho-mPEG-DTB-DSPE and para-mPEG-DTB-DSPE (prepared as described in Examples 1 and 2) were added to a buffered aqueous solution (pH 7.2) in the presence and absence of cysteine. Disappearance of the conjugates was monitored by HPLC (Phenomenex $C_8$ Prodigy, 4.6×50 mm column, detection at 277 nm, mobile phase methanol/water 95:5 with 0.1% trifluoroacetic acid at 1 mL/min). The results are illustrated in FIG. 7 where the ortho-conjugates are represented by the open symbols and the para-conjugates by the closed symbols.

Example 6

In vitro Cleavage of Various mPEG-DTB-DSPE Conjugate in Liposomes

A. Liposome Preparation

The lipids dioleoyl phosphatidylethanolamine (DOPE) and ortho- or para-mPEG-DTB-DSPE (prepared as described in Examples 1, 2, and 4, mPEG MW=2000 Daltons) were dissolved at 97:3 molar ratio in chloroform/methanol 1:1. The solvent was removed by rotary evaporation to form a dried lipid film. The lipid film was hydrated with an aqueous solution containing 30 mM each of the fluorophores p-xylene-bis-pyridinium bromide and trisodium 8-hydroxypyrenetrisulfonate was hydrated with aqueous buffer to from liposomes that were sized via extrusion to an average diameter of 100 nm.

B. In vitro Characterization

The liposomes were incubated in HEPES buffer, pH 7.2, at 37° C. in the presence of cysteine at concentrations ranging from 15 µM to 15 mM. Percent of released dye was determined as the increase in sample fluorescence ($\lambda_{em}$=512 nm, $\lambda_{ex}$=413 nm—pH-independent isobestic point) over that of the preincubation sample (zero release) normalized to the increase in fluorescence obtained after lysis of preincubation sample with 0.2% Triton X-100 (100% release) (Kirpotin, D. et al., *FEBS Letters*, 388:115–118 (1996)). Results of various cysteine-mediated cleavage experiments are shown in FIGS. 8 and 9.

Example 7

In vivo Characterization of Liposomes Comprising mPEG-DTB-DSPE Conjugates

A. Liposome Preparation

The lipids partially hydrogenated phosphatidylcholine (PHPC), cholesterol and either non-cleavable mPEG-DSPE or para-mPEG-DTB-DSPE (R=H, CH$_3$, C$_2$H$_5$, all derived from mPEG MW=2000 Daltons) were dissolved in a 55:40:5 mole percent ratio, respectively, in an organic solvent. The solvent was removed by rotary evaporation to form a dried lipid film. The film was hydrated with aqueous buffer containing diethylene triamine pentacetic acid (EDTA) to form liposomes. After downsizing the liposomes to an average diameter of 120 nm unentrapped EDTA was removed and liposomes were labeled with In$^{111}$ that was entrapped in the internal aqueous compartment.

B. In vivo Administration

Mice were divided into five study groups, each group for a different liposomal formulation varying the lipopolymer or a conventional formulation without a lipopolymer. The liposome compositions were injected intravenously into test animals. Liposome content in the blood was determined by monitoring blood samples for In$^{111}$. The results are shown in FIG. 10.

Example 8

Preparation and Purification of PEG-Lysozyme Conjugates

Lysozyme (at final concentration of 10 mg/mL) was allowed to react in borate buffer (0.1 M, pH 8.0) at 25° C. for 2–5 h with either mPEG-MeDTB-NPC of mPEG-NPC, using the feed molar ratio of 3.5 PEG/lysozyme (0.5 PEG/amino group). The conjugation reactions were quenched by the addition of 10-fold excess of glycine.

PEG-lysozyme conjugates were purified on a CM HEMA-IEC Bio 1000 semi-preparative HPLC column (7.5×150 mm) purchased from Alltech Associates, Deerfield, Ill. First, the conjugation reaction was injected into the HPLC column in 10 mM sodium acetate buffer pH 6. The elution with this buffer was continued until all unreacted PEG was removed. Then 0.2 M NaCl in 10 mM sodium acetate pH 6 was applied for 15 minutes in order to elute the PEGylated-lysozyme. Finally, the native lysozyme was eluted by increasing the salt concentration to 0.5 M NaCl over 20 min. Fractions (1 mL) were collected and assayed for protein and PEG contents. Thus aliquots (25 µL) of each fraction were reacted with BCA protein assay reagent (200 µL, Pierce Chemical Company, Rockford, Ill.) in microtiter plate wells at 37° C. for 30 min, and the absorbance was read at 562 nm. Similarly, for PEG determination (Zalipsky, S., *PEG Chemistry and Biol Appl ACS* pps. 318–341, (1997)) 25 µL aliquots were reacted with 0.1% polymethacrylic acid solution in 1 N HCl (200 µL), in microtiter plate wells, followed by absorbance reading at 400 nm. Fractions containing both protein and PEG were pooled. For the isolation of the PEG-lysozyme containing only one PEG moiety, the same cation exchange chromatography protocol was used and the collected fractions were analyzed by the HPLC reversed-phase assay. Fractions containing the single peak of 1:1 PEG per lysozyme conjugate species were pooled.

Reverse-phase HPLC analysis. RP-HPLC separation of PEG-lysozyme conjugates was achieved on a Vydac™ Protein C4 (4.6×150 mm) column eluted at 1 ml/min with aqueous acetonitrile gradient as follows. Each chromatography run started with a mobile phase A (30% acetonitrile, 5% 0.1 M sodium acetate pH 5, and 65% H$_2$O), and over a period of 40 min ended with a mobile phase B (50% acetonitrile, 50% 0.1 M sodium acetate pH 5). UV detector set at 280 nm was used to monitor the chromatography.

SDS-PAGE. Polyacrylamide gel electrophoresis under denaturing conditions was performed for conjugates characterization. Pre-cast NuPAGE® Bis-Tris gels (4–15%), NuPAGE® MES running buffer, molecular weight protein standards (Mark 12™), and Colloidal Coomassie® G-250 staining kit, were all obtained from Invitrogen, Carlsbad, Calif. In a typical electrophoresis, 1 to 3 µg of protein containing sample were loaded per well on the gel, then electrophoresed at constant voltage of 200 mV, and stained for protein according to the manufacturer instructions. For PEG detection, a duplicate gel was stained with iodine according to Kurfürst, M. M., Analyt Biochem 200:244–248, (1992).

DePEGylation experiments. Mixture of purified mPEG-DTB-lysozyme conjugates (2 mg/mL protein), containing 1:1, 2:1, and 3:1 conjugate species, was incubated with 1 mM cysteine in 0.1 M sodium phosphate buffer pH 7.3 containing 5 mM EDTA, at 37° C. on a rocking mixer. Aliquots were taken out from the reaction vial at various time points and analyzed by RP-HPLC as described above (see FIG. 13A). Recovery of enzymatic activity of lysozyme after de-PEGylation of mPEG-DTB-Lysozyme is demonstrated in FIG. 13B. This is in contrast to the non-cleavable mPEG-Lysozyme that remained inactive regardless of the Cys treatment. De-PEGylation of the 1:1 PEG-lysozyme (0.5 mg/ml protein) treated at room temperature with 1 mM cysteine or glutathione was also followed by the same RP-HPLC method.

LC-MS. Purified PEG-DTB-lysozyme containing only one PEG moiety per lysozyme was treated with 1 mM cysteine while the reaction was monitored by LC-MS. The HPLC system (HP 1100 LC-102) equipped with the same C4 column as described above was connected to an electrospray mass spectrometer (Micromass QTOF II), permitting peaks identification by their molecular weights. The sodium acetate in the mobile phase was replaced with ammonium acetate in order to minimize salt interference with the electrospray ionization. As shown in FIG. 14, identical spectra was obtained for the native lysozyme and for de-PEGylated mPEG-DTB-Lysozyme. This study confirms that the thiolytic de-PEGylation reaction used in this invention proceeds cleanly without detectable protein-by products.

Example 9

Preparation of mPEG-DTB-EPO Conjugates

Stock solutions of 16 mM mPEG$_{12000}$-MeDTB-NPC (199.6 mg/mL) and mPEG12k-NPC (195.3 mg/mL) in acetonitrile were prepared.

Recombinant, human erythropoietin (EPO, EPREX®) was obtained preformulated at a protein concentration of 2.77 mg/mL in 20 mM Na citrate, 100 mM NaCl buffer pH 6.9.

A borate buffer (pH 8) was prepared as follows. 500 mM Na borate solution was made by dissolving 4.77 mg of sodium tetraborate in 100 dH$_2$O. The buffer was filtered though 0.45 μm filter. The final concentration was 500 mM of Na borate.

A phosphate buffer pH 7 was prepared as follows. 500 mM Na phosphate solution was made by dissolving 13.45 mg of sodium phosphate monobasic monohydrate and 54.6 mg of sodium phosphate dibasic, 12H$_2$O in dH$_2$O, and the pH was adjusted to 7.0 using 5 N NaOH. The buffer was filtered though 0.45 μm filter. The final concentrations was 500 mM of Na phosphate.

A. Preparation of "Lightly PEGyated" EPO

EPO was conjugated to mPEG$_{12000}$-MeDTB-NPC at a PEG/protein molar ratio of 6/1 with the amount of reactants set forth below:

|  |  | Initial Conc. | Volume | Final Conc. |
| --- | --- | --- | --- | --- |
| EPO |  | 2.77 mg/mL | 7.22 mL | 2 mg/mL (0.066 mM) |
| dH$_2$O |  |  | 0.53 mL |  |
| PO$_4$ buffer |  | 500 mM | 2 mL | 100 mM |
| mPEG$_{12000}$-MeDTB-NPC | PEG | 16 mM | 0.25 mL | 0.4 mM |
|  | Acetonitrile | 100% |  | 2.5% |
| Reaction volume |  |  | 10 mL |  |
| PEG/EPO molar ratio |  |  |  | 6/1 |

EPO was conjugated to mPEG$_{12000}$-NPC at a PEG/protein molar ratio of 8/1 with the amount of reactants set forth below:

| Reactant |  | Initial Conc. | Volume | Final Conc. |
| --- | --- | --- | --- | --- |
| EPO |  | 2.77 mg/mL | 7.22 mL | 2 mg/mL (0.066 mM) |
| dH$_2$O |  |  | 0.45 mL |  |
| PO$_4$ buffer |  | 500 mM | 2 mL | 100 mM |
| mPEG$_{12000}$-NPC | PEG | 16 mM | 0.33 mL | 0.4 mM |
|  | Acetonitrile | 100% |  | 2.5% |
| Reaction volume |  |  | 10 mL |  |
| PEG/EPO molar ratio |  |  |  | 8/1 |

The reactions were carried out at room temperature (20–22° C.) for 4.5 hours in polypropylene vials, on a rocking mixer. At the end of the incubations, the vials were stored at 2–8° C.

A. Preparation of "Lightly PEGylated" EPO

EPO was conjugated to mPEG$_{12000}$-MeDTB-NPC at a PEG/protein molar ratio of 9/1 with the amount of reactants set forth below:

|  |  | Initial Conc. | Volume | Final Conc. |
| --- | --- | --- | --- | --- |
| EPO |  | 2.77 mg/mL | 5.05 mL | 2 mg/mL (0.066 mM) |
| dH$_2$O |  |  | 0.29 mL |  |
| Borate buffer pH 8 |  | 500 mM | 1.4 mL | 100 mM |
| mPEG$_{12000}$-MeDTB-NPC | PEG | 16 mM | 0.262 mL | 0.6 mM |
|  | Acetonitrile | 100% |  | 2.5% |
| Reaction volume |  |  | 7 mL |  |
| PEG/EPO molar ratio |  |  |  | 9/1 |

EPO was conjugated to mPEG$_{12000}$-NPC at a PEG/protein molar ratio of 12/1 with the amount of reactants set forth below:

|  |  | Initial Conc. | Volume | Final Conc. |
|---|---|---|---|---|
| EPO |  | 2.77 mg/mL | 5.05 mL | 2 mg/mL (0.066 mM) |
| dH$_2$O |  |  | 0.2 mL |  |
| Borate buffer pH 8 |  | 500 mM | 1.4 mL | 100 mM |
| mPEG$_{12000}$-MeDTB-NPC | PEG | 16 mM | 0.35 LI | 0.8 mM |
|  | Acetonitrile | 100% |  | 2.5% |
| Reaction volume |  |  | 7 mL |  |
| PEG/EPO molar ratio |  |  |  | 12/1 |

The reactions were carried out at room temperature (20–22° C.) for 4.5 hours in polypropylene vials, on a rocking mixer. At the end of the incubations, the vials were stored at 2–8° C.

C. Purification and Concentration

Prior to purification, the conjugates were dialyzed in 20 mM Tris pH 7.5 buffer and filtered through 0.2 μm Acrodisc® HT Tuffryn low protein binding syringe filter. The purification was done on a 1 mL Q XL anion exchanger column obtained from Amersham Biosciences Corp. (Piscataway, N.J.), using a step gradient elution profile from mobile phase A containing 20 mM Tris pH 7.5 buffer, to mobile phase B containing 500 mM NaCl in 20 mM Tris pH 7.5 buffer. The gradient was: 100% A for 8 minutes, 18% B for 25 minutes, then 70% B for 10 minutes. Elution fractions were collected in polypropylene tubes at 1 mL per fraction. The fractions eluting at 18% of mobile phase B (90 mM NaCl) were identified as the purified conjugates fractions (10 fractions), pooled in one tube, and stored at 2–8° C.

The purified mPEG$_{12000}$-MeDTB-EPO and mPEG$_{12000}$-EPO were dialyzed in 20 mM sodium citrate, 100 mM NaCl buffer pH 6.9 (4 exchanges of 4 L buffer), using a Spectra/Por 6000–8000 MW cutoff dialysis tubing. A 10 mL Amicon concentrator with a YM10 membrane were used to bring down each sample volume from 10 to approximately 4.5 mL, under 45–50 psi nitrogen pressure.

D. Characterization

1. SDS-PAGE

The PEGylated-EPO preparations were run on two SDS-PAGE gels as follows. Three μg of each reaction solution were loaded per well on a NuPAGE® Bis-Tris 4–12% gel purchased from Invitrogen (Carlsbad, Calif.), and let run for 55 minutes in MOPS running buffer at 200 Volts (constant voltage). EPO reference was loaded at 1.5 μg/well.

One of the gels was washed with 3×100 ml dH$_2$O, transferred to a Simply Blue™ stain for 1 hour, while gently shaking, then let soaked for 18 hours in 100 ml dH$_2$O containing 20 ml of 20% NaCl.

The other gel was stained with iodine for PEG detection, as follows. The gel was let sit in 200 mL of 5% glutaraldehyde solution for 20 minutes, then soaked twice in 200 mL of 0.1 M perchloric acid solution for 15 minutes each. To the second acid bath, 50 mL of 5% barium chloride and 25 mL of 1.3% iodine (made in 2% potassium iodide) solutions were added for 20 minutes (light protected). The gel was washed for 20 minutes in dH$_2$O, and scanned shortly after. All incubation baths were on a gentle rotating shaker. The results are shown in FIGS. 17A–17B.

2. SEC-HPLC

The PEGylated-EPO preparations were analyzed by size exclusion chromatography using TSK-Gel G3000SW XL 7.5×30 cm HPLC column obtained from Tosoh Bioscience. The mobile phase was 50 mM sodium phosphate, 150 mM NaCl pH 6.5. Samples were diluted to 50 μg/mL in the mobile phase, and 50 μL of each were injected to the column and eluted at a flow rate of 0.5 mL/min for 30 minutes. The column was connected to an on-line florescence detector set for intrinsic tryptophan detection (Exλ=260 nm, Emλ=360 nm). The results are shown in FIGS. 18A–18D.

Example 10

Preparation of Exemplary mPEG-DTB-Drug Conjugates

A. mPEG-DTB-Mitomycin C (FIG. 20A)

A 50 mL round bottom flask charged with phosgene (3 mmol) solution in toluene (5 mL). It was cooled to 5° C. A solution of mPEG$_{12K}$-MeDTB-OH (prepared as in Example 2, 3.8 g, 0.31 mmol) in dry methylene chloride (10 mL) was prepared. The alcohol solution was then added slowly to the phosgene solution. The reaction solution was allowed to warm to room temperature overnight. The solution was rotary evaporated in vacuo to remove the excess phosgene. The crude acyl chloride was redissolved in dry methylene chloride (10 mL).

A solution of mitomycin C (MMC, 0.35 mmol), dimethylaminopyridine (0.1 mmol) and dimethylformamide (DMF, 2 mL) was prepared. The MMC solution was slowly added to the acyl chloride solution. After overnight reaction, the methylene chloride was evaporated off and the crude product was recovered by addition of isopropanol followed by filtration. The mPEG-DTB-MMC conjugate was further purified by two precipitation from ethanol. Yield: 3.4 g. The MMC content (≈90%) was determined by UV. The conjugate was further characterized by $^1$H NMR (360 MHz, CDCl$_3$): δ 1.18 (d, J=7.5, 3H), 1.76 (s, 3H), 2.96–3.03 (m, 3H), 3.19 (s, 3H), 3.29 (dd, J=4.7 and 2.9 Hz, 1H), 3.41 (dd, J=5.0 and 2.2 Hz, 1H), 3.48 (dd, J=13.7 and 2.5 Hz, 1H), 3.60 (s, PEG, 1000H), 4.15 (t, OCOCH$_2$, 2H), 4.27–4.36 (m, 2H), 4.43 (d, J=13.3 Hz, 1H), 4.61 (s, 2H), 4.90 (ddd, J=10.4 and 5.0 and 2.2 Hz, 1H), 5.00 (s, 2H), 7.32 (d, J=8.6 Hz, 2H), 7.50 (d, J=7.9 Hz, 2H).

B. mPEG-DTB-Paclitaxel (FIG. 20C)

A solution of mPEG$_{12K}$-MeDTB-OH (3 g, 0.25 mmol) in dry methylene chloride (7 mL) was treated with 20% phosgene solution in toluene (2 mmol, 1 mL) at 5° C. overnight. During this time the solution was allowed to warm to room temperature overnight. The solution was rotary evaporated in vacuo to remove the excess phosgene. The crude acyl chloride was redissolved in dry methylene chloride (7 mL) and gradually added to paclitaxel (0.43 g, 0.5 mmol) solution in dry pyridine (10 mL). After overnight reaction, the methylene chloride was rotary evaporated and the crude product was recovered by addition of isopropanol followed by filtration. The mPEG-MeDTB-paclitaxel conjugate was further purified by two precipitation from ethanol. Yield: 2.6 g. The product was characterized by NMR (CDCl$_3$), which suggested that 2'-carbonate of paclitaxel was formed (C-2' proton of the drug at 4.7 ppm appeared as a doublet at 5.5 ppm in the conjugate). All the characteristic signals of mPEG-MeDTB and the drug, in close to 1:1 ratio, were also observed.

Although the invention has been described with respect to particular embodiments, it will be apparent to those skilled in the art that various changes and modifications can be made without departing from the invention.

The invention claimed is:

1. A conjugate having the general structure I:

$$P\text{-}L\text{-}CR^1R^2\text{—}S\text{—}S\text{—}Ar\text{—}CR^3R^4\text{—}Y\text{—}X^3\text{—}R^5 \quad\quad I$$

wherein:
P is a hydrophilic polymer and L is a linker moiety;
R$^1$, R$^2$, R$^3$ and R$^4$ are independently selected from the group consisting of H, alkyl, aralkyl and aryl;
Ar is an aromatic group to which S—S and CR$^3$R$^4$ are linked in a configuration which promotes rapid cleavage of the CR$^3$R$^4$—Y bond, via a 1,4-, 1,6- or related elimination reaction involving the bonds of the aromatic group, following cleavage of the S—S bond;
Y is a direct bond or —X$^1$—(C=X$^2$)—, where X$^1$ and X$^2$ are independently O or S; and
X$^3$R$^5$ is a ligand derived from an amine-, hydroxy- or carboxyl-containing compound, such that X$^3$ is an oxygen or secondary or tertiary nitrogen atom.

2. The conjugate of claim 1, wherein Ar is selected from
(i) an aromatic hydrocarbon or a ring nitrogen-containing analog thereof, to which groups S—S and CR$^3$R$^4$ are linked in such a configuration that they are separated by an odd number of peripheral ring bonds;
(ii) a 5-membered heteroaromatic ring selected from 2,4-imidazolyl, 2,4-thiazolyl, 2,4-oxazolyl, 2,5-pyrrolyl, 2,5-furanyl, and 2,5-thiophenyl, and
(iii) a polycyclic aromatic group containing a 5-membered heteroaromatic ring, to which groups S—S and CR$^3$R$^4$ are linked in such a configuration that they are separated by a path containing an odd number of peripheral ring bonds, with the proviso that said path does not include an oxygen, sulfur, or trisubstituted nitrogen ring atom.

3. The conjugate of claim 1, wherein the linker moiety L is a direct bond, amine, amide, carbamate, ether, or a carbon chain, where the carbon chain may have one or more functional groups selected from amine, amide, carbamate, and ether, at either terminus of the chain or intervening between carbon atoms of the chain.

4. The conjugate of claim 2, wherein Ar is selected from 1,2-phenyl, 1,4-phenyl, 1,7-napthyl, 2,9-anthracyl, and 4,5-phenanthracyl.

5. The conjugate of claim 4, wherein Ar is selected from 1,2-phenyl and 1,4-phenyl.

6. The conjugate of claim 1, wherein Y is O(C=O), and the ligand is derived from an amine-containing compound.

7. The conjugate of claim 1, wherein R$^1$ is H and R$^2$ is selected from the group consisting of CH$_3$, C$_2$H$_5$ and C$_3$H$_7$.

8. The conjugate of claim 1, wherein the ligand is derived from a polypeptide, an amine-containing drug, or an amine-containing lipid.

9. The conjugate of claim 8, wherein the amine-containing lipid is a phospholipid having a double hydrocarbon tail.

10. The conjugate of claim 1, wherein each of R$^1$ and R$^2$ is alkyl.

11. The conjugate of claim 1, wherein the hydrophilic polymer P is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethylene glycol, polyaspartamide, copolymers thereof, and polyethylene oxide-polypropylene oxide.

12. The conjugate of claim 11, wherein P is polyethylene glycol.

13. The conjugate of claim 12, wherein R$^1$ is H and R$^1$ is CH$_3$, C$_2$H$_5$, or C$_3$H$_7$.

14. The conjugate of claim 1, wherein the ligand is derived from a polypeptide.

15. The conjugate of claim 14, wherein the polypeptide is a recombinant polypeptide.

16. The conjugate of claim 11, wherein the polypeptide is a recombinant polypeptide.

17. The conjugate of claim 14, wherein the polypeptide is a cytokine.

18. The conjugate of claim 14, wherein the polypeptide is selected from the group consisting of interferons, interleukins, growth factors, erythropoietin, and enzymes.

19. The conjugate of claim 14, comprising multiple hydrophilic polymers attached to said polypeptide, each by a linkage represented by L-CR$^1$R$^2$—S—S—Ar—CR$^3$R$^4$—Y in structure I.

20. The conjugate of claim 11, wherein said hydrophilic polymer includes a targeting moiety at its free terminus.

* * * * *